US008119772B2

(12) United States Patent
Yang et al.

(10) Patent No.: US 8,119,772 B2
(45) Date of Patent: Feb. 21, 2012

(54) MART-1 T CELL RECEPTORS

(75) Inventors: Lili Yang, Arcadia, CA (US); David Baltimore, Pasadena, CA (US); Pin Wang, Arcadia, CA (US); James Economou, Pacific Palisades, CA (US); Antoni Ribas, Los Angeles, CA (US)

(73) Assignees: California Institute of Technology, Pasadena, CA (US); Regents of the University of California, Oakland, CA (US)

( * ) Notice: Subject to any disclaimer, the term of this patent is extended or adjusted under 35 U.S.C. 154(b) by 0 days.

(21) Appl. No.: 11/864,841

(22) Filed: Sep. 28, 2007

(65) Prior Publication Data
US 2008/0199424 A1    Aug. 21, 2008

Related U.S. Application Data

(60) Provisional application No. 60/848,207, filed on Sep. 29, 2006.

(51) Int. Cl.
A61K 35/14    (2006.01)
(52) U.S. Cl. .................................. 530/381; 435/325
(58) Field of Classification Search .................. None
See application file for complete search history.

(56) References Cited

U.S. PATENT DOCUMENTS

| | | | |
|---|---|---|---|
| 4,886,499 A | 12/1989 | Cirelli et al. | |
| 5,279,552 A | 1/1994 | Magnet | |
| 5,328,483 A | 7/1994 | Jacoby | |
| 5,848,991 A | 12/1998 | Gross et al. | |
| 5,997,501 A | 12/1999 | Gross et al. | |
| 6,494,865 B1 | 12/2002 | Alchas | |
| 6,569,143 B2 | 5/2003 | Alchas et al. | |
| 6,670,349 B1 | 12/2003 | Nyce | |
| 6,689,118 B2 | 2/2004 | Alchas et al. | |
| 6,776,776 B2 | 8/2004 | Alchas et al. | |
| 6,780,171 B2 | 8/2004 | Gabel et al. | |
| 6,808,506 B2 | 10/2004 | Lastovich et al. | |
| 6,971,999 B2 | 12/2005 | Py et al. | |
| 7,047,070 B2 | 5/2006 | Wilkinson et al. | |
| 7,083,592 B2 | 8/2006 | Lastovich et al. | |
| 7,083,599 B2 | 8/2006 | Alchas et al. | |
| 7,108,679 B2 | 9/2006 | Alchas | |
| 7,115,108 B2 | 10/2006 | Wilkinson et al. | |
| 7,241,275 B2 | 7/2007 | Alchas et al. | |
| 2005/0037445 A1 | 2/2005 | Poulsen et al. | |
| 2005/0238626 A1 | 10/2005 | Yang et al. | |
| 2007/0020238 A1 | 1/2007 | Baltimore et al. | |
| 2007/0116690 A1 | 5/2007 | Yang et al. | |
| 2008/0019998 A1 | 1/2008 | Wang et al. | |

FOREIGN PATENT DOCUMENTS

WO    WO 2006/000830 A2    1/2006
WO    WO 2006129085 A2 *  12/2006

OTHER PUBLICATIONS

Lederman et al., Molecular Immunology 28: 1171-1181, 1991.*
Colman et al., Research in Immunology, 1994; 145(1): 33-36.*
Abaza et al., Journal of Protein Chemistry, vol. 11, No. 5, 1992, pp. 433-444.*
Garcia et al., Cell, vol. 122, 333-336, Aug. 12, 2005.*
Portolano et al., J Immunol. Feb. 1, 1993;150(3):880-7.*
Birgl et al., J. Immunol. 2006;176;3625-3634.*
Genbank accession No. DQ341452, published Mar. 17, 2006.*
Genbank accession No. DQ341462, published Mar. 17, 2006.*
Janeway et al., Immunobiology, 5th Ed., Garland Science, pp. 106-108 and 260-263, (2001).*
Antony et al.,"CD8+Cell Immunity Against a Tumor/Self-Antigen Is Augmented by CD4+ T Helper Cells and Hindered by Naturally Occurring T Regulatory Cells," *J Immunol* 174:2591-2601, 2005.
Cochran et al., Cancer Treatment, 5th Edition, Charles M. Haskell ed., W.B. Saunders 179-198, 2002.
Delves, P.J. and Roitt, I.M., "The Immune System," *N. Engl J Med* 343:108-117, 2000.
Dubey et al., "Quantitative imaging of the T Cell antitumor response by positron-emission tomography," *Proc Natl Acad Sci USA* 100:1232-1237, 2003.
Dudley et al., "Cancer Regression and Autoimmunity in Patients After Clonal Repopulation With Antitumor Lymphocytes," *Science* 298:850-854, 2002.
Dudley et al., "Adoptive Cell Transfer Therapy Following Non-Myeloablative but Lymphodepleting Chemotherapy for the Treatment of Patients with Refractory Metastatic Melanoma," *J Clin Oncol* 23:2346-2357, 2005.
Dudley et al., "A Phase I Study of Nomyeloablative Chemotherapy and Adoptive Transfer of Autologous Tumor Antigen-Specific T Lymphocytes in Patients With Metastatic Melanoma," *J. Immunother* 25:243-251, 2002.
Eigentler et al., "Palliative therapy of disseminated malignant melanoma: a systematic review of 41 randomised clinical trials," *Lancet Oncol* 4:748-759, 2003.
Fong et al., "Dendritic Cells Injected Via Different routes Induce Immunity in Cancer Patients," *J. Immunol* 166:4254-4259, 2001.
Fontenot et al.,"Regulatory T Cell Lineage Specification by the Forkhead Transcription Factor Foxp3," *Immunity* 22:329-341, 2005.
Gao, G.F. and Jakobsen, B.K.,"Molecular interactions of coreceptor CD8 and MHC class I: the molecular basis for functional coordination with the T-cell receptor," *Immunol Today* 21:630-636, 2000.
Genseq database entry AEF19312, Mar. 9, 2006, 274 amino acid Human T cell receptor, TRAC*01, alpha chain #2 from WO 2006/000830.
Gattinoni et al., "Adoptive immunotherapy for cancer: building on success," *Nat Rev Immunol* 6:383-393, 2006.
Holmberg et al., "TCR Binding Kinetics Measured with MHC Class I Tetramers Reveal a Positive Selecting Peptide with Relatively Hight affinity for TCR[1],"*J Immunol* 171:2427-2434, 2003.
Klebanoff et al., "Central memory self/tumor-reactive CD8+T cells confer superior antitumor immunity compared with effector memory T cells," *Proc Natl Acad Sci USA* 102:9571-9576, 2005.
Lou et al., "Dendritic Cells Strongly Boost the Antitumor Activity of Adoptively Transferred T Cells in vivo," *Cancer Res* 64:6783-6790, 2004.
Overwijk et al., "Tumor Regression and Autoimmunity After Reversal of a Functionally Tolerant State of Self-Reactive CD8+T Cells," *J Exp Med* 198:569-580, 2003.

(Continued)

Primary Examiner — Zachary Skelding
(74) Attorney, Agent, or Firm — Knobbe, Martens, Olson & Bear LLP

(57) ABSTRACT

T-cell receptors that recognize MART-1 antigen are provided. The TCRs can be used, for example, to treat patients suffering from melanoma.

14 Claims, 11 Drawing Sheets

OTHER PUBLICATIONS

PCT International Search Report for PCT/US2007/80004, mailed Sep. 29, 2008.

Pitcher, L.A. and Oers, N. S., "T-cell receptor signal transmission: who gives an ITAM?," *Trends Immunol* 24:554-560, 2003.

Ribas et al., "Determinant spreading and tumor responses after peptide-based cancer immunotherapy," *Trends Immunol* 24:58-61, 2003.

Rosenberg et al., "Cancer immunotherapy: moving beyond current vaccines," *Nat Med*, 10:909-915, 2004.

Roszkowski et al., "CD8-Independent Tumor Cell Recognition Is a Property of the T cell Receptor and Not the T Cell[1]"*J Immunol* 170:2582-2589, 2003.

Rubinstein et al., "Transfer of TCR Genes into Mature T Cells Is Accompanied by the Maintenance of Parental T Cell Avidity," *J Immunol* 170:1209-1217.

Savage et al., "A Kinetic Basis for T Cell Receptor Repertoire Selection During an Immune Response," *Immunity* 10:485-492, 1999.

Tsao et al, "Management of Cutaneous Melanoma" *N. Engl J Med* 351:998-1012, 2004.

US-10-482-029-219, SEQ ID NO: 219.

Chapter 4 of Janeway et al, Immunobiology, the Immune System in Health and Disease, 3rd edition, 1997, published by Current Biology Ltd., 4-1 to 4-31.

\* cited by examiner

A) Tetramer staining

B) Cytokine assay

C)

MART-1 T CELL RECEPTORS

CROSS-REFERENCE TO RELATED APPLICATIONS

The present application claims priority under 35 U.S.C. §119(e) to U.S. Provisional Application No. 60/848,207, filed Sep. 29, 2006, which is incorporated herein by reference in its entirety.

REFERENCE TO SEQUENCE LISTING, TABLE, OR COMPUTER PROGRAM LISTING

The present application is being filed along with a Sequence Listing in electronic format. The Sequence Listing is provided as a file entitled SEQLIST_CALTE__037.TXT, created Sep. 27, 2007, which is 51 Kb in size. The information in the electronic format of the Sequence Listing is incorporated herein by reference in its entirety.

BACKGROUND OF THE INVENTION

1. Field of the Invention

The invention generally relates to MART-1 T cell receptors and their use, for example in the prevention and treatment of melanoma in patients.

2. Description of the Related Art

Locally advanced and metastatic melanoma is well-known to be resistant to standard forms of therapy. Two agents are currently approved for the treatment of stage IV melanoma: (1) the chemotherapy drug DTIC (or Dacarbazine), and (2) interleukin-2 (IL-2) administered in high doses (Tsao, H., et al. 2004. *N Engl J Med* 351:998-1012; Cochran, A., et al. 2002. *Cancer Treatment, Fifth Edition, Charles M. Haskell, ed., W.B. Saunders:* 179-198). Both agents incur response rates below 15%, and neither form of therapy has been shown to increase survival in a randomized trial. The addition of more chemotherapy or combinations of chemotherapy with IL-2 ("biochemotherapy" regimens) has failed to improve survival in over 10 randomized clinical trials (Tsao, H. et al. 2004. supra; Eigentler, T. K., et al. 2003. *Lancet Oncol* 4:748-759).

An important step in the treatment of cancer with immunotherapy has been the identification of tumor antigens capable of stimulating T cell responses. Cytotoxic T cells ("CTLs," "CD8 T cells") have been shown to be the major effector cells that mediate tumor rejection. Active immunotherapy with several forms of cancer vaccines has shown that antigen-specific T cells can be activated and lead to anti-tumor responses (Ribas, A., et al. 2003. *Trends Immunol* 24:58-61).

Adoptive therapy is one approach that can overcome the immunotherapy ceiling of approximately 10-15% objective responses for clinical antitumor activity (Rosenberg, S. A., et al. 2004. *Nat Med* 10:909-915). It is a form of passive immunotherapy in which a host is directly provided with effectors to react against cancer, such as, for example, by direct presentation of in vitro expanded or modified anti-tumor T cells to the host. Adoptive transfer procedures of large numbers of clonally-expanded antigen-specific T cells into patients with melanoma have been studied. In these studies, patients received a conditioning regimen to deplete endogenous lymphocytes (non-myeolablative but lymphodepleting), together with high doses of interleukin-2 (IL-2). The adoptive transfer of large numbers of antigen-specific CD8+ T cells, generally obtained from tumor infiltrating lymphocytes (TIL), leads to the highest percentage of tumor regressions reported in patients with melanoma. In clinical trials at the NCI Surgery Branch, 50% of patients with metastatic melanoma had objective responses (Dudley, M. E., et al. 2002. *Science* 298: 850-854; Dudley, M. E., et al. 2005. *J Clin Oncol,* 23:2346-2357). However, the procedure is difficult to implement outside of pilot studies due to its requirement for extensive ex vivo manipulations.

The use of genetic engineering of T cells with T-cell receptors (TCRs) as described herein can make adoptive therapy more broadly applicable, and the insertion of reporter genes in such an approach can further permit the study of their immunobiology and tumor trafficking in vivo. In addition, this approach allows for the generation of large numbers of T cells with specificity for melanoma tumor antigens with a relatively short duration (less than one week) of ex vivo cell manipulation.

The TCR is a complex surface protein complex composed of eight different subunits organized in dimers: the TCR α and β chains, a CD3 ζ:CD3 ζ homodimer, and CD3ε:CD3γ and CD3ε:CD3δ heterodimers. (See FIG. 1.) The TCR chains have distal variable regions (Vα and Vβ) that interact with the MHC/antigen determinant as well as proximal constant regions (Cα and Cβ) (Delves, P. J. and Roitt, I. M. 2000. *N Engl J Med* 343:108-117). The distal V regions have Ig-like folds, with 3 loops or complimentary determinant regions (CDR) from each chain creating the binding face that interacts with antigen. The CD3 complex is involved in stable TCR expression on the cell surface and signal transduction upon antigen encounter, resulting in a signaling cascade that culminates in T cell differentiation, proliferation and acquisition of effector functions (Pitcher, L. A. and van Oers, N. S. 2003. *Trends Immunol* 24:554-560). The CD4 and CD8 co-receptors increase the affinity of the TCR/MHC-antigen, which results in enhanced TCR signaling but does not alter the specificity of the TCR-antigen interaction (Gao, G. F. and Jakobsen, B. K. 2000. *Immunol Today* 21:630-636; Arcaro, A., et al. 2000. *J Immunol* 165:2068-2076).

SUMMARY OF THE INVENTION

In one aspect of the invention, nucleic acids that encode one or more subunits of a MART-1 TCR are provided. In some embodiments, a nucleic acid encodes a TCR-α subunit polypeptide comprising an amino acid sequence having at least 80% sequence identity to SEQ ID NO: 3. In other embodiments, a nucleic acid encodes a polypeptide comprising a TCR-α subunit variable region comprising an amino acid sequence having at least 80% sequence identity to SEQ ID NO: 4. In some other embodiments, nucleic acids encoding a TCR-β subunit are provided. The nucleic acids preferably encode polypeptides comprising an amino acid sequence having at least 80% identity to SEQ ID NO: 15 or at least 95% sequence identity to SEQ ID NO: 7. In still other embodiments, nucleic acid encoding TCR-β subunits comprising amino acid sequences having at least 95% sequence identity to SEQ ID NO: 8 or at least 80% sequence identity to SEQ ID NO: 16.

Additional embodiments include nucleic acid sequences encoding a TCR-β subunit, the nucleic acid comprising a nucleotide sequence having at least 80% sequence identity to SEQ ID NO: 13. In some additional embodiments, the compositions comprise a nucleic acid encoding a TCR-β subunit, the nucleic acid comprising a nucleotide sequence having at least 80% sequence identity to SEQ ID NO: 14.

In another aspect of the invention, polypeptide sequences from a MART-1 TCR are provided. In some embodiments, the polypeptides comprise an isolated TCR subunit comprising a polypeptide sequence with at least 80% sequence identity to SEQ ID NO: 3. In other embodiments, the polypeptides comprise an isolated TCR subunit comprising a variable region polypeptide sequence with at least 80% sequence identity to SEQ ID NO: 4. In some other embodiments, the polypeptides comprise an isolated TCR subunit comprising a polypeptide sequence with at least 95% sequence identity to SEQ ID NO: 7. In still other embodiments, the polypeptides comprise an isolated TCR subunit comprising a variable region polypeptide sequence with at least 95% sequence identity to SEQ ID NO: 8. Additional embodiments include polypeptides comprising an isolated TCR subunit comprising a polypeptide sequence with at least 80% sequence identity to SEQ ID NO: 15. In some additional embodiments, the polypeptides comprise an isolated TCR subunit comprising a variable region polypeptide sequence with at least 80% sequence identity to SEQ ID NO: 16.

Embodiments of the invention also include cells comprising a MART-1 TCR. In some embodiments, the cells comprise a TCR comprising a polypeptide having at least 80% sequence identity to SEQ ID NO: 4. In certain embodiments, the TCR further comprises a polypeptide having at least 80% sequence identity to SEQ ID NO: 8.

In some embodiments of the invention, the cells contain a TCR comprising a polypeptide having at least 95% sequence identity to SEQ ID NO: 8.

In some embodiments, the cells contain a TCR comprising a polypeptide having at least 80% sequence identity to SEQ ID NO: 16. In certain embodiments, the TCR further comprise a polypeptide having at least 80% sequence identity to SEQ ID NO: 12.

In some embodiments of the invention, vectors encoding one or more subunits of a MART-1 TCR are provided. In some embodiments, the vectors comprise a nucleic acid sequence having at least 80% sequence identity to SEQ ID NO: 2. In certain embodiments, the vectors further comprise a nucleic acid sequence having at least 80% sequence identity to SEQ ID NO: 6.

In some embodiments, the vectors comprise a nucleic acid sequence having at least 95% sequence identity to SEQ ID NO: 6.

In some embodiments, the vectors comprise a nucleic acid sequence having at least 80% sequence identity to SEQ ID NO: 14. In certain embodiments, the vectors further comprise a nucleic acid sequence having at least 80% sequence identity to SEQ ID NO: 10.

In an aspect of the invention, recombinant viruses encoding one or more subunits of a MART-1 TCR are provided. In some embodiments, the recombinant viruses comprise at least one of: a nucleic acid sequence having at least 80% sequence identity to SEQ ID NO: 2; a nucleic acid sequence having at least 95% sequence identity to SEQ ID NO: 6; and a nucleic acid sequence having at least 80% sequence identity to SEQ ID: 14.

In some embodiments, the recombinant viruses comprise a nucleic acid sequence having at least 80% sequence identity to SEQ ID NO: 2 and a nucleic acid sequence having at least 80% sequence identity to SEQ ID NO: 6. In other embodiments, the recombinant viruses comprise a nucleic acid sequence having at least 80% sequence identity to SEQ ID NO: 10 and a nucleic acid having at least 80% sequence identity to SEQ ID NO: 14.

The recombinant viruses can further comprise a suicide gene. In some embodiments, the suicide gene is a thymidine kinase gene, such as an sr39tk gene having a sequence comprising SEQ ID NO: 18.

Embodiments of the invention further include methods of treating melanoma in a patient, the methods comprising: providing a population of target cells; transducing the population of target cells by contacting the target cells with a virus comprising at least one of: a nucleic acid sequence having at least 80% sequence identity to SEQ ID NO: 2, a nucleic acid sequence having at least 95% sequence identity to SEQ ID NO: 6 and a nucleic acid sequence having at least 80% sequence identity to SEQ ID: 14; and administering the population of transduced target cells to the patient. In some embodiments, the target cells are transduced by contacting the target cells with a virus comprising a nucleic acid having at least 80% sequence identity to SEQ ID NO: 2 and a nucleic acid having at least 80% sequence identity to SEQ ID NO: 6. In other embodiments, the target cells are transduced by contacting the target cells with a virus comprising a nucleic acid having at least 80% sequence identity to SEQ ID NO: 10 and a nucleic acid having at least 80% sequence identity to SEQ ID NO: 14.

In some embodiments, the target cells are peripheral blood mononuclear cells (PMBCs). In other embodiments, the target cells are hematopoietic stem cells (HSCs). In some embodiments, the target cells that are transduced express a T-cell receptor that specifically recognizes MART-1.

In some embodiments, the methods further comprise contacting the target cells with at least one of the following: CD2, CD3, and CD28. In certain embodiments, the methods further comprise isolating CD8+ T cells from the population of target cells.

In some embodiments, the methods further comprise mixing the transduced target cell population with unmanipulated cells and the population of transduced target cells is administered as the mixture to the patient.

In some embodiments, the methods further comprise administering at least one dose of interleukin-2 (IL-2) to the patient. In other embodiments, the methods further comprise administering a MART-1 dendritic cell vaccine to the patient.

Embodiments of the invention also include methods of generating T-cells against MART-1 antigen, the methods comprising: providing a population of cells comprising T cells; and contacting the population of cells with a recombinant virus comprising at least one of: a nucleic acid having at least 80% sequence identity to SEQ ID NO: 2, a nucleic acid having at least 95% sequence identity to SEQ ID NO: 6 and an isolated nucleic acid having at least 80% sequence identity to SEQ ID: 14. In some embodiments, the population of cells comprising T-cells are contacted with a recombinant virus comprising a nucleic acid having at least 80% sequence identity to SEQ ID NO: 2 and a nucleic acid having at least 80% sequence identity to SEQ ID NO: 6. In other embodiments, the population of cells comprising T-cells are contacted with a recombinant virus comprising a nucleic acid having at least 80% sequence identity to SEQ ID NO: 10 and a nucleic acid having at least 80% sequence identity to SEQ ID NO: 14.

In some embodiments, the methods further comprise contacting the population of cells comprising T-cells with at least one of the following: CD2, CD3, and CD28. In other embodiments, the methods further comprising isolating CD8+ T cells from the population of cells.

Embodiments of the invention also include methods of generating an immune response against MART-1 antigen in a patient, the methods comprising: providing a population of target cells; transducing the population of target cells by contacting the target cells with a virus comprising at least one of: a nucleic acid having at least 80% sequence identity to SEQ ID NO: 2, a nucleic acid having at least 95% sequence identity to SEQ ID NO: 6 and a nucleic acid having at least 80% sequence identity to SEQ ID: 14; and administering the population of transduced target cells to the patient. In some embodiments, the population of target cells is transduced by contacting the target cells with a virus comprising a nucleic acid having at least 80% sequence identity to SEQ ID NO: 2 and a nucleic acid having at least 80% sequence identity to SEQ ID NO: 6. In other embodiments, the population of target cells is transduced by contacting the target cells with a virus comprising a nucleic acid having at least 80% sequence identity to SEQ ID NO: 10 and a nucleic acid having at least 80% sequence identity to SEQ ID NO: 14.

BRIEF DESCRIPTION OF THE DRAWINGS

FIG. 2(*a*) shows how candidate α and β TCR chains were cloned from a population of over 90% MART-1 tetramer-positive cells expanded ex vivo from a particular patient as described herein. FIG. 2(*b*) shows the functionality testing results for three cloned α and β chains paired in different combinations. The "Tma14b2" pair (hereinafter referred to as "M1") was chosen for further studies based on superior expression of the TCR and specific signaling of the TCR upon transduction of peripheral blood mononuclear cells (PBMCs).

FIG. 5A illustrates MART-1$_{26-35}$/HLA-A2.1 tetramer analysis of transduced Jurkat cells ("Jurkat-M1"). FIG. 5B shows dose-dependent responses of Jurkat-M1 cells upon stimulation with T2 cells pulsed with peptide. Responses were measured according to IL-2 production in the cells. Alone: no stimulation (control); T2: stimulated with T2 cells alone (no peptide, control); T2/Flu: stimulated with T2 cells loaded with a unrelated peptide (control); T2/M1 (x): stimulated with T2 cells loaded with indicated (x) concentrations of MART-1$_{26-35}$ peptide in units of μg/mL. FIG. 5C illustrates the response of transduced PBMCs as quantified by IFN-γ production. M1 lentivirus-transduced PBMC responded to specific stimulated as quantified by IFN-γ production. T2/M1: stimulated by MART-1$_{26-35}$ peptide loaded T2 cells. T2/M3: stimulated by T2 cells loaded with an unrelated peptide (MAGE-3) as a specificity control.

FIG. 8*a* shows the results of a ganciclovir lysis assay for the transduced 293T cells as measured by cell viability. FIG. 8*b* shows the results of a [$^3$H]-pencyclovir uptake assay of the transduced 293T cells as measured by radioactivity.

DETAILED DESCRIPTION OF THE PREFERRED EMBODIMENT

Figure 1:
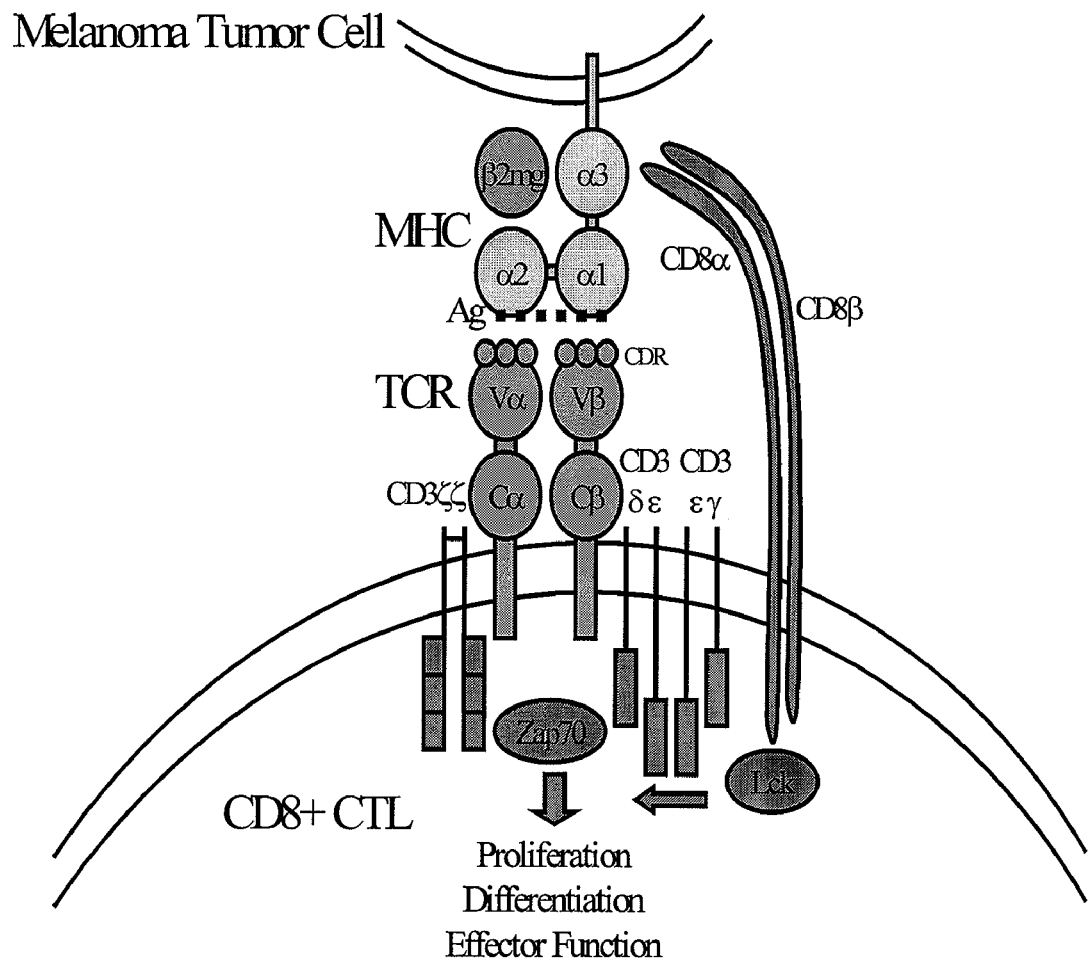
FIG. 1 is a schematic of the TCR/MHC class I interaction. The TCR has two chains, α and β, and it is the variable region (Vα and Vβ) of each chain that provides the specificity to bind to specific MTC class I antigens presented on the surface of target cells.

Compositions and methods related to MART-1 T cell receptors are provided, including nucleic acid and polypeptide sequences for particular subunits of TCRs, vectors comprising TCR sequences and methods of using such, for example for engineering a cell to express a T-cell receptor (TCR) against MART-1. In some embodiments, the compositions and methods are used for the treatment of melanoma in a patient.

MART-1 TCRs are generally able to bind MART-1, preferably with high affinity, and induce a functional T cell response upon antigen recognition. Two specific MART-1 TCRs are described herein: "M1" (also known as "Tma14b2") and "M2" (also known as "Tma3b15"). M1 TCR comprises an M1-α subunit and an M1-β subunit, while M2 TCR comprises an M2-α subunit and an M2-β subunit. Other MART-1 TCRs can be prepared by combining subunits and variable regions from the M1 and M2 MART-1 TCRs. For example, in some embodiments, a MART-1 TCR comprises at least one subunit selected from: M1-α, M1-β, M2α and M2-β. In other embodiments, the MART-1 TCR comprises a subunit including a variable region from one of M1-α, M1-β, M2-α and M2-β. Preferably, if a MART-1 TCR comprises a subunit having a variable region from M2-α, it also comprises a subunit having a variable region from M1-β or M2-β. Similarly, if a MART-1 TCR comprises an M2-α subunit, it also preferably comprises an M1-β or an M2-β subunit.

In some embodiments of the invention, the MART-1 TCR comprises an M1-α subunit as described herein, such as the M1-α subunit having the polypeptide sequence of SEQ ID NO: 3. Generally, an M1-α subunit comprises a sequence having at least 70% identity to SEQ ID NO: 3. In other embodiments, the MART-1 TCR comprises a subunit having an M1-α variable region polypeptide sequence as described herein, such as the M1-α variable region having the sequence of SEQ ID NO: 4. Generally, an M1-α variable region comprises a sequence having at least 70% identity to SEQ ID NO: 4.

In some embodiments of the invention, the MART-1 TCR comprises an M1-β subunit as described herein, such as the M1-β subunit having the sequence of SEQ ID NO: 7. Generally, an M1-β subunit comprises a sequence having at least 70% identity to SEQ ID NO: 7. Preferably, the M1-β subunit comprises a sequence having at least 96%, 97%, 98%, 99% or 100% identity to SEQ ID NO: 7. In other embodiments, the MART-1 TCR comprises a subunit having an M1-β variable region polypeptide sequence as described herein, such as the M1-β variable region having the sequence of SEQ ID NO: 8. Generally, an M1-β variable region comprises a sequence having at least 70% identity to SEQ ID NO: 8. Preferably, the M1-β variable region comprises a sequence having at least 96%, 97%, 98%, 99% or 100% identity to SEQ ID NO: 8.

In some embodiments of the invention, the MART-1 TCR comprises an M1-α subunit and an M1-β subunit substantially as described herein.

In some embodiments of the invention, the MART-1 TCR comprises an α subunit comprising an M1-α variable region and a β subunit comprising an M1-β variable region substantially as described herein.

In some embodiments of the invention, a MART-1 TCR comprises an M2-α subunit as described herein, such as the M2-α subunit having the sequence of SEQ ID NO: 11. Generally, an M2-α subunit comprises a sequence having at least 70% identity to SEQ ID NO: 11. In other embodiments, a MART-1 TCR comprises a subunit having an M2-α variable region polypeptide sequence as described herein, such as the M2-α variable region having the sequence of SEQ ID NO: 12. Generally, an M2α variable region comprises a sequence having at least 70% identity to SEQ ID NO: 12.

In some embodiments of the invention, the MART-1 TCR comprises an M2-β subunit as described herein, such as the M2-β subunit having the sequence of SEQ ID NO: 15. Generally, an M2-α subunit comprises a sequence having at least 70% identity to SEQ ID NO: 15. In other embodiments, the MART-1 TCR comprises a subunit having an M2-β variable region polypeptide sequence as described herein. Generally, an M2-β variable region comprises a sequence having at least 70% identity to SEQ ID NO: 16.

In some embodiments of the invention, the MART-1 TCR comprises an M2-α subunit and an M2-β subunit substantially as described herein.

In some embodiments of the invention, the MART-1 TCR comprises an α subunit comprising an M2α variable region and a β subunit comprising an M2-β variable region substantially as described herein.

In some embodiments of the invention, the MART-1 TCR comprises an M1-α subunit and an M2-β subunit substantially as described herein.

In some embodiments of the invention, the MART-1 TCR comprises an α subunit comprising an M1-α variable region and a β subunit comprising an M2-β variable region substantially as described herein.

In some embodiments of the invention, the MART-1 TCR comprises an M2-α subunit and an M1-β subunit substantially as described herein.

In some embodiments of the invention, the MART-1 TCR comprises an α subunit comprising an M2α variable region and a β subunit comprising an M1-β variable region substantially as described herein.

Host cells that are engineered to express a MART-1 TCR are also provided. The cells are preferably T-cells. The T-cells can be engineered by, for example, transduction with one or more lentiviruses encoding an α subunit and a β subunit of a MART-1 TCR. In some embodiments, the T-cell is optionally engineered to express a further genetic sequence such as a suicide or reporter gene. For example, a thymidine kinase gene may be included, such as a sr39tk gene.

In some embodiments of the invention, the T-cells are engineered to express at least one of: a TCR α subunit comprising an M1-α variable region, a TCR β subunit comprising an M1-β variable region and a TCR β subunit comprising an M2-β variable region, wherein the variable regions are substantially as described herein. In other embodiments, the T-cells are engineered to express at least one of: an M1-α subunit, an M1-β subunit and an M2-β subunit, wherein the subunits are substantially as described herein.

In some embodiments of the invention, the T-cells are engineered to express a TCR α subunit comprising an M1-α variable region and a TCR β subunit comprising an M1-β variable region, wherein the variable regions are substantially as described herein. In other embodiments, the T-cells are engineered to express an M1-α subunit and an M1-β subunit, wherein the subunits are substantially as described herein.

In some embodiments of the invention, the T-cells are engineered to express a TCR α subunit comprising an M2α variable region and a TCR β subunit comprising an M2-β variable region, wherein the variable regions are substantially as described herein. In other embodiments, the T-cells are engineered to express an M2-α subunit and an M2-β subunit, wherein the subunits are substantially as described herein.

Vectors are also provided for introducing nucleic acid sequences encoding at least one of: a TCR α subunit comprising a TCR α subunit variable region, a TCR β subunit comprising a TCR β subunit variable region, an α subunit, and a β subunit of a MART-1 TCR into a target cell. The nucleic acid sequences can be introduced into the target cell by, for example, transduction with a lentivirus comprising said sequences. The lentivirus may be prepared from a lentiviral vector comprising the TCR nucleic acid sequences. In some embodiments, the vector further includes a nucleic acid molecule that encodes a suicide gene. The suicide gene can be, for example, a thymidine kinase gene, an *E. coli* cytosine deaminase (CD) gene, an *E. coli* nitroreductase gene, a carboxylesterase gene or a cytochrome P450 gene. In particular embodiments, the suicide gene is an sr39tk sequence, for example, comprising SEQ ID NO: 18. Typically, an sr39tk sequence comprises a sequence having at least 85% identity to SEQ ID NO: 18.

In some embodiments, compositions are provided comprising nucleic acids encoding a MART-1 TCR, subunits of a MART-1 TCR and/or variable regions of MART-1 TCR subunits. The nucleic acids encoding a MART-1 TCR, subunits of a MART-1 TCR and/or variable regions of a MART-1 TCR are substantially as described herein.

The nucleic acids encoding subunits of a MART-1 TCR may comprise a nucleic acid sequence having at least 70% identity to at least one of: an m1-α subunit nucleotide sequence (SEQ ID NO: 1), an m1-β subunit nucleotide sequence (SEQ ID NO: 5), an m2-α subunit nucleotide sequence (SEQ ID NO: 9) and an m2-β subunit nucleotide sequence (SEQ ID NO: 13). In some embodiments, the nucleic acids encoding subunits of a MART-1 TCR comprise at least one of an α or β subunit nucleotide sequence as described herein.

Nucleic acids encoding variable regions of a MART-1 TCR may comprise a sequence having at least 70% identity to at least one of: an m1-α variable region nucleotide sequence (SEQ ID NO: 2), an m1-β variable region nucleotide sequence (SEQ ID NO: 6), an m2-α variable region nucleotide sequence (SEQ ID NO: 10) and an m2-β variable region nucleotide sequence (SEQ ID NO: 14). In some embodiments, the nucleic acids encoding variable regions of a MART-1 TCR comprise at least one of an α or β variable region nucleotide sequence as described herein. The variable regions are preferably provided as part of a nucleic acid encoding one or both of a TCR α or β subunit.

The nucleic acids can be comprised within a vector. In some embodiments, the vector is an expression vector. The expression vector can be used for expression in a eukaryotic cell line (e.g. mammalian, insect or yeast cells) or in prokaryote cells (e.g. *E. coli*) or in both. In some embodiments, the vector is a viral vector. The viral vector is preferably a retroviral vector, more preferably a lentiviral vector. In embodiments of the invention, the nucleic acid is comprised within a lentiviral vector for preparation of lentiviruses that can be used to transduce cells.

In one aspect of the invention, methods of engineering a target cell to express a MART-1 TCR are provided. In some embodiments, methods are provided comprising: providing a population of cells comprising T cells; and contacting the population of cells with one or more recombinant viruses encoding an α and β subunit of a MART-1 TCR. Preferably, the one or more recombinant viruses are lentiviruses.

In some embodiments, the one or more recombinant viruses encode at least one of: a TCR α subunit comprising an M1-α variable region, a TCR β subunit comprising an M1-β variable region and a TCR β subunit comprising an M2-β variable region, wherein the variable regions are substantially as described herein. In some embodiments, the variable regions are encoded by nucleic acid molecules as described herein.

In other embodiments, the one or more recombinant viruses comprise nucleic acid sequences encoding at least one of: an M1-α subunit, an M1-β subunit and an M2-β subunit, wherein the subunits are substantially as described herein.

In some embodiments, the recombinant virus further comprises a suicide or a reporter gene sequence. For example, the recombinant virus can further comprise a thymidine kinase sequence.

In another aspect of the invention, kits are provided to engineer target cells to express a MART-1 TCR. In embodiments of the invention, the kits comprise: a composition encoding an α and β subunit of a MART-1 TCR; and instructions for use of the composition. The composition may be, for example, a recombinant virus, or a viral vector. In some embodiments, the composition comprises one or more sequences encoding TCR subunits comprising at least one of: an M1-α variable region, an M1-β variable region and an M2-β variable region, wherein the variable regions are substantially as described herein. In some embodiments, the variable regions are encoded by nucleic acid molecules as described herein. In other embodiments, the composition comprises one or more sequences encoding at least one of: an M1-α subunit, an M1-β subunit and an M2-β subunit, wherein the subunits are substantially as described herein. In some embodiments, the subunits are encoded by nucleic acid molecules as described herein.

In certain embodiments, the composition further comprises a nucleotide sequence encoding a reporter or a suicide gene. In some embodiments, the nucleotide sequence encodes a thymidine kinase. For example, the nucleotide sequence can comprise an sr39tk sequence. The reporter or suicide gene nucleotide sequence can be included in the same nucleic molecule as the TCR sequences, or it can be encoded by a separate nucleic acid molecule that is included with the kit.

In preferred embodiments, the composition comprises one or more sequences that encode an M1-α variable region and an M1-β variable region. In other preferred embodiments, the composition comprises one or more sequences that encode an M2α variable region and an M2-β variable region. In preferred embodiments, the kits are provided for the treatment of melanoma and include instructions for using the composition.

In addition, methods are provided for treatment of melanoma in a subject. In some embodiments, the methods comprise: providing a population of cells engineered to express a MART-1 T-cell receptor (TCR) to a subject in an amount effective to treat melanoma, wherein the TCR comprises at least one of: an α subunit comprising an M1-α variable region, a β subunit comprising an M1-β variable region and a β subunit comprising an M2-β variable region. In other embodiments, the methods comprise: providing a population of cells engineered to express a MART-1 T-cell receptor (TCR) to a subject in an amount effective to treat melanoma, wherein the TCR comprises at least one of: an M1-α subunit, an M1-β subunit and an M2-β subunit.

In some embodiments of the invention, methods are provided for treatment of melanoma in a subject, the methods comprising: obtaining a sample of cells from a subject; contacting the cells with one or more recombinant viruses encoding at least one of: an M1-α variable region sequence, an M1-β variable region sequence and an M2-β variable region sequence; and re-introducing the cells into the subject. In other embodiments of the invention, methods are provided for treatment of melanoma in a subject, the methods comprising: obtaining a sample of cells from a subject; contacting the cells with one or more recombinant viruses encoding at least one of: an M1-α subunit, an M1-β subunit and an M2-β subunit; and re-introducing the cells into the subject. In some embodiments, the one or more recombinant viruses further comprise an sr39tk sequence.

Effective amounts of administration can be determined by one of skill in the art and can be, for example, amounts of at least $10^4$, $10^5$, $10^6$, $10^7$, $10^8$ or $10^9$ cells per dose. In some embodiments, the cells are provided to the subject in a dose-escalating manner. The population of cells is one that comprises at least one of the following types of cells: cytotoxic T lymphocytes (CTLs), CD8+ T-cells, hematopoetic stem cells (HSCs), and peripheral blood mononuclear cells (PBMCs). In preferred embodiments, the population of cells comprises CD8+ T-cells.

The methods are typically used to generate a desired immune response against melanoma in a patient. The methods can be combined with other therapeutic methods, such as vaccination or immunization. The immunization stimulates the immune response to the target antigen and leads to an even greater degree of efficacy in treating the disease or disorder. The immunization may be repeated multiple times to obtain maximal results.

In some embodiments, treatment methods further comprise providing a MART-1 dendritic cell (DC) vaccine to the patient. In preferred embodiments, the methods further comprise providing a MART-$1_{26-35}$ DC vaccine to the patient. Typically, DCs (which are antigen-presenting cells that are able to induce specific T cell immunity) are harvested from the patient or from a donor. The DCs can then be exposed in vitro to the MART-1 antigen for which T cells are to be generated in the patient, for example, to MART-$1_{26-35}$ peptide sequence (SEQ ID NO: 20). Dendritic cells loaded with the antigen are then injected back into the patient. Immunization may be repeated multiple times if desired. Methods for harvesting, expanding, and administering dendritic cells are well known in the art, for example, as described in Fong et al (Fong et al. 2001. *J Immunol* 166:4254-4259, which is incorporated herein by reference in its entirety). DC vaccines are further described elsewhere, such as in U.S. patent application Ser. No. 11/517,814, filed Sep. 8, 2006 and entitled "METHOD FOR THE GENERATION OF ANTIGEN-SPECIFIC LYMPHOCYTES"; U.S. patent application Ser. No. 11/071,785, filed Mar. 2, 2005 and entitled "ANTIGEN SPECIFIC T CELL THERAPY"; and U.S. patent application Ser. No. 11/446,353, filed Jun. 1, 2006 and entitled "METHOD OF TARGETED GENE DELIVERY USING VIRAL VECTORS," each of which is incorporated herein by reference in its entirety. Typical doses of DCs administered to the patient include at least about 10 million cells.

In some embodiments, the method further comprises providing interleukin to the patient. In preferred embodiments, the interleukin is selected from the following: interleukin-2 (IL-2), interleukin-7 (IL-7), interleukin-15 (IL-15), interleukin-21 (IL-21) and interleukin-23 (IL-23). Typical doses of the interleukin are from about 600,000 to about 720,000 IU/kg delivered intravenously, though lower interleukin doses are also contemplated. In still further embodiments, the method further comprises providing a non-myeloablative chemotherapy regimen to the patient. The chemotherapy conditioning regimen generally includes cyclophosphamide delivered at about 60 mg/kg/day for 2 days intravenously and fludarabine delivered at about 25 mg/m2/day for 5 days. Myelodepleting conditioning regimens for adding total body irradiation (TBI) to the chemotherapy conditioning are also contemplated.

Methods are also provided to activate an engineered CD8+ T-cell that expresses a high-affinity TCR for administration to a patient in need of melanoma treatment. Methods typically comprise obtaining peripheral blood mononuclear cells (PBMCs) from the patient, activating PBMCs with at least one of CD2, CD3 and CD28, isolating CD8+ cytotoxic T lymphocytes (CTLs) from the activated PBMC population, and transducing the isolated CD8+ CTLs with a recombinant virus encoding at least one of the following: an α subunit comprising an M1-α variable region, a β subunit comprising an M1-β variable region and a β subunit comprising an M2-β variable region. In some embodiments, the recombinant virus encodes at least one of the following: an M1-α subunit, an M1-β subunit and an M2-β subunit. Preferably, the virus is a lentivirus. The virus-transduced CD8+ CTLs are typically transferred into a patient, where they efficiently give rise to T cell expressing the high-affinity TCR in vivo.

Typical activating amounts of CD2, CD3, and CD28 are known to one of skill in the art. For example, activating amounts of CD2, CD3, and CD28 magnetic microbeads include, but are not limited to, at least about $2.5 \times 10^6$ nanoparticles per $5 \times 10^6$ peripheral blood mononuclear cells (PBMC), The methods and compositions disclosed herein can be used to prevent, treat or slow the progression of melanoma. For example, the methods may be used to prevent the formation of a melanoma tumor, or reduce or eliminate a melanoma tumor that is already present in a patient Definitions Unless defined otherwise, technical and scientific terms used herein have the same meaning as commonly understood by one of ordinary skill in the art to which this invention belongs. See, e.g. Singleton et al., *Dictionary of Microbiology and Molecular Biology* 2nd ed., J. Wiley & Sons (New York, N.Y. 1994); Sambrook et al., *Molecular Cloning, A Laboratory Manual*, Cold Springs Harbor Press (Cold Springs Harbor, N.Y. 1989). Any methods, devices and materials similar or equivalent to those described herein can be used in the practice of this invention.

As used herein, the terms nucleic acid, polynucleotide and nucleotide are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages.

The terms nucleic acid, polynucleotide and nucleotide also specifically include nucleic acids composed of bases other than the five biologically occurring bases (adenine, guanine, thymine, cytosine and uracil).

As used herein, a nucleic acid molecule is said to be "isolated" when the nucleic acid molecule is substantially separated from contaminant nucleic acid molecules encoding other polypeptides.

"Immunization" refers to the provision of antigen to a host. The antigen is preferably an antigen that is recognized by T cells that have been generated in the host as disclosed herein. In the preferred embodiments, antigen is loaded onto antigen-presenting cells, such as dendritic cells, which are subsequently administered to the recipient. Methods that can be used for immunization are described, for example, in U.S. application Ser. No. 11/446,353, entitled "METHOD OF TARGETED GENE DELIVERY USING VIRAL VECTORS," filed on Jun. 1, 2006; and U.S. application Ser. No. 11/781,865, entitled "TARGETED GENE DELIVERY FOR DENDRITIC CELL VACCINATION," filed on Jul. 23, 2007, each of which is incorporated herein by reference in its entirety. Other methods of immunization are well known in the art and may be used.

The term "immunological" or "immune" response is the development of a beneficial humoral (antibody mediated) and/or a cellular (mediated by antigen-specific T cells or their secretion products) response directed against a melanoma antigen, such as, for example, MART-1, in a recipient patient. Such a response can be an active response induced by administration of immunogen or a passive response induced by administration of antibody or primed T-cells. A cellular immune response is elicited by the presentation of polypeptide epitopes in association with a MART-1 antigen to activate MART-1-specific $CD4^+$ T helper cells and/or $CD8^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays ($CD4^+$ T cells) or CTL (cytotoxic T lymphocyte) assays (Burke et al., *J. Inf. Dis.* 170, 1110-19 (1994)), by antigen-dependent killing (cytotoxic T lymphocyte assay, Tigges et al., *J. Immunol.* 156, 3901-3910) or by cytokine secretion. The relative contributions of humoral and cellular responses to the protective or therapeutic effect of an immunogen can be distinguished by separately isolating IgG and T-cells from an immunized syngeneic animal and measuring protective or therapeutic effect in a second subject.

An "immunogenic agent" or "immunogen" is capable of inducing an immunological response against itself on administration to a patient, optionally in conjunction with an adjuvant.

The term "adjuvant" refers to a compound that when administered in conjunction with an antigen augments, enhances, and/or boosts the immune response to a MART-1 antigen, but when administered alone does not generate an immune response to the antigen. An adjuvant can be administered with an immunogen, or can be administered before, concurrent with or after administration. Adjuvants can enhance an immune response by several mechanisms including lymphocyte recruitment, stimulation of B and/or T cells, and stimulation of macrophages The term "antibody" is used in the broadest sense and specifically covers human, non-human (e.g. murine) and humanized monoclonal antibodies (including full length monoclonal antibodies), polyclonal antibodies, multi-specific antibodies (e.g., bispecific antibodies), and antibody fragments so long as they exhibit the desired biological activity. In some embodiments, antibodies to the MART-1 TCRs described herein, or one or more subunits thereof, are provided.

An "antigen" is any molecule that is capable of generating an immune response. In some embodiments, the antigen is capable of binding to a T cell receptor. A preferred antigen is the MART-1/Melan-A antigen, which is capable of initiating an immune response upon binding to a T cell receptor specific for the antigen that is expressed in an immune cell. An "immune response" is any biological activity that is attributable to the binding of an antigen to an immune cell, preferably to a T cell receptor on an immune cell.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, X-ray crystallography and 2-dimensional nuclear magnetic resonance. See, e.g., *Epitope Mapping Protocols in Methods in Molecular Biology*, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize a particular epitope can be identified by well-known assays, such as in vitro assays that measure antigen-dependent proliferation, as determined by $^3$H-thymidine incorporation by primed T cells in response to an epitope (see Burke, supra; Tigges, supra)

As used herein, the term "T cell receptor" includes a complex of polypeptides comprising at least a T cell receptor ca subunit and a T cell receptor β subunit. T cell receptors ("TCRs") are able to bind antigen when expressed on the surface of a cell, such as a T lymphocyte. The α and β chains, or subunits, form a dimer that is independently capable of antigen binding. The α and β subunits typically comprise a constant domain and a variable domain and may be native, full-length polypeptides, or may be modified in some way, provided that the T cell receptor retains the ability to bind antigen. For example, the α and β subunits may be amino acid sequence variants, including substitution, addition and deletion mutants. They may also be chimeric subunits that comprise, for example, the variable regions from one organism and the constant regions from a different organism.

A functional MART-1 TCR is one that binds MART-1 antigen with $K_D$ of at least 4 nM and/or mediates an immune response against MART-1, for example using the ELISA assay as described in Example 3. For example, a MART-1 TCR can be one that produces an IFN-γ concentration of at least 50 pg/mL in vitro upon stimulation by MART-1 loaded T2 cells.

"Target cells" are any cells that are capable of expressing a T-cell receptor (TCR) on their surface or that can mature into cells that express a TCR on their surface. Preferably, target cells are capable of maturing into immune cells, such as lymphocytes. Target cells include, without limitation, cytotoxic T lymphocytes (CTLs), such as CD8+ CTLs. Target cells can also include, without limitation, stem cells, such as hematopoietic stem cells.

As used herein, a cell exhibits "MART-1 antigen specificity" if it is primarily responsive to a MART-1 antigen.

The term "mammal" is defined as an individual belonging to the class Mammalia and includes, without limitation, humans, domestic and farm animals, and zoo, sports, and pet animals, such as sheep, dogs, horses, cats, mice and cows.

A "subject" or "patient" is any animal, preferably a mammal, that is in need of treatment.

As used herein, "treatment" is a clinical intervention that may be therapeutic or prophylactic. In therapeutic applications, pharmaceutical compositions or medicants are administered to a patient suspected of, or already suffering from melanoma in an amount sufficient to cure, or at least partially arrest, the symptoms of the disease and its complications. In prophylactic applications, pharmaceutical compositions or medicants are administered to a patient susceptible to, or otherwise at risk of, melanoma in an amount sufficient to eliminate or reduce the risk or delay the outset of the disease. An amount adequate to accomplish this is defined as a therapeutically- or pharmaceutically-effective dose. Such an amount can be administered as a single dosage or can be administered according to a regimen, whereby it is effective. The amount can cure melanoma but, typically, is administered in order to ameliorate the symptoms of the disease, or to effect prophylaxis of the disease from developing. In both therapeutic and prophylactic regimes, agents are usually administered in several dosages until a sufficient immune response has been achieved. Typically, the immune response is monitored and repeated dosages are given if the immune response starts to fade. "Treatment" need not completely eliminate the disease, nor need it completely prevent a subject from becoming ill with the disease or disorder.

"Tumor," as used herein, refers to all neoplastic melanoma cell growth and proliferation, whether malignant or benign, and all pre-cancerous and cancerous melanoma cells and tissues.

A "vector" is a nucleic acid molecule that is capable of transporting another nucleic acid. Vectors may be, for example, plasmids, cosmids or phage. An "expression vector" is a vector that is capable of directing the expression of a protein encoded by one or more genes carried by the vector when it is present in the appropriate environment.

The term "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and a ribosome binding sites. Regulatory elements that are used in eukaryotic cells may include, without limitation, promoters, enhancers, splicing signals and polyadenylation signals.

The term "transfection" refers to the introduction of a nucleic acid into a host cell.

"Retroviruses" are viruses having an RNA genome.

"Lentivirus" refers to a genus of retroviruses that are capable of infecting dividing and non-dividing cells. Several examples of lentiviruses include HIV (human immunodeficiency virus: including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates.

A lentiviral genome is generally organized into a 5' long terminal repeat (LTR), the gag gene, the pol gene, the env gene, the accessory genes (nef, vif, vpr, vpu) and a 3' LTR. The viral LTR is divided into three regions called U3, R and U5. The U3 region contains the enhancer and promoter elements. The U5 region contains the polyadenylation signals. The R (repeat) region separates the U3 and U5 regions and transcribed sequences of the R region appear at both the 5' and 3' ends of the viral RNA. See, for example, *RNA Viruses: A Practical Approach* (Alan J. Cann, Ed., Oxford University Press, (2000)); O Narayan and Clements. 1989. *J. Gen. Virology* 70:1617-1639 (1989); Fields et al. *Fundamental Virology* Raven Press. (1990); Miyoshi H, Blomer U, Takahashi M, Gage F H, Verma I M. 1998. *J. Virol.* 72(10):8150-7; and U.S. Pat. No. 6,013,516.

"Gammaretrovirus" refers to a genus of the retroviridae family. Exemplary gammaretroviruses include, but are not limited to, mouse stem cell virus, murine leukemia virus, feline leukemia virus, feline sarcoma virus, and avian reticuloendotheliosis viruses.

A "hybrid virus" as used herein refers to a virus having components from one or more other viral vectors, including element from non-retroviral vectors, for example, adenoviral-retroviral hybrids. As used herein hybrid vectors having a retroviral component are to be considered within the scope of the retroviruses.

"Virion," "viral particle" and "retroviral particle" are used herein to refer to a single virus comprising an RNA genome, pol gene derived proteins, gag gene derived proteins and a lipid bilayer displaying an envelope (glyco)protein. The RNA genome is usually a recombinant RNA genome and thus may contain an RNA sequence that is exogenous to the native viral genome. The RNA genome may also comprise a defective endogenous viral sequence.

"Transformation," as defined herein, describes a process by which exogenous DNA enters a target cell. Transformation may rely on any known method for the insertion of foreign nucleic acid sequences into a prokaryotic or eukaryotic host cell and may include, but is not limited to, viral infection, electroporation, heat shock, lipofection, and particle bombardment. "Transformed" cells include stably transformed cells in which the inserted nucleic acid is capable of replication either as an autonomously replicating plasmid or as part of the host chromosome. Also included are cells that transiently express a gene of interest.

The term "transgenic" is used herein to describe the property of harboring a transgene. For instance, a "transgenic organism" is any animal, including mammals, fish, birds and amphibians, in which one or more of the cells of the animal contain nucleic acid introduced by way of human intervention. In the typical transgenic animal, the transgene causes expression of a recombinant protein.

A "functional relationship" and "operably linked" mean, with respect to the gene of interest, that the gene is in the correct location and orientation with respect to the promoter and/or enhancer that expression of the gene will be affected when the promoter and/or enhancer is contacted with the appropriate molecules.

Nucleic Acid Embodiments of the Present Invention

Embodiments of the invention include nucleic acid molecules that encode one or more subunits of T-cell receptors (TCRs) that recognize MART-1. For example, isolated nucleic acid molecules are provided that encode polypeptides comprising the amino acid sequences of SEQ ID NOs: 3, 4, 7, 8, 11, 12, 15 and 16. The nucleic acid molecules include nucleic acid molecules encoding m1-α variable region polypeptide sequences, m1-α subunit polypeptide sequences, m1-β variable region polypeptide sequences, m1-β subunit polypeptide sequences, m2-β variable region polypeptide sequences and m2-β subunit polypeptide sequences.

Generally, an m1-α variable region nucleic acid sequence comprises a sequence having at least 70% identity to SEQ ID NO: 2. In some embodiments, the m1-α variable region sequence comprises a sequence having at least 71%, 72%, 73%, 74%, 75%, 76%, 77%, 78%, 79%, 80%, 81%, 82%, 83%, 84% or 85% identity to SEQ ID NO: 2. In other embodiments, the m1-α variable region sequence comprises a sequence having at least 86%, 87%, 88%, 89%, 90%, 91%, 92%, 93%, 94%, 95%, 96%, 97%, 98%, 99% or 100% identity to SEQ ID NO: 2. In some embodiments, the m1-α variable region sequence comprises SEQ ID NO: 2. The variable region nucleic acid sequence is typically part of an isolated nucleic acid encoding an M1-α subunit.

Generally, an m1-α subunit sequence is an isolated nucleic acid sequence comprises a sequence having at least 70% identity to SEQ ID NO: 1. In some embodiments, the m1-α subunit sequence comprises a sequence having at least 71%, 72%, 73%, 74%, 75%, 76%, 77%, 78%, 79%, 80%, 81%, 82%, 83%, 84% or 85% identity to SEQ ID NO: 1. In other embodiments, the m1-α subunit sequence comprises a sequence having at least 86%, 87%, 88%, 89%, 90%, 91%, 92%, 93%, 94%, 95%, 96%, 97%, 98%, 99% or 100% identity to SEQ ID NO: 1. In some embodiments, an m1-α subunit sequence comprises SEQ ID NO: 1.

Generally, an m1-β variable region sequence comprises a nucleic acid sequence having at least 70% identity to SEQ ID NO: 6. In some embodiments, the m1-β variable region sequence comprises a sequence having at least 71%, 72%, 73%, 74%, 75%, 76%, 77%, 78%, 79%, 80%, 81%, 82%, 83%, 84% or 85% identity to SEQ ID NO: 6. In other embodiments, the m1-β variable region sequence comprises a sequence having at least 86%, 87%, 88%, 89%, 90%, 91%, 92%, 93%, 94%, 95%, 96%, 97%, 98%, 99% or 100% identity to SEQ ID NO: 6. Preferably, the m1-β variable region sequence comprises a sequence having at least 96%, 97%, 98%, 99% or 100% identity to SEQ ID NO: 6. In some embodiments, the m1-β variable region sequence comprises SEQ ID NO: 6. The variable region nucleic acid sequence is typically part of an isolated nucleic acid encoding an M1-β subunit.

Generally, an m1-β subunit sequence is an isolated nucleic acid sequence comprising a sequence having at least 70% identity to SEQ ID NO: 5. In some embodiments, the m1-β subunit sequence comprises a sequence having at least 71%, 72%, 73%, 74%, 75%, 76%, 77%, 78%, 79%, 80%, 81%, 82%, 83%, 84% or 85% identity to SEQ ID NO: 5. In other embodiments, the m1-β subunit sequence comprises a sequence having at least 86%, 87%, 88%, 89%, 90%, 91%, 92%, 93%, 94%, 95%, 96%, 97%, 98%, 99% or 100% identity to SEQ ID NO: 5. Preferably, the m1-β subunit sequence comprises a sequence having at least 96%, 97%, 98%, 99% or 100% identity to SEQ ID NO: 5. In some embodiments, the m1-β subunit sequence comprises SEQ ID NO: 5.

Generally, an m2-α variable region sequence comprises a sequence having at least 70% identity to SEQ ID NO: 10. In some embodiments, the m2-α variable region sequence comprises a sequence having at least 71%, 72%, 73%, 74%, 75%, 76%, 77%, 78%, 79%, 80%, 81%, 82%, 83%, 84% or 85% identity to SEQ ID NO: 10. In other embodiments, the m2-α variable region sequence comprises a sequence having at least 86%, 87%, 88%, 89%, 90%, 91%, 92%, 93%, 94%, 95%, 96%, 97%, 98%, 99% or 100% identity to SEQ ID NO: 10. In some embodiments, the m2-α variable region sequence comprises SEQ ID NO: 10. The variable region nucleic acid sequence is typically part of an isolated nucleic acid encoding an M2-α subunit.

Generally, an m2-α subunit sequence is an isolated nucleic acid sequence comprising a sequence having at least 70% identity to SEQ ID NO: 9. In some embodiments, the m2-α subunit sequence comprises a sequence having at least 71%, 72%, 73%, 74%, 75%, 76%, 77%, 78%, 79%, 80%, 81%, 82%, 83%, 84% or 85% identity to SEQ ID NO: 9. In other embodiments, the m2-α subunit sequence comprises a sequence having at least 86%, 87%, 88%, 89%, 90%, 91%, 92%, 93%, 94%, 95%, 96%, 97%, 98%, 99% or 100% identity to SEQ ID NO: 9. In some embodiments, the m2-α subunit sequence comprises SEQ ID NO: 9.

Generally, an m2-β variable region sequence comprises a sequence having at least 70% identity to SEQ ID NO: 14. In some embodiments, the m2-β variable region sequence comprises a sequence having at least 71%, 72%, 73%, 74%, 75%, 76%, 77%, 78%, 79%, 80%, 81%, 82%, 83%, 84% or 85% identity to SEQ ID NO: 14. In other embodiments, the m2-β variable region sequence comprises a sequence having at least 86%, 87%, 88%, 89%, 90%, 91%, 92%, 93%, 94%, 95%, 96%, 97%, 98%, 99% or 100% identity to SEQ ID NO: 14. In some embodiments, the m2-β variable region sequence comprises SEQ ID NO: 14. The variable region nucleic acid sequence is typically part of an isolated nucleic acid encoding an M2-β subunit.

Generally, an m2-β subunit sequence is an isolated nucleic acid sequence comprising a sequence having at least 70% identity to SEQ ID NO: 13. In some embodiments, the m2-β subunit sequence comprises a sequence having at least 71%, 72%, 73%, 74%, 75%, 76%, 77%, 78%, 79%, 80%, 81%, 82%, 83%, 84% or 85% identity to SEQ ID NO: 13. In other embodiments, the m2-β subunit sequence comprises a sequence having at least 86%, 87%, 88%, 89%, 90%, 91%, 92%, 93%, 94%, 95%, 96%, 97%, 98%, 99% or 100% identity to SEQ ID NO: 13. In some embodiments, the m2-β subunit sequence comprises SEQ ID NO: 13.

The nucleic acid molecule can be a derivative, homolog, analog or mimetic thereof comprising a nucleotide sequence encoding, or a nucleotide sequence complementary to a sequence encoding an expression product wherein said nucleotide sequence includes at least one of: an m1-α variable region sequence, an m1-β variable region sequence and an m2-β variable region sequence, or having at least about 70% similarity to all or part of an m1-α variable region sequence, an m1-β variable region sequence, and an m2-β variable region sequence, or a nucleotide sequence capable of hybridizing under high stringency conditions to an m1-α variable region sequence, an m1-β variable region sequence and an m2-β variable region sequence.

In some embodiments, the nucleic acid molecule can be a derivative, homolog, analog or mimetic thereof comprising a nucleotide sequence encoding, or a nucleotide sequence complementary to a sequence encoding an expression product wherein said nucleotide sequence includes at least one of: an m1-α subunit sequence, an m1-β subunit sequence and an m2-β subunit sequence, or having at least about 70% similarity to all or part of an m1-α subunit sequence, an m1-β subunit sequence and an m2-β subunit sequence, or a nucleotide sequence capable of hybridizing under high stringency conditions to an m1-α subunit sequence, an m1-β subunit sequence or an m2-β subunit sequence.

Higher nucleic acid sequence similarities are also contemplated by the present invention such as greater than about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or above.

The term "similarity" as used herein includes exact identity between compared sequences at the nucleotide level. Where there is non-identity at the nucleotide level, "similarity" includes differences between sequences which may encode different amino acids that are nevertheless related to each other at the structural, functional, biochemical and/or conformational levels. In a particularly preferred embodiment, nucleotide sequence comparisons are made at the level of identity rather than similarity.

The terms "sequence similarity" and "sequence identity" as used herein refers to the extent that sequences are identical or functionally or structurally similar on a nucleotide-by-nucleotide basis over a window of comparison. Thus, a "percentage of sequence identity", for example, can be calculated by comparing two optimally aligned sequences over the window of comparison, determining the number of positions at which the identical nucleic acid base (e.g. A, T, C, G, I) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

The nucleotide sequence or amino acid sequence embodiments of the present invention may correspond to exactly the same sequence of the naturally occurring gene (or corresponding cDNA) or protein or other expression product or may carry one or more nucleotide or amino acid substitutions, additions and/or deletions. The nucleotide sequences included within an m1-α variable region sequence, an m1-α subunit sequence, an m1-β variable region sequence, an m1-β subunit sequence, an m2-β variable region sequence and an m2-β subunit sequence correspond to embodiments of particular TCR α and β genes, and the corresponding expression products are embodiments of particular TCR α and β polypeptides of the present invention. Reference herein to an m1-α variable region sequence, an m1-α subunit sequence, an m1-β variable region sequence, an m1-β subunit sequence, an m2-β variable region sequence and an m2-β subunit sequence includes, where appropriate, reference to the genomic gene or cDNA as well as any naturally occurring or induced derivatives. Apart from the substitutions, deletions and/or additions to the nucleotide sequence, embodiments of the present invention further encompasses mutants, fragments, parts and portions of the nucleotide sequence corresponding to those containing an m1-α variable region sequence, an m1-α subunit sequence, an m1-β variable region sequence, an m1-β subunit sequence, an m2-β variable region sequence or an m2-β subunit sequence, wherein expression of the nucleotide sequence can form part of a functional MART-1 TCR that is able to recognize and bind MART-1 antigen, as described in Example 5, or is able to stimulate an immune response to MART-1 antigen, as described in Example 3.

A homolog is considered to be a gene from another animal species which has the same or greater than 70% similarity to one of the following: an m1-α variable region sequence, an m1-α subunit sequence, an m1-β variable region sequence, an m1-β subunit sequence, an m2-β variable region sequence and an m2-β subunit sequence, and/or which has a similar function. The above-mentioned genes are exemplified herein from *H. sapiens*. The present invention extends, however, to the homologous gene, as determined by nucleotide sequence and/or function, from humans, primates (lower and higher primates), livestock animals (e.g. cows, sheep, pigs, horses, donkeys), laboratory test animals (e.g. mice, guinea pigs, hamsters, rabbits), companion animals (e.g. cats, dogs) and captured wild animals (e.g. rodents, foxes, deer, kangaroos). Homologs may also be present in microorganisms and *C. elegans*.

The nucleic acid molecule may be part of a vector, such as an expression vector capable of expression in a prokaryotic cell (e.g. *E. coli*) or a eukaryotic cell (e.g. yeast cells, fungal cells, insect cells, mammalian cells or plant cells). The nucleic acid molecule may be ligated or fused or otherwise associated with a nucleic acid molecule encoding another entity such as, for example, a signal peptide. It may also comprise additional nucleotide sequence information fused, linked or otherwise associated with it either at the 3' or 5' terminal portions or at both the 3' and 5' terminal portions.

The derivatives of the nucleic acid molecule of the present invention include variants of an m1-α variable region sequence, an m1-α subunit sequence, an m1-β variable region sequence, an m1-β subunit sequence, an m2-β variable region sequence and an m2-β subunit sequence that encode a functional TCR (as described in Example 3) or that recognizes and binds MART-1 (as described in Example 5). Derivatives include fragments, parts, portions, mutants, variants and mimetics from natural, synthetic or recombinant sources including fusion nucleic acid molecules, and they may be derived from insertion, deletion or substitution of nucleotides. In preferred embodiments, variants include those sequences that encode amino acid sequences with at least 70% sequence similarity to an m1-α variable region sequence, an m1-α subunit sequence, an m1-β variable region sequence, an m1-β subunit sequence, an m2-β variable region sequence or an m2-β subunit sequence.

Polypeptide Embodiments of the Present Invention

"Peptide" generally refers to a short chain of amino acids linked by peptide bonds. Typically peptides comprise amino acid chains of about 2-100, more typically about 4-50, and most commonly about 6-20 amino acids. "Polypeptide" generally refers to individual straight or branched chain sequences of amino acids that are typically longer than peptides. "Polypeptides" usually comprise at least about 100 to about 1000 amino acids in length, more typically at least about 150 to about 600 amino acids, and frequently at least about 200 to about 500 amino acids. "Proteins" include single polypeptides as well as complexes of multiple polypeptide chains, which may be the same or different. Multiple chains in a protein may be characterized by secondary, tertiary and quaternary structure as well as the primary amino acid sequence structure; may be held together, for example, by disulfide bonds; and may include post-synthetic modifications such as, without limitation, glycosylation, phosphorylation, truncations or other processing. For example, a wild-type T-cell receptor (TCR) is composed of eight different subunits organized in dimers, including the TCR α and β chains (See FIG. 1) that are disulfide-bonded to each other. The TCR α and β chains are each further characterized as having distal variable regions (Vα and Vβ) and proximal constant regions (Cα and Cβ) that are glycosylated at specific sites. Furthermore, proteins may include additional components such as associated metals (e.g., iron, copper and sulfur), or other moieties. The definitions of peptides, polypeptides and proteins include, without limitation, biologically active and inactive forms; denatured and native forms; as well as variant, modified, truncated, hybrid, and chimeric forms thereof.

The M1-α polypeptide subunit can comprise an M1-α variable region polypeptide sequence. Generally, an M1-α variable region comprises a sequence having at least 70% identity to SEQ ID NO: 4. In some embodiments, the M1-α variable region comprises a sequence having at least 71%, 72%, 73%, 74%, 75%, 76%, 77%, 78%, 79%, 80%, 81%, 82%, 83%, 84% or 85% identity to SEQ ID NO: 4. In other embodiments, the M1α variable region comprises a sequence having at least 86%, 87%, 88%, 89%, 90%, 91%, 92%, 93%, 94%, 95%, 96%, 97%, 98%, 99% or 100% identity to SEQ ID NO: 4. In some embodiments, the M1-α variable region comprises SEQ ID NO: 4.

In some embodiments, the M1-α polypeptide subunit can comprise a sequence having at least 70% identity to SEQ ID NO: 3. In some embodiments, the M1-α subunit comprises a sequence having at least 71%, 72%, 73%, 74%, 75%, 76%, 77%, 78%, 79%, 80%, 81%, 82%, 83%, 84% or 85% identity to SEQ ID NO: 3. In other embodiments, the M1-α subunit comprises a sequence having at least 86%, 87%, 88%, 89%, 90%, 91%, 92%, 93%, 94%, 95%, 96%, 97%, 98%, 99% or 100% identity to SEQ ID NO: 3. In some embodiments, the M1-α polypeptide sequence comprises SEQ ID NO: 3.

The M1-β polypeptide subunit can comprise an M1-β variable region polypeptide sequence. Generally, an M1-β variable region comprises a sequence having at least 70% identity to SEQ ID NO: 8. In some embodiments, the M1-β variable region comprises a sequence having at least 71%, 72%, 73%, 74%, 75%, 76%, 77%, 78%, 79%, 80%, 81%, 82%, 83%, 84% or 85% identity to SEQ ID NO: 8. In other embodiments, the M1-β variable region comprises a sequence having at least 86%, 87%, 88%, 89%, 90%, 91%, 92%, 93%, 94%, 95%, 96%, 97%, 98%, 99% or 100% identity to SEQ ID NO: 8. Preferably, the M1-β variable region comprises a sequence having at least 96%, 97%, 98%, 99% or 100% identity to SEQ ID NO: 8. In some embodiments, the M1-β variable region comprises SEQ ID NO: 8.

In some embodiments, the M1-β polypeptide subunit can comprise a sequence having at least 70% identity to SEQ ID NO: 7. In some embodiments, the M1-β subunit comprises a sequence having at least 71%, 72%, 73%, 74%, 75%, 76%, 77%, 78%, 79%, 80%, 81%, 82%, 83%, 84% or 85% identity to SEQ ID NO: 7. In other embodiments, the M1-β subunit comprises a sequence having at least 86%, 87%, 88%, 89%, 90%, 91%, 92%, 93%, 94%, 95%, 96%, 97%, 98%, 99% or 100% identity to SEQ ID NO: 7. Preferably, the M1-β subunit comprises a sequence having at least 96%, 97%, 98%, 99% or 100% identity to SEQ ID NO: 7. In some embodiments, the M1-β polypeptide sequence comprises SEQ ID NO: 7.

The M2α polypeptide subunit can comprise an M2α variable region polypeptide sequence. Generally, an M2α variable region comprises a sequence having at least 70% identity to SEQ ID NO: 12. In some embodiments, the M2-α variable region comprises a sequence having at least 71%, 72%, 73%, 74%, 75%, 76%, 77%, 78%, 79%, 80%, 81%, 82%, 83%, 84% or 85% identity to SEQ ID NO: 12. In other embodiments, the M2-α variable region comprises a sequence having at least 86%, 87%, 88%, 89%, 90%, 91%, 92%, 93%, 94%, 95%, 96%, 97%, 98%, 99% or 100% identity to SEQ ID NO: 12. In some embodiments, the M2α variable region comprises SEQ ID NO: 12.

In some embodiments of the invention, the M2-α subunit can comprise a sequence having at least 70% identity to SEQ ID NO: 1. In some embodiments, the M2-α subunit comprises a sequence having at least 71%, 72%, 73%, 74%, 75%, 76%, 77%, 78%, 79%, 80%, 81%, 82%, 83%, 84% or 85% identity to SEQ ID NO: 1. In other embodiments, the M2-α subunit comprises a sequence having at least 86%, 87%, 88%, 89%, 90%, 91%, 92%, 93%, 94%, 95%, 96%, 97%, 98%, 99% or 100% identity to SEQ ID NO: 11. In some embodiments, the M2-α polypeptide sequence comprises SEQ ID NO: 11.

The M2-β subunit can comprise an M2-β variable region polypeptide sequence. Generally, an M2-β variable region comprises a sequence having at least 70% identity to SEQ ID NO: 16. In some embodiments, the M2-β variable region comprises a sequence having at least 71%, 72%, 73%, 74%, 75%, 76%, 77%, 78%, 79%, 80%, 81%, 82%, 83%, 84% or 85% identity to SEQ ID NO: 16. In other embodiments, the M2-β variable region comprises a sequence having at least 86%, 87%, 88%, 89%, 90%, 91%, 92%, 93%, 94%, 95%, 96%, 97%, 98%, 99% or 100% identity to SEQ ID NO: 16. In some embodiments, the M2-β variable region comprises SEQ ID NO: 16.

In some embodiments of the invention, the M2-β subunit can comprise a sequence having at least 70% identity to SEQ ID NO: 15. In some embodiments, the M2-β subunit comprises a sequence having at least 71%, 72%, 73%, 74%, 75%, 76%, 77%, 78%, 79%, 80%, 81%, 82%, 83%, 84% or 85% identity to SEQ ID NO: 15. In other embodiments, the M2-β subunit comprises a sequence having at least 86%, 87%, 88%, 89%, 90%, 91%, 92%, 93%, 94%, 95%, 96%, 97%, 98%, 99% or 100% identity to SEQ ID NO: 15. In some embodiments, the M2-β polypeptide sequence comprises SEQ ID NO: 15.

In embodiments of the invention, the polypeptides comprising at least one of: an M1-α variable region sequence, an M1-β variable region sequence and an M2-β variable region sequence, are encoded by nucleic acid molecules as described herein, or by derivatives, homologs or analogs thereof, or by nucleotide sequences that are capable of hybridizing to the nucleic acid molecules.

In embodiments of the invention, the polypeptides comprising at least one of: an M1-α subunit sequence, an M1-β subunit sequence and an M2-β subunit sequence, are encoded by nucleic acid molecules as described herein, or by derivatives, homologs or analogs thereof, or by nucleotide sequences that are capable of hybridizing to the nucleic acid molecules.

"Variants" include biologically active polypeptides having an amino acid sequence which differs from the polypeptide sequences in an M1-α variable region, an M1-α subunit, an M1-β variable region, an M1-β subunit, an M2-β variable region or an M2-β subunit as described herein. For example, in embodiments of the invention, a MART-1 TCR comprises at least one of: an M1-α variable region, an M1-β variable region and an M2-β variable region, or derivatives, homologs or analogs thereof, or variants having at least about 70% similarity to an M1-α variable region, an M1-β variable region or an M2-β variable region, is contemplated, wherein the TCR recognizes MART-1 antigen. In other embodiments, a MART-1 TCR comprises at least one of: an M1-α subunit polypeptide, an M1-β subunit polypeptide and an M2-β subunit polypeptide, or derivatives, homologs or analogs thereof, or variants having at least about 70% similarity to an M1-α subunit polypeptide, an M1-β subunit polypeptide or an M2-β subunit polypeptide wherein the TCR recognizes MART-1 antigen.

Variants, derivatives, homologs or analogs as described herein are considered biologically active when they can form part or all of an α or β subunit in a functional MART-1 TCR, wherein a functional MART-1 TCR is substantially as described herein, for example, by having specific affinity for MART-1, as described in Example 5, or by being able to stimulate a MART-1 specific immune response, as described in Example 3.

Without limiting the theory or mode of action of the present invention, the expression of a TCR comprising at least one of: an M1-α variable region, an M1-β variable region and an M2-β variable region, or any derivatives, homologs, analogs or variants thereof, in a T-cell can be considered for treatment of melanoma in a subject. In some embodiments, the expression of a TCR comprising at least one of: an M1-α subunit, an M1-β subunit and an M2-β subunit, or any derivatives, homologs, analogs or variants thereof, in a T-cell can be considered for treatment of melanoma in a subject.

Modulation of expression of sequences containing an m1-α variable region sequence, an m1-α subunit sequence, an m1-β variable region sequence, an m1-β subunit sequence, an m2-β variable region sequence or an m2-β subunit sequence, can be useful in the treatment or prophylaxis of tumors and cancers such as those associated with melanoma.

Vectors

Vectors such as, for example, plasmids, cosmids or phage vectors are contemplated. An "expression vector" is a vector that is capable of directing the expression of a protein encoded by one or more genes carried by the vector when it is present in the appropriate environment.

Vectors that provide for transient expression in microbial or mammalian cells may be used. Transient expression involves the use of an expression vector that is able to replicate efficiently in a host cell, such that the host cell accumulates many copies of the expression vector and, in turn, synthesizes high levels of a the polypeptide encoded by the antigen-specific polynucleotide in the expression vector. See Sambrook et al., supra, pp. 16.17-16.22.

Mammalian expression vectors typically also contain sequences necessary for the termination of transcription and for stabilizing the mRNA. These sequences are often found in the 5' and, occasionally 3', untranslated regions of eukaryotic or viral DNAs or cDNAs and are well known in the art.

In some embodiments, for analysis to confirm correct sequences in plasmids constructed, vectors may be replicated in *E. coli*, purified, and analyzed by restriction endonuclease digestion, and/or sequenced by conventional methods.

Generation of the vector(s) can be accomplished using any suitable genetic engineering techniques known in the art, including, without limitation, the standard techniques of restriction endonuclease digestion, ligation, transformation, plasmid purification, and DNA sequencing, for example as described in Sambrook et al. (1989. Molecular Cloning: A Laboratory Manual. Cold Spring Harbor Laboratory Press, N.Y.), Coffin et al. (Retroviruses. Cold Spring Harbor Laboratory Press, N.Y. (1997)) and "RNA Viruses: A Practical Approach" (Alan J. Cann, Ed., Oxford University Press, (2000), each of the foregoing which is incorporated herein by reference in its entirety.

Transformation of mammalian cells with vectors of the present invention is accomplished by well-known methods, and the method to be used is not limited in any way. A number of delivery systems are known in the art, including for example, electroporation, lipid-based delivery systems including liposomes, delivery of "naked" DNA, and delivery using polycyclodextrin compounds, such as those described in Schatzlein A G. (2001. Non-Viral Vectors in Cancer Gene Therapy: Principles and Progresses. *Anticancer Drugs*, which is incorporated herein by reference in its entirety). Cationic lipid or salt treatment methods are typically employed, see, for example, Graham et al. (1973. *Virol.* 52:456; Wigler et al. (1979. *Proc. Natl. Acad. Sci. USA* 76:1373-76), each of the foregoing which is incorporated herein by reference in its entirety. The calcium phosphate precipitation method is preferred. However, other methods for introducing the vector into cells may also be used, including nuclear microinjection and bacterial protoplast fusion.

The vector(s) may incorporate sequences from the genome of any known organism. The sequences may be incorporated in their native form or may be modified in any way. For example, the sequences may comprise insertions, deletions or substitutions.

Expression control elements that may be used for regulating the expression of the components are known in the art and include, but are not limited to, inducible promoters, constitutive promoters, secretion signals, enhancers and other regulatory elements.

In one embodiment, a vector can include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

The vector(s) may include one or more genes for selectable markers that are effective in a eukaryotic cell, such as a gene for a drug resistance selection marker. This gene encodes a factor necessary for the survival or growth of transformed host cells grown in a selective culture medium. Host cells not transformed with the vector containing the selection gene will not survive in the culture medium. Typical selection genes encode proteins that confer resistance to antibiotics or other toxins, e.g. ampicillin, neomycin, methotrexate, or tetracycline, complement auxotrophic deficiencies, or supply critical nutrients withheld from the media. The selectable marker can optionally be present on a separate plasmid and introduced by co-transfection.

In some embodiments, one or more vectors are prepared containing at least one of: an m1-α variable region nucleotide sequence, an m1-β variable region nucleotide sequence and an m2-β variable region nucleotide sequence, as well as any additional elements substantially as described herein. In other embodiments, one or more vectors are prepared containing at least one of: an m1-α subunit nucleotide sequence, an m1-β subunit nucleotide sequence and an m2-β subunit nucleotide sequence, as well as any additional elements substantially as described herein.

Vectors and Packaging Cells for Production of Recombinant Viruses

In some embodiments, vectors can be used to introduce polynucleotide sequences that encode all or part of a functional MART-1 TCR into a packaging cell line for the preparation of a recombinant virus. In addition to the elements as described herein, the vectors can contain polynucleotide sequences encoding the various components of the recombinant virus and at least one of: an M1-α variable region, an M1-β variable region and an M2-β variable region, as well as any components necessary for the production of the virus that are not provided by the packaging cell line. In other embodiments, in addition to the elements as described herein, the vectors can contain polynucleotide sequences encoding the various components of the recombinant virus and at least one of: an M1-α subunit, an M1-β subunit and an M2-β subunit, as well as any components necessary for the production of the virus that are not provided by the packaging cell line. Eukaryotic cell expression vectors are well known in the art and are available from a number of commercial sources.

In some embodiments, one or more multicistronic expression vectors are utilized that include two or more of the elements (e.g., the viral genes, at least one of: an m1-α sequence and an m1-β sequence, a suicide gene or genes) necessary for production of a desired recombinant virus in packaging cells. The use of multicistronic vectors reduces the total number of vectors required and thus avoids the possible difficulties associated with coordinating expression from multiple vectors. In a multicistronic vector the various elements to be expressed are operably linked to one or more promoters (and other expression control elements as necessary). In some embodiments a multicistronic vector comprising a suicide gene and/or a reporter gene, viral elements and nucleotide sequences encoding all or part of an α or β subunit of a MART-1 TCR, is used, wherein the nucleotide sequences are substantially as described herein.

Each component to be expressed in a multicistronic expression vector may be separated, for example, by an IRES element or a viral 2A element, to allow for separate expression of the various proteins from the same promoter. IRES elements and 2A elements are known in the art (U.S. Pat. No. 4,937,190; de Felipe et al. 2004. *Traffic* 5: 616-626, each of which is incorporated herein by reference in its entirety). In one embodiment, oligonucleotides encoding furin cleavage site sequences (RAKR) (Fang et al. 2005. *Nat. Biotech* 23: 584-590, which is incorporated herein by reference in its entirety) linked with 2A-like sequences from foot-and-mouth diseases virus (FMDV), equine rhinitis A virus (ERAV), and thosea asigna virus (TaV) (Szymczak et al. 2004. *Nat. Biotechnol.* 22: 589-594, which is incorporated herein by reference in its entirety) are used to separate genetic elements in a multicistronic vector. The efficacy of a particular multicistronic vector for use in synthesizing the desired recombinant virus can readily be tested by detecting expression of each of the genes using standard protocols. Exemplary protocols that are well known in the art include, but are not limited to, antibody-specific immunoassays such as Western blotting.

Vectors will usually contain a promoter that is recognized by the packaging cell and that is operably linked to the polynucleotide(s) encoding the targeting molecule, viral components, and the like. A promoter is an expression control element formed by a nucleic acid sequence that permits binding of RNA polymerase and transcription to occur. Promoters are untranslated sequences that are located upstream (5') to the start codon of a structural gene (generally within about 100 to 1000 bp) and control the transcription and translation of the antigen-specific polynucleotide sequence to which they are operably linked. Promoters may be inducible or constitutive. The activity of the inducible promoters is induced by the presence or absence of biotic or abiotic factors. Inducible promoters can be a useful tool in genetic engineering because the expression of genes to which they are operably linked can be turned on or off at certain stages of development of an organism or in a particular tissue. Inducible promoters can be grouped as chemically-regulated promoters, and physically-regulated promoters. Typical chemically-regulated promoters include, not are not limited to, alcohol-regulated promoters (e.g. alcohol dehydrogenase I (alcA) gene promoter), tetracycline-regulated promoters (e.g. tetracycline-responsive promoter), steroid-regulated promoter (e.g. rat glucocorticoid receptor (GR)-based promoter, human estrogen receptor (ER)-based promoter, moth ecdysone receptor-based promoter, and the promoters based on the steroid/retinoid/thyroid receptor superfamily), metal-regulated promoters (e.g. metallothionein gene-based promoters), and pathogenesis-related promoters (e.g. *Arabidopsis* and maize pathogen-related (PR) protein-based promoters). Typical physically-regulated promoters include, but are not limited to, temperature-regulated promoters (e.g. heat shock promoters), and light-regulated promoters (e.g. soybean SSU promoter). Other exemplary promoters are described elsewhere, for example, in hyper text transfer protocol://www.patentlens.net/daisy/promoters/768/271.html.

One of skill in the art will be able to select an appropriate promoter based on the specific circumstances. Many different promoters are well known in the art, as are methods for operably linking the promoter to the gene to be expressed. Both native promoter sequences and many heterologous promoters may be used to direct expression in the packaging cell and target cell. However, heterologous promoters are preferred, as they generally permit greater transcription and higher yields of the desired protein as compared to the native promoter.

The promoter may be obtained, for example, from the genomes of viruses such as polyoma virus, fowlpox virus, adenovirus, bovine papilloma virus, avian sarcoma virus, cytomegalovirus, a retrovirus, hepatitis-B virus and Simian Virus 40 (SV40). The promoter may also be, for example, a heterologous mammalian promoter, e.g. the actin promoter or an immunoglobulin promoter, a heat-shock promoter, or the promoter normally associated with the native sequence, provided such promoters are compatible with the target cell. In one embodiment, the promoter is the naturally occurring viral promoter in a viral expression system.

Transcription may be increased by inserting an enhancer sequence into the vector(s). Enhancers are typically cis-acting elements of DNA, usually about 10 to 300 bp in length, that act on a promoter to increase its transcription. Many enhancer sequences are now known from mammalian genes (globin, elastase, albumin, α-fetoprotein, and insulin). Preferably an enhancer from a eukaryotic cell virus will be used. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the antigen-specific polynucleotide sequence, but is preferably located at a site 5' from the promoter.

Other vectors and methods suitable for adaptation to the expression of viral polypeptides, are well known in the art and are readily adapted to the specific circumstances.

Using the teachings provided herein, one of skill in the art will recognize that the efficacy of a particular expression system can be tested by transforming packaging cells with a vector comprising a gene encoding a reporter protein and measuring the expression using a suitable technique, for example, measuring fluorescence from a green fluorescent protein conjugate. Suitable reporter genes are well known in the art.

A vector that encodes a core virus is also known as a "viral vector." There are a large number of available viral vectors that are suitable for use with the invention, including those identified for human gene therapy applications, such as those described by Pfeifer and Verma (Pfeifer, A. and I. M. Verma. 2001. *Ann. Rev. Genomics Hum. Genet.* 2:177-211, which is incorporated herein by reference in its entirety). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. Human Immunodeficiency virus (HIV-1)-derived vectors belong to this category. Other examples include lentivirus vectors derived from HIV-2, feline immunodeficiency virus (FIV), equine infectious anemia virus, simian immunodeficiency virus (SIV) and maedi/visna virus.

The viral vector preferably comprises one or more genes encoding components of the recombinant virus as well as nucleic acids encoding all or part of a functional MART-1 TCR. In some embodiments, the viral vector encodes components of the recombinant virus and at least one of: an M1-α variable region, an M1-β variable region and an M2-β variable region, and optionally, a suicide or reporter gene. In other embodiments, the viral vector encodes components of the recombinant virus and at least one of: an M1-α subunit, an M1-β subunit and an M2-β subunit, and optionally, a suicide or reporter gene. The viral vector may also comprise genetic elements that facilitate expression of the corresponding α and β polynucleotide sequences in a target cell, such as promoter and enhancer sequences. In order to prevent replication in the target cell, endogenous viral genes required for replication may be removed and provided separately in the packaging cell line.

In a preferred embodiment the viral vector comprises an intact retroviral 5' LTR and a self-inactivating 3' LTR.

Any method known in the art may be used to produce infectious retroviral particles whose genome comprises an RNA copy of the viral vector. To this end, the viral vector (along with other vectors encoding at least one of: an M1-α subunit and an M1-β subunit of a TCR that recognizes MART-1, and optionally, a suicide gene) is preferably introduced into a packaging cell line that packages viral genomic RNA based on the viral vector into viral particles.

The packaging cell line provides the viral proteins that are required in trans for the packaging of the viral genomic RNA into viral particles. The packaging cell line may be any cell line that is capable of expressing retroviral proteins. Preferred packaging cell lines include 293 (ATCC CCL X), HeLa (ATCC CCL 2), D17 (ATCC CCL 183), MDCK (ATCC CCL 34), BHK (ATCC CCL-10) and Cf2Th (ATCC CRL 1430). The packaging cell line may stably express the necessary viral proteins. Such a packaging cell line is described, for example, in U.S. Pat. No. 6,218,181, which is incorporated herein by reference in its entirety. Alternatively a packaging cell line may be transiently transfected with plasmids comprising nucleic acid that encodes one or more necessary viral proteins, including, but not limited to, gag, pol, rev, and any envelope protein that facilitates transduction of a target cell, along with the viral vectors encoding at least one of an M1-α subunit and an M1-β subunit of a TCR that recognizes MART-1.

Viral particles comprising a polynucleotide containing a gene of interest, which typically includes at least one of: an m1-α variable region nucleotide sequence, an m1-β variable region nucleotide sequence, an m2-β variable region nucleotide sequence, and optionally, a suicide or reporter gene, are collected and allowed to infect the target cell. In some embodiments, the gene of interest includes at least one of: an m1-α subunit nucleotide sequence, an m1-β subunit nucleotide sequence and an m2-β subunit nucleotide sequence. In some preferred embodiments, the virus is pseudotyped to achieve target cell specificity. Methods for pseudotyping are well known in the art and also described herein.

In one embodiment, the recombinant virus used to deliver the gene of interest is a modified lentivirus and the viral vector is based on a lentivirus. As lentiviruses are able to infect both dividing and non-dividing cells, in this embodiment it is not necessary for target cells to be dividing (or to stimulate the target cells to divide).

In another embodiment, the recombinant virus used to deliver the gene of interest is a modified gammaretrovirus and the viral vector is based on a gammaretrovirus.

In another embodiment the vector is based on the murine stem cell virus (MSCV; (Hawley, R. G., et al. (1996) Proc. Natl. Acad. Sci. USA 93:10297-10302; Keller, G., et al. (1998) Blood 92:877-887; Hawley, R. G., et al. (1994) Gene Ther. 1:136-138, each of the foregoing which is incorporated herein by reference in its entirety). The MSCV vector provides long-term stable expression in target cells, particularly hematopoietic precursor cells and their differentiated progeny.

In another embodiment, the vector is based on a modified Moloney virus, for example a Moloney Murine Leukemia Virus. The viral vector can also can be based on a hybrid virus such as that described in Choi, J. K., et al. (2001. *Stem Cells* 19, No. 3, 236-246, which is incorporated herein by reference in its entirety).

A DNA viral vector may be used, including, for example adenovirus-based vectors and adeno-associated virus (AAV)-based vectors. Likewise, retroviral-adenoviral vectors also can be used with the methods of the invention.

Other vectors also can be used for polynucleotide delivery including vectors derived from herpes simplex viruses (HSVs), including amplicon vectors, replication-defective HSV and attenuated HSV (Krisky D M, Marconi P C, Oligino T J, Rouse R J, Fink D J, et al. 1998. Development of herpes simplex virus replication-defective multigene vectors for combination gene therapy applications. *Gene Ther.* 5: 1517-30, which is incorporated herein by reference in its entirety).

Other vectors that have recently been developed for gene therapy uses can also be used with the methods of the invention. Such vectors include those derived from baculoviruses and alpha-viruses. (Jolly D J. 1999. Emerging viral vectors. pp 209-40 in Friedmann T. ed. 1999. The development of human gene therapy. New York: Cold Spring Harbor Lab, which is incorporated herein by reference in its entirety).

In some preferred embodiments, the viral construct comprises sequences from a lentivirus genome, such as the HIV genome or the SIV genome. The viral construct preferably comprises sequences from the 5' and 3' LTRs of a lentivirus. More preferably the viral construct comprises the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Preferably the LTR sequences are HIV LTR sequences.

The viral construct preferably comprises an inactivated or self-inactivating 3' LTR. The 3' LTR may be made self-inactivating by any method known in the art. In the preferred embodiment the U3 element of the 3' LTR contains a deletion of its enhancer sequence, preferably the TATA box, Spl and NF-kappa B sites. As a result of the self-inactivating 3' LTR, the provirus that is integrated into the host cell genome will comprise an inactivated 5' LTR.

Optionally, the U3 sequence from the lentiviral 5' LTR may be replaced with a promoter sequence in the viral construct. This may increase the titer of virus recovered from the packaging cell line. An enhancer sequence may also be included. Any enhancer/promoter combination that increases expression of the viral RNA genome in the packaging cell line may be used. In a preferred embodiment the CMV enhancer/promoter sequence is used.

In some embodiments, the viral construct preferably comprises an inactivated or self-inactivating 3' LTR. The 3' LTR may be made self-inactivating by any method known in the art. In the preferred embodiment the U3 element of the 3' LTR contains a deletion of its enhancer sequence, preferably the TATA box, Spl and NF-kappa B sites. As a result of the self-inactivating 3' LTR, the provirus that is integrated into the host cell genome will comprise an inactivated 5' LTR.

The viral construct generally comprises a gene of interest, which typically includes at least one of: an m1-α variable region nucleotide sequence, an m1-β variable region nucleotide sequence, an m2-β variable region nucleotide sequence, an m1-α subunit nucleotide sequence, an m1-β subunit nucleotide sequence and an m2-β subunit nucleotide sequence, and optionally, a suicide or reporter gene that is desirably expressed in one or more target cells. Preferably the gene of interest is located between the 5' LTR and 3' LTR sequences. Further, the gene of interest is preferably in a functional relationship with other genetic elements, for example transcription regulatory sequences such as promoters and/or enhancers, to regulate expression of the gene of interest in a particular manner once the gene is incorporated into the target cell. In certain embodiments, the useful transcriptional regulatory sequences are those that are highly regulated with respect to activity, both temporally and spatially.

In some embodiments, the gene of interest is in a functional relationship with internal promoter/enhancer regulatory sequences. An "internal" promoter/enhancer is one that is located between the 5' LTR and the 3' LTR sequences in the viral construct and is operably linked to the gene that is desirably expressed.

The internal promoter/enhancer may be any promoter, enhancer or promoter/enhancer combination known to increase expression of a gene with which it is in a functional relationship. A "functional relationship" and "operably linked" mean, without limitation, that the gene is in the correct location and orientation with respect to the promoter and/or enhancer that expression of the gene will be affected when the promoter and/or enhancer is contacted with the appropriate molecules.

The internal promoter/enhancer is preferably selected based on the desired expression pattern of the gene of interest and the specific properties of known promoters/enhancers. Thus, the internal promoter may be a constitutive promoter. Non-limiting examples of constitutive promoters that may be used include the promoter for ubiquitin, CMV (Karasuyama et al. 1989. *J. Exp. Med.* 169:13, which is incorporated herein by reference in its entirety), beta-actin (Gunning et al. 1989. *Proc. Natl. Acad. Sci. USA* 84:4831-4835, which is incorporated herein by reference in its entirety) and pgk (see, for example, Adra et al. 1987. *Gene* 60:65-74; Singer-Sam et al.

1984. *Gene* 32:409-417; and Dobson et al. 1982. *Nucleic Acids Res.* 10:2635-2637, each of the foregoing which is incorporated herein by reference in its entirety).

In addition, promoters may be selected to allow for inducible expression of the gene. A number of systems for inducible expression are known in the art, including the tetracycline responsive system and the lac operator-repressor system. It is also contemplated that a combination of promoters may be used to obtain the desired expression of the gene of interest. The skilled artisan will be able to select a promoter based on the desired expression pattern of the gene in the organism and/or the target cell of interest.

In some embodiments the viral construct preferably comprises at least one RNA Polymerase II or III promoter. The RNA Polymerase II or III promoter is operably linked to the gene of interest and can also be linked to a termination sequence. In addition, more than one RNA Polymerase II or III promoters may be incorporated.

RNA polymerase II and III promoters are well known to one of skill in the art. A suitable range of RNA polymerase III promoters can be found, for example, in Paule and White. *Nucleic Acids Research.*, Vol 28, pp 1283-1298 (2000), which is incorporated herein by reference in its entirety. The definition of RNA polymerase II or III promoters, respectively, also include any synthetic or engineered DNA fragment that can direct RNA polymerase II or III, respectively, to transcribe its downstream RNA coding sequences. Further, the RNA polymerase II or III (Pol II or III) promoter or promoters used as part of the viral vector can be inducible. Any suitable inducible Pol II or III promoter can be used with the methods of the invention. Particularly suited Pol II or III promoters include the tetracycline responsive promoters provided in Ohkawa and Taira *Human Gene Therapy*, Vol. 11, pp 577-585 (2000) and in Meissner et al. *Nucleic Acids Research*, Vol. 29, pp 1672-1682 (2001), each of which is incorporated herein by reference in its entirety.

An internal enhancer may also be present in the viral construct to increase expression of the gene of interest. For example, the CMV enhancer (Karasuyama et al. 1989. *J. Exp. Med.* 169:13, which is incorporated herein by reference in its entirety) may be used. In some embodiments, the CMV enhancer can be used in combination with the chicken β-actin promoter. One of skill in the art will be able to select the appropriate enhancer based on the desired expression pattern.

In addition to containing at least one of: an m1-α variable region nucleotide sequence, an m1-β variable region nucleotide sequence, an m2-β variable region nucleotide sequence, an m1-α subunit nucleotide sequence, an m1-β subunit nucleotide sequence and an m2-β subunit nucleotide sequence, in some embodiments, the polynucleotide can contain at least one additional gene of interest, which can be placed in functional relationship with the viral promoter. The additional gene of interest can encode a suicide gene which is designed for the elimination of transduced target cells or alternatively, used for imaging purposes. An exemplary suicide gene includes, but is not limited to, sr39tk, as described herein. Other exemplary suicide genes include, but are not limited to, HSVtk, *E. coli* cytosine deaminase (CD) genes, *E. coli* nitroreductase genes, carboxylesterase genes, cytochrome P450 genes and the like. In other embodiments, the additional gene of interest can be a gene encoding a marker protein to allow for identification of cells that are expressing the genes of interest. In one embodiment a fluorescent marker protein, preferably green fluorescent protein (GFP), is incorporated into the construct along with the gene of interest (typically encoding at least one of: an M1-α subunit and an M1-β subunit of a TCR that recognizes MART-1). If more than one gene of interest is included in the polynucleotide, internal ribosomal entry site (IRES) sequences, or 2A elements are also preferably included, separating the primary gene of interest from a reporter gene and/or any other gene of interest. The IRES or 2A sequences may facilitate the expression of the reporter gene, or other genes.

The viral construct may also contain additional genetic elements. The types of elements that may be included in the construct are not limited in any way and will be chosen by the skilled practitioner to achieve a particular result. For example, a signal that facilitates nuclear entry of the viral genome in the target cell may be included. An example of such a signal is the HIV-1 flap signal.

Further, elements may be included that facilitate the characterization of the provirus integration site in the target cell. For example, a tRNA amber suppressor sequence may be included in the construct.

In addition, the construct may contain one or more genetic elements designed to enhance expression of the gene of interest. For example, a woodchuck hepatitis virus responsive element (WRE) may be placed into the construct (Zufferey et al. 1999. *J. Virol.* 74:3668-3681; Deglon et al. 2000. *Hum. Gene Ther.* 11:179-190, each of which is incorporated herein by reference in its entirety).

A chicken β-globin insulator may also be included in the viral construct. This element has been shown to reduce the chance of silencing the integrated provirus in the target cell due to methylation and heterochromatinization effects. In addition, the insulator may shield the internal enhancer, promoter and exogenous gene from positive or negative positional effects from surrounding DNA at the integration site on the chromosome.

Any additional genetic elements are preferably inserted 3' of the gene of interest.

In a specific embodiment, the viral vector comprises: a cytomegalovirus (CMV) enhancer/promoter sequence; the R and U5 sequences from the HIV 5' LTR; the HIV-1 flap signal; an internal enhancer; an internal promoter; a gene of interest; the woodchuck hepatitis virus responsive element; a tRNA amber suppressor sequence; a U3 element with a deletion of its enhancer sequence; the chicken beta-globin insulator; and the R and U5 sequences of the 3' HIV LTR.

The viral construct is preferably cloned into a plasmid that may be transfected into a packaging cell line. The preferred plasmid preferably comprises sequences useful for replication of the plasmid in bacteria.

Delivery of the Virus

The virus may be delivered to a target cell in any way that allows the virus to contact the target cells in which delivery of a sequence containing a gene of interest is desired. Typically, the gene of interest contains at least one of: an m1-α variable region nucleotide sequence, an m1-β variable region nucleotide sequence, an m2-β variable region nucleotide sequence, an m1-α subunit nucleotide sequence, an m1-β subunit nucleotide sequence and an m2-β subunit nucleotide sequence.

In some embodiments, a suitable amount of virus is introduced into a subject directly (in vivo), for example though injection into the patient's body. In some preferred embodiments, the viral particles are injected into a subject's peripheral blood stream. In other preferred embodiments, the viral particles are injected into a subject through intra-dermal injection, subcutaneous injection, intra-peritoneal cavity injection, or intra-venal injection. The virus may be delivered using a subdermal injection device such the devices disclosed in U.S. Pat. Nos. 7,241,275, 7,115,108, 7,108,679, 7,083,599, 7,083,592, 7,047,070, 6,971,999, 6,808,506, 6,780,171, 6,776,776, 6,689,118, 6,670,349, 6,569,143, 6,494,865, 5,997,501, 5,848,991, 5,328,483, 5,279,552, 4,886,499, all of which are incorporated by reference in their entirety for all purposes. Other injection locations also are suitable, such as directly into organs comprising target cells. For example intra-lymph node injection, intra-spleen injection, or intra-bone marrow injection may be used to deliver virus to the lymph node, the spleen and the bone marrow, respectively.

In other embodiments of the invention, a suitable amount of virus is introduced into target cells obtained from a subject (ex vivo), for example through incubation of the virus with target cells in culture. The target cells are typically peripheral blood mononuclear cells (PBMCs) or hematopoetic stem cells (HSCs) obtained from a healthy subject or a subject in need of treatment. Preferably, the target cells are obtained from a subject in whom it is desired to treat melanoma and induce melanoma tumor regression. Methods to obtain cells from a subject are well known in the art and are described herein and elsewhere, for example in, U.S. patent application Ser. No. 11/071,785, filed Mar. 2, 2005 and entitled "ANTIGEN SPECIFIC T CELL THERAPY". The virus may be suspended in media and added to the wells of a culture plate, tube or other container. The media containing the virus may be added prior to the plating of the cells or after the cells have been plated. Preferably cells are incubated in an appropriate amount of media to provide viability and to allow for suitable concentrations of virus in the media such that infection of the host cell occurs.

In still other embodiments, target cells are provided and contacted with the virus in vitro, such as in culture plates.

The cells are preferably incubated with the virus for a sufficient amount of time to allow the virus to infect the cells. Preferably the cells are incubated with virus for at least 1 hour, more preferably at least 5 hours and even more preferably at least 10 hours.

In ex vivo, in vitro and in vivo delivery embodiments, any concentration of virus that is sufficient to infect the desired target cells may be used, as can be readily determined by the skilled artisan. When the target cell is to be cultured, the concentration of the viral particles is at least 1 PFU/μl, more preferably at least 10 PFU/μl, even more preferably at least 400 PFU/μl and even more preferably at least $1\times10^4$ PFU/μl.

In some embodiments, following infection with the virus in vitro or ex vivo, target cells can be introduced (or re-introduced) into an animal. In some embodiments, the cells can be introduced into the peripheral blood stream by, for example, intravenous infusion. The cells introduced into a subject are preferably cells derived from that subject, to avoid an adverse immune response. Cells also can be used that are derived from a donor subject having a similar immune background. Other cells also can be used, including those designed to avoid an adverse immunogenic response.

The target cells may be analyzed, for example for integration, transcription and/or expression of the polynucleotide (typically containing at least one of: an m1-α sequence and an m1-β sequence), the number of copies of the gene integrated, and the location of the integration. Such analysis may be carried out at any time and may be carried out by any methods known in the art.

Subjects in which a recombinant virus or virus-infected target cells are administered can be analyzed for location of infected cells, expression of the virus-delivered polynucleotide typically containing at least one of: an m1-α sequence and an m1-β sequence, stimulation of an immune response, and monitored for symptoms associated with a disease or disorder by any methods known in the art.

The methods of infecting cells disclosed above do not depend upon individual-specific characteristics of the cells. As a result, they are readily extended to all mammals. In some embodiments the recombinant virus is delivered to a human or to human PBMCs. In other embodiments, the recombinant virus is delivered to a mouse or to mouse cells. In still other embodiments, the recombinant virus is delivered to an animal other than a human or a mouse, or to cells from an animal other than a human or a mouse.

As discussed above, the recombinant virus can be pseudotyped to confer upon it a broad host range as well as target cell specificity. One of skill in the art would also be aware of appropriate internal promoters to achieve the desired expression of a polynucleotide or gene of interest in a particular animal species. Thus, one of skill in the art will be able to modify the method of infecting dendritic cells derived from any species.

T-cell Receptor (TCR) Gene Therapy

The transfer of T-cell receptor (TCR) genes endows recipient T cells with the specificity of donor cells (Dembic, Z., et al. 1987. *Nature* 326:510-511, which is incorporated herein by reference in its entirety). In embodiments of the invention, genetically modified T cells are engineered to carry MART-1 TCRs. The engineered T cells are able to respond to a MART-1 antigen recognition through the transgenic TCR expression both in vitro and in vivo leading to effective immune responses to melanoma. Typically, the T cell population is transduced with polynucleotide sequences that encode a MART-1 TCR comprising a TCR-α and TCR-β chain, wherein the α or β chain comprises an α variable region or a β variable region, respectively, resulting in stable MART-1 TCR surface expression. Suitable combinations of α and β chains or variable regions in a MART-1 TCR include the following: M1-α variable region and M1-β variable region, M2-α variable region and M2-β variable region, M1-α subunit and M1-β subunit, M2-α subunit and M2-β subunit. Any combination of α and β chains and/or variable regions in a MART-1 TCR are also contemplated, including, but not limited to: M1-α variable region and M2-β variable region, M2α variable region and M1-β variable region, M1-α subunit and M2-β subunit, M2α subunit and M2-β subunit.

In embodiments of the invention, the T cell population is transduced with one or more nucleotide sequences encoding at least one of: an M1-α variable region sequence, an M1-β variable region sequence and an M2-β variable region sequence. In other embodiments, the T cell population is transduced with one or more nucleotide sequences encoding at least one of: an M1-α subunit, an M1-β subunit and an M2-β subunit. The T cell population typically belongs to the T cell lineage and expresses CD3, a molecular complex required for both the assembly of the TCR and signaling upon antigen encounter (Rubinstein, M. P., et al. 2003. *J Immunol* 170:1209-1217; Roszkowski, J. J., et al. 2003. *J Immunol* 170:2582-2589, each of which is incorporated herein by reference in its entirety.)

The ability to generate large numbers of tumor antigen-specific T cells by a single ex vivo manipulation consisting of the transduction of melanoma-specific T-cell receptor (TCR) genes can result in a more broadly applicable approach for patients with melanoma. In a particular embodiment, methods are provided to engineer human CD8+ T lymphocytes to express a TCR specific for the human melanoma antigen MART-1 that is feasible and safe in human subjects and allows redirection of T cells to melanoma.

Typically, patients in need of treatment for melanoma are diagnosed clinically and identified by methods that are well known in the art.

In embodiments of the invention, a recombinant virus is used to deliver polynucleotides encoding at least one of: an M1-α variable region sequence, an M1-β variable region sequence and an M2-β variable region sequence, to immune cells. In other embodiments, a recombinant virus is used to deliver polynucleotides encoding at least one of: an M1-α subunit, an M1-β subunit and an M2-β subunit, to immune cells. The polynucleotides can comprise any of the nucleic acid molecules as described herein. In some embodiments, the delivery can be achieved by contacting immune cells with the recombinant virus in vitro, whereupon the transduced cells are provided to a patient. The transduced cells then stimulate MART-1-specific T cells in a patient to induce cellular and humoral immune responses against MART-1 antigen for treatment of melanoma and melanoma tumors.

In embodiments of the invention, the methods of the present invention can be used for adoptive immunotherapy in a patient in need of treatment for melanoma. As described herein, a polynucleotide encoding at least one of: an M1-α variable region, an M1-β variable region sequence and an M2-β variable region, or a polynucleotide encoding at least one of: an M1-α subunit, an M1-β subunit and an M2-β subunit, is obtained and packaged into a recombinant virus. Target cells, such as, for example, peripheral blood mononuclear cells (PBMCs) or hematopoetic stem cells (HSCs), are obtained from the patient and transduced ex vivo with a recombinant virus containing the polynucleotide. The transduced cells are then transferred back into the patient, where they express a TCR encoded by the polynucleotide that recognizes MART-1 antigen in melanoma tumors. The transduced cells accordingly target the MART-1 antigen in the melanoma tumors, thereby providing a therapeutic effect to facilitate the regression of the tumors.

In some embodiments of the invention, the methods of the present invention can be used for adoptive immunotherapy in a patient in need of treatment for melanoma, wherein the target cells are obtained from a healthy donor subject. As described herein, a polynucleotide encoding at least one of: an M1-α variable region, an M1-β variable region sequence and an M2-β variable region, or a polynucleotide encoding at least one of: an M1-α subunit, an M1-β variable subunit and an M2-β subunit, is obtained and packaged into a recombinant virus. Target cells are obtained from a healthy subject with immunogenic compatibility with the patient and transduced ex vivo with the recombinant virus containing the polynucleotide. The transduced cells are then transferred into the patient, where they express a TCR encoded by the polynucleotide that recognizes MART-1 antigen in melanoma tumors. The transduced cells accordingly target the MART-1 antigen in the melanoma tumors, thereby providing a therapeutic effect to facilitate the regression of the tumors.

In some embodiments of the invention, the methods of the present invention can be used for in vitro manipulation of target cells that are administered to a patient in need of treatment for melanoma. As described herein, a polynucleotide encoding at least one of: an M1-α variable region, an M1-β variable region sequence and an M2-β variable region, or a polynucleotide encoding at least one of: an M1-α subunit, an M1-β variable subunit and an M2-β subunit, is obtained and packaged into a recombinant virus. Target cells are provided and transduced in vitro with the recombinant virus containing the polynucleotide. The transduced cells are then transferred into the patient, where they express a TCR encoded by the polynucleotide that recognizes MART-1 antigen in melanoma tumors. The transduced cells accordingly target the MART-1 antigen in the melanoma tumors, thereby providing a therapeutic effect to facilitate the regression of the tumors.

In some embodiments of the invention, the transduced cells are combined with an equal number of unmanipulated cells prior to transfer into the patient.

In embodiments of the invention, the virus may be injected into a patient in need of treatment for melanoma, where it contacts target cells in vivo and delivers a polynucleotide, typically encoding at least one of: an M1-α variable region, an M1-β variable region sequence and an M2-β variable region, or typically encoding at least one of: an M1-α subunit, an M1-β variable subunit and an M2-β subunit. As described herein, the polynucleotide encoding at least one of: an M1-α variable region, an M1-β variable region sequence and an M2-β variable region, or a polynucleotide encoding at least one of: an M1-α subunit, an M1-β variable subunit and an M2-β subunit, is obtained and packaged into a recombinant virus. The virus is then injected into the patient, where it transduces target cells and induces expression of a TCR encoded by the polynucleotide that recognizes MART-1 antigen in melanoma tumors. The amount of viral particles is at least $50 \times 10^6$ TU, and can be at least $1 \times 10^7$ TU, at least $2 \times 10^7$ TU, at least $3 \times 10^7$, at least $4 \times 10^7$ TU, or at least $5 \times 10^7$ TU. The transduced cells accordingly target the MART-1 antigen in the melanoma tumors, thereby providing a therapeutic effect to facilitate the regression of the tumors.

In embodiments of the invention, the patient can further be provided with a dendritic cell (DC) vaccine, wherein the dendritic cells have been loaded with a MART-1 antigen. Compositions and methods of making and administering DC vaccines have been described elsewhere, for example, in U.S. patent application Ser. No. 11/517,814, filed Sep. 8, 2006 and entitled "METHOD FOR THE GENERATION OF ANTIGEN-SPECIFIC LYMPHOCYTES"; U.S. patent application Ser. No. 11/071,785, filed Mar. 2, 2005 and entitled "ANTIGEN SPECIFIC T CELL THERAPY"; U.S. patent application Ser. No. 11/446,353, filed Jun. 1, 2006 and entitled "METHOD OF TARGETED GENE DELIVERY USING VIRAL VECTORS"; and U.S. patent application Ser. No. 11/781,865, filed on Jul. 23, 2007 and entitled "TARGETED GENE DELIVERY FOR DENDRITIC CELL VACCINATION.".

In some embodiments of the invention, the patient can be provided with a MART-1 DC vaccine prior to administration of virus-transduced target cells, or alternatively, prior to administration of a recombinant virus, to the patient. In other embodiments, the patient can be provided with a MART-1 DC vaccine after administration of virus-transduced target cells or a recombinant virus to the patient. In still other embodiments, the patient can be provided with a MART-1 DC vaccine concurrent to administration of virus-transduced target cells or a recombinant virus to the patient. Any number of vaccination administrations is contemplated, including at least one, two, three, four, five and six doses.

In some embodiments of the invention, the DC vaccine contains dendritic cells that are loaded with a MART-1 antigen peptide. The MART-1 antigen peptide is at least 7, 8, 9, 10, 11, 12, 13, 14 or 15 amino acids in length. Any peptide corresponding to any number of residues included in a MART-1 sequence (SEQ ID NO: 19) is contemplated. Typical MART-1 antigen peptides include, but are not limited to, MART-$1_{26-35}$ (SEQ ID NO: 20), MART-$1_{27-35}$ and MART-$1_{51-73}$.

In embodiments of the invention, the patient can further be provided with a sufficient dose of interleukin. In some embodiments of the invention, the patient can be provided with a dose of interleukin prior to administration of virus-transduced target cells, or alternatively, prior to administration of a recombinant virus, to the patient. In other embodiments, the patient can be provided with a dose of interleukin after administration of virus-transduced target cells or a recombinant virus to the patient. In still other embodiments, the patient can be provided with a dose of interleukin concurrent to administration of virus-transduced target cells or a recombinant virus to the patient.

Any number of interleukin doses is contemplated, including at least one, two, three, four, five and six doses. A "sufficient" dose is one typically known to one of skill in the art, generally from about 600,000 to about 720,000 IU/kg delivered intravenously, though lower interleukin doses are also contemplated. In some embodiments, the interleukin dose can be administered as separate administrations. In other embodiments, the interleukin dose can be administered continuously over a number of days. Typically, the interleuking dose is administered by intravenous (i.v.) injection.

In some embodiments of the invention, the interleukin is at least one selected from the following: interleukin-2 (IL-2), interleukin-7 (IL-7), interleukin-15 (IL-15), interleukin-21 (IL-21) and interleukin-23 (IL-23).

In embodiments of the invention, the polynucleotide within the recombinant virus that encodes at least one of: an M1-α variable region, an M1-β variable region sequence and an M2-β variable region, or encodes at least one of an M1-α subunit, an M1-β variable subunit and an M2-β subunit, further comprises a suicide or reporter gene. In some embodiments, expression of a suicide gene in conjunction with administration of a substrate to the transduced cell results in cell death. In such embodiments, cell death is desirable where the transduced cells contribute to therapy-related side effects and/or toxicities in the patient. In other embodiments, expression of the suicide gene in conjunction with administration of a substrate to the transduced cell results in incorporation of a marker for visualization or imaging of the transduced cell.

Exemplary suicide genes include, but are not limited to, thymidine kinase genes, *E. coli* cytosine deaminase (CD) genes, *E. coli* nitroreductase genes, carboxylesterase genes and cytochrome P450 genes. For example, the suicide gene can be a thymidine kinase gene selected from sr39tk and HSVtk.

Exemplary substrates that can be administered to the transduced cell include, but are not limited to, ganciciclovir, acyclovir, CB1954, 5-fluorocytosine (5-FC), CPT-11 and cyclophosphamide. Additional exemplary substrates that can be administered include, but are not limited to, PET imaging substrate [18F]FHBG.

In particular embodiments of the invention, engineered CD8+ T-cells that express a high-affinity TCR that recognizes MART-1 antigen are provided to a patient in need of melanoma treatment. Peripheral blood mononuclear cells (PBMCs) are obtained from the patient and are activated with at least one of: CD2, CD3 and CD28. CD8+ cytotoxic T lymphocytes (CTLs) are isolated from the activated PBMC population and transduced with a prepared virus encoding at least one of: an M1-α variable region, an M1-β variable region sequence or encoding at least one of: an M1-α subunit, an M1-β variable subunit and an M2-β subunit. Preferably, the virus is a lentivirus. The virus-transduced CD8+ CTLs are typically transferred into a patient, where they efficiently produce T cells expressing the high-affinity TCR that specifically recognizes MART-1 antigen in vivo. The T-cells recognize the MART-1 antigen in melanoma tumors and accordingly target the melanoma tumors for destruction by the patient's immune system, thereby providing a therapeutic effect to for treatment of melanoma.

In some embodiments of the invention, the transduced cells are combined with an equal number of unmanipulated PBMCs prior to transfer into the patient.

Typical activating amounts of CD2, CD3 and CD28 are known to one of skill in the art. For example, activating amounts of CD2, CD3, and CD28 magnetic microbeads include, but are not limited to, at least about $2.5 \times 10^6$ nanoparticles per $5 \times 10^6$ peripheral blood mononuclear cells (PBMC), Kits The nucleic acids, polypeptides, vectors and recombinant virus provided herein can be packaged in kits. Kits can optionally include one or more components such as instructions for use, devices, and additional reagents, and components, such as tubes, containers and syringes for practice of the methods. Exemplary kits can include the viruses provided herein, and can optionally include instructions for use and at least one of the following: a device for detecting a virus in a target cell, a device for administering the transduced target cells to a subject, and a device for administering at least one additional compound or composition to a subject. Other exemplary kits can include the viruses provided herein, and can optionally include instructions for use and at least one of the following: a device for detecting a virus in a subject, a device for administering a virus to a subject, and a device for administering at least one additional compound or composition to a subject.

Kits comprising one or more recombinant viruses encoding a MART-1 TCR (typically comprising a nucleic acid encoding at least one of: an m1-α variable region nucleotide sequence, an m1-β variable region nucleotide sequence, an m2-β variable region nucleotide sequence, an m1-α subunit nucleotide sequence, an m1-β subunit nucleotide sequence and an m2-β subunit nucleotide sequence) and optionally, a suicide or reporter gene are contemplated herein. Also contemplated are kits comprising one or more viral vectors encoding a gene of interest (typically containing an m1-α variable region nucleotide sequence, an m1-β variable region nucleotide sequence, an m2-β variable region nucleotide sequence, an m1-α subunit nucleotide sequence, an m1-β subunit nucleotide sequence and an m2-β subunit nucleotide sequence) and optionally, a suicide or reporter gene. In some embodiments, the kit further includes at least one of the following: at least one plasmid encoding virus packaging components and at least one additional compound or composition to be delivered to a subject, such as an antigen for vaccination or an interleukin.

In some embodiments the at least one additional compound or composition can be any selected from: an interleukin, a drug substrate to facilitate cell death in transduced cells, a compound that can be visualized in transduced cells, an antigen loaded-dendritic cell composition, as herein described.

In one example, a kit can contain instructions. Instructions typically include a tangible expression describing the virus and, optionally, other components included in the kit, and methods for administration to a subject, including methods for determining the proper state of the subject, the proper dosage amount, and the proper administration method, for administering the virus. Instructions can also include guidance for monitoring the subject over the duration of the treatment time.

In another example, a kit comprising a viral vector can contain instructions describing the viral vector and, optionally, other components included in the kit, and methods for administration to a population of target cells, including methods for determining the proper target cell culture conditions, the proper administration amount, and the proper administration method, for administering the virus to the target cells. Instructions can also include guidance for monitoring the transduction protocol over the duration of the administration time.

Kits provided herein also can include a device for administering a virus, or alternatively, for administering a population of transduced cells, to a subject. Any of a variety of devices known in the art for administering medications or vaccines can be included in the kits provided herein. Exemplary devices include, but are not limited to, a hypodermic needle, an intravenous needle, a catheter, a needle-less injection device, an inhaler, and a liquid dispenser, such as an eyedropper.

Kits provided herein also can include a device for administering at least one additional compound to a subject. The at least one additional compound can be any chosen from the following: an interleukin, a drug substrate to facilitate cell death in transduced cells, a compound that can be visualized in transduced cells, or an antigen loaded-dendritic cell composition, as described herein. Any of a variety of devices known in the art for administering medications to a subject can be included in the kits provided herein. Exemplary devices include a hypodermic needle, an intravenous needle, a catheter, a needle-less injection, but are not limited to, a hypodermic needle, an intravenous needle, a catheter, a needle-less injection device, an inhaler, and a liquid dispenser such as an eyedropper. Typically the device for administering the compound of the kit will be compatible with the desired method of administration of the compound.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

All patent and literature references cited in the present specification are hereby incorporated by reference in their entirety.

EXAMPLE 1

Cloning of the MART-1 T-Cell Receptor (TCR)

Figure 2:
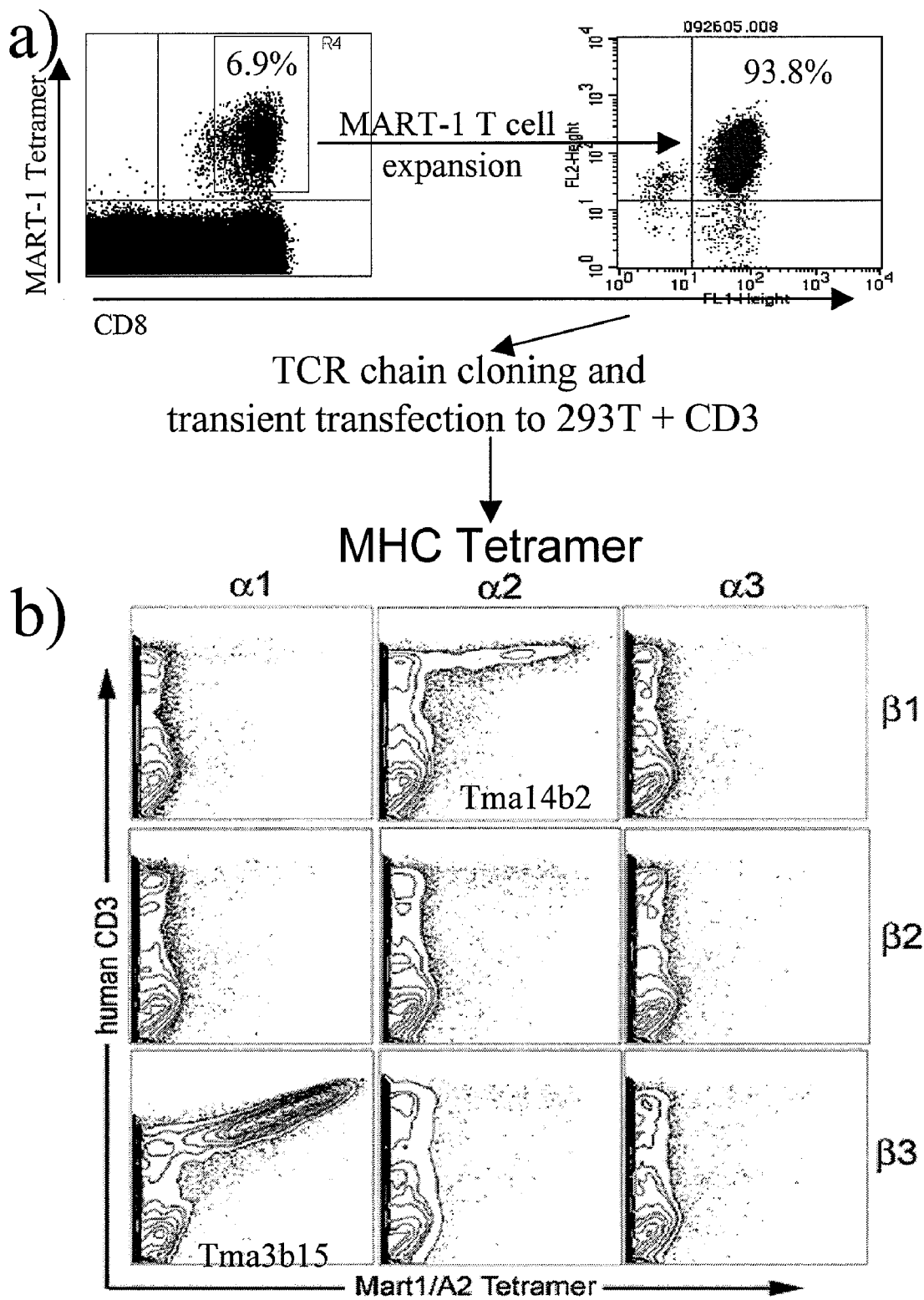
FIG. 2 illustrates the results of the cloning and functionality testing for several cloned MART-1 TCRs.

The MART-1 TCR gene was cloned from a patient with an unusual population of high affinity MART-1-specific T cells representing 5-7% of the patient's total CD8+ cells (FIG. 2). The particular patient is a 7-year survivor of widely metastatic melanoma to lung, nodes and brain who was treated with MART-1 antigen-transduced dendritic cells (DCs) and CTLA-4-blocking monoclonal antibody (CP-675,206). The patient had an unusually favorable clinical course, presenting with no evidence of disease (NED) 7 years after lung, brain and nodal metastases from melanoma.

Purified CD8+ T cells from the patient were stimulated by DCs pulsed with the MART-$1_{26-35}$ peptide (SEQ ID NO: 20) and expanded in IL-15. The cells were tetramer-sorted, and total RNA was isolated. 5-prime Race RT-PCR was employed to amplify the variable region of the TCR. Several TCR alpha chains and beta chains were identified. Genes encoding these chains were then cloned into mammalian expression vector pcDNA3 (Invitrogen). In a pairing experiment, 293T cells were co-transfected with one of the alpha chains, one of the beta chains and plasmids encoding the cDNAs of the four CD3 chains. Tetramer staining (specific for TCRs) and TCR functional assays confirmed that one pair, Tma14b2 (designated M1 pair, with M1-α subunit and M1-β subunit) was functionally superior (based on the amount of IFN-γ released by the transfected cells when stimulated by MART-1). TCR functional assays were conducted as described elsewhere (Holmberg, K., et al. 2003. *J Immunol* 171:2427-2434, which is incorporated herein by reference in its entirety).

The M1 pair comprising the very high affinity receptor for the MART-$1_{26-35}$ peptide, exhibited an affinity for solubilized MUC/MART-$1_{26-35}$ tetramers with a $K_D$ of 4 to 6 nM, which is one half to one log order of magnitude higher than other similarly tested TCRs (Holmberg, K., et al. 2003. supra). This MART-1 TCR is independent of CD8 co-receptor binding (FIG. 2b), and is able to bind to tetramers and specifically produce IFN-γ after transduction of the CD8 negative Jurkat T cell line (which is a model for CD4 cells) as described in Example 3 below.

EXAMPLE 2

Construction of a MART-1 TCR Lentiviral Vector

Figure 3:
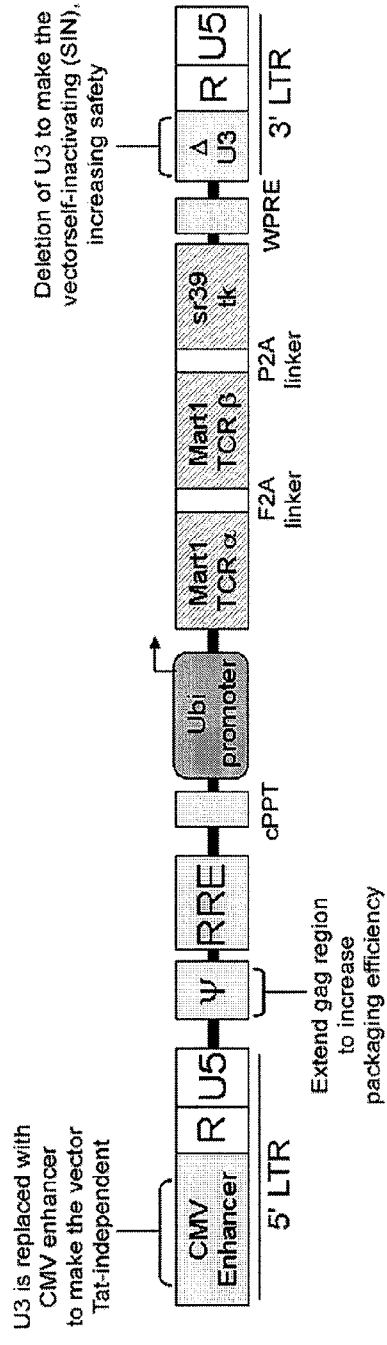
FIG. 3 shows a schematic representation of a lentiviral vector hereinafter referred to as "FUW-M1-TCR/sr39tk" (A) and packaging constructs (B) used for producing a recombinant lentivirus carrying an M1 TCR sequence. The recombinant virus obtained from the lentiviral vector in FIG. 3A is also referred to as the FUW-M1-TCR/sr39tk lentivirus or M1 lentivirus.
Figure 3:
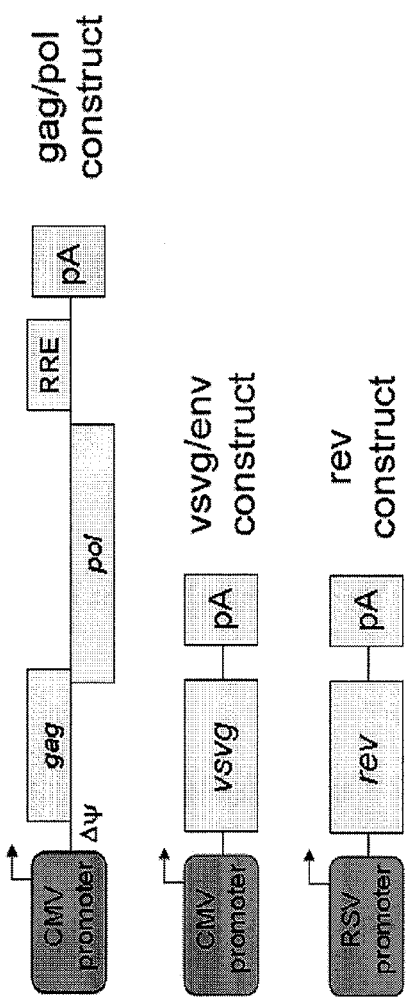

The gene transfer vector used in this study is a third generation HIV-based lentiviral vector (FIG. 3). FIG. 3 illustrates the MART-1 lentiviral vector used in experimental studies, known henceforth as "FFUW-M1-TCR/sr39tk." (SEQ ID NO: 17).

Extensive modifications were introduced into the vector to improve its safety for use. For example, most of the U3 region of the 3' LTR has been deleted to ensure that transcription from the 5' LTR is efficiently suppressed after reverse transcription and integration into cellular genome. As a result, the integrated vector cannot generate full-length vector RNA (called self-inactivating or SIN). In addition, an enhancer region derived from cytomegalovirus (CMV) immediate early promoter was used to replace the U3 region of 5' LTR. This modification eliminates the requirement for the presence of Tat protein for vector production without compromising viral titer. Furthermore, a human ubiquitin-C promoter was inserted into the vector to drive the expression of three transgenes inserted into the vector: MART-1 TCR alpha, MART-1 TCR beta, and suicide/imaging gene sr39tk.

Figure 4:
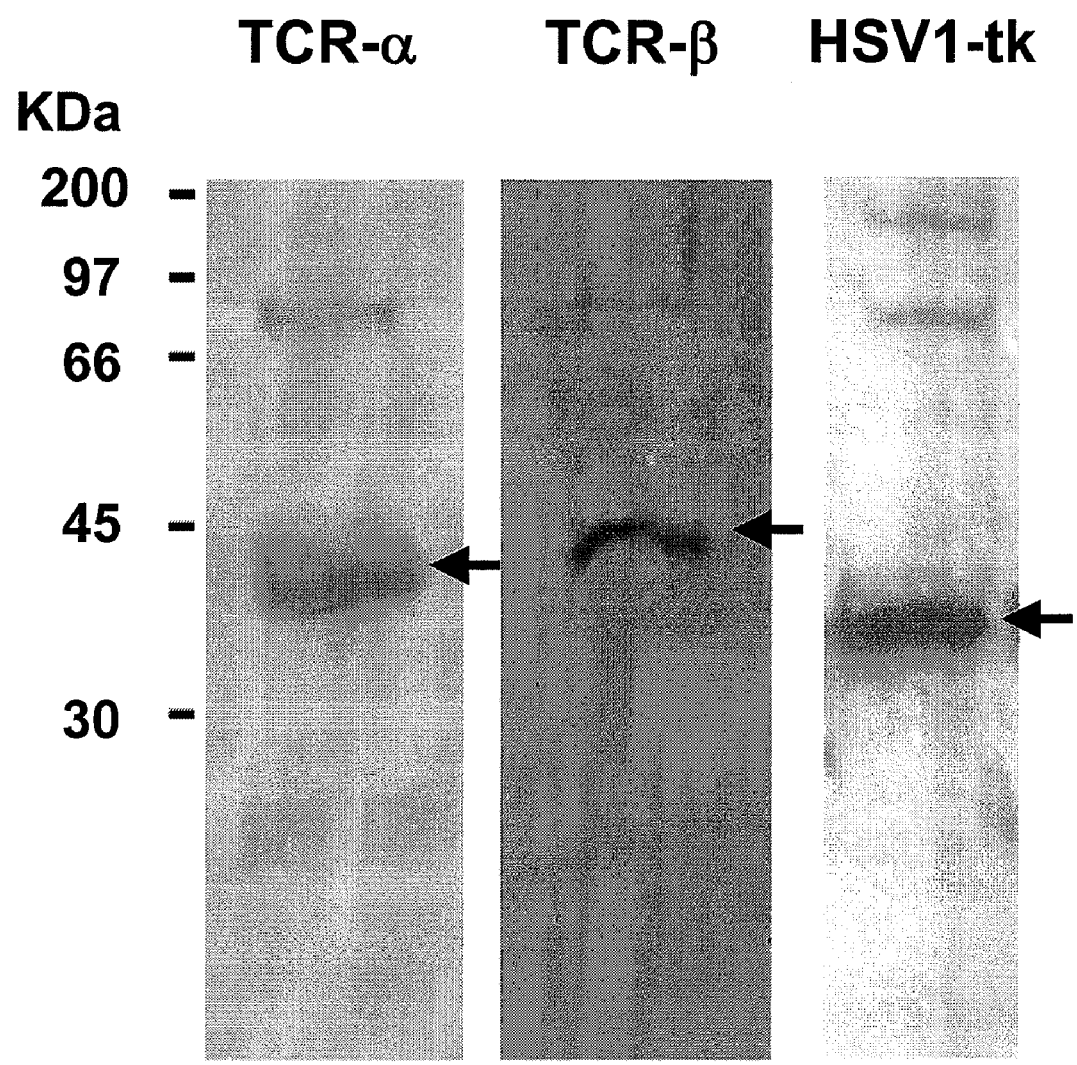
FIG. 4 illustrates expression of M1-α, M1-β and an sr39TK gene product in 293T cells. The 293T cells were transduced with M1 lentivirus. Arrows point to expected size bands for each protein.

Two "self-cleavage" 2A-like liners (F2A, derived from food-and-mouth disease virus; and P2A, derived from Porcine teschovirus) were used to link the three transgenes to achieve the optimal stoichiometric expression of these three proteins. Various designs for tri-cistronic configuration in lentiviral vector were evaluated, and the results indicated that the 2A-linkers offer the most efficient and reliable coexpression. (FIG. 4). The woodchuck post-transcriptional regulatory element (WPRE) was introduced downstream of transgenes to enhance expression of transfer genes.

To evaluate expression of the various tri-cistronic configurations in the lentiviral vectors, 293T cells (which do not express TCR nor HSV1-tk) were transduced with the lentiviral vector FUW-M1-TCR/sr39tk, lysed, subjected to SDS-PAGE and immunoblotted. Specific antibodies were used to detect the constant region of the α and β chains of the TCRs and HSV1-tk. In FIG. 4, the arrows point to the expected size bands for each protein. Weaker high molecular weigh bands correspond to uncleaved products. The cleavage efficiency of the linkers was estimated to be >90%.

EXAMPLE 3

Functional Activity of TCR-Engineered Cells

Figure 5:
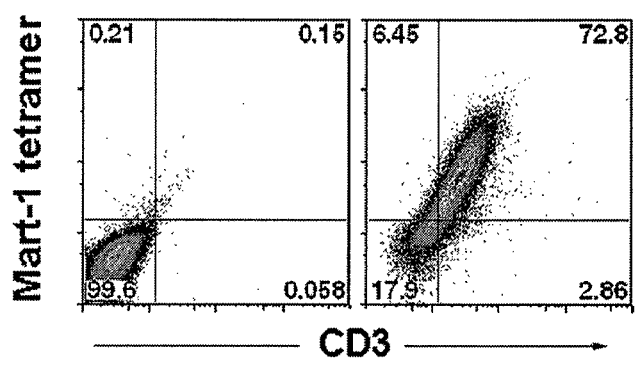
FIG. 5 shows analysis of different cells transduced with M1 lentivirus.
Figure 5:
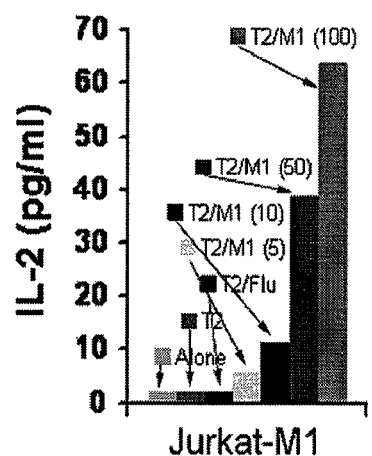
Figure 5:
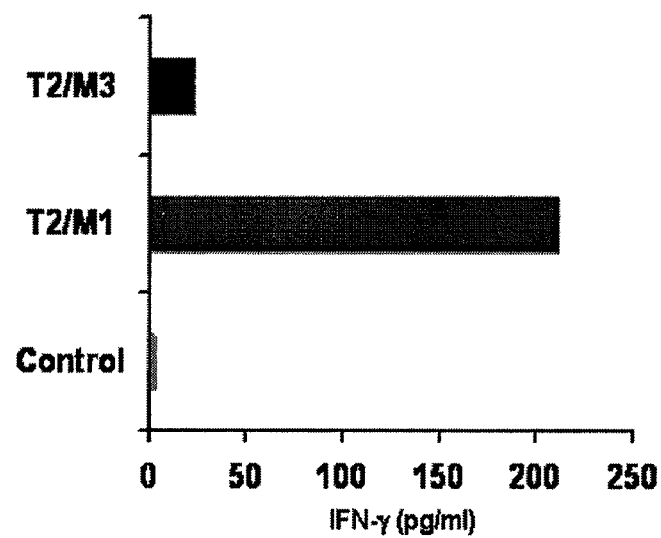

FUW-M1-TCR/sr39tk lentivirus vector transduction results in the surface expression of a MART-1-specific TCR in modified Jurkat cells and PBMC. In this experiment, Jurkat cells were transduced with the lentiviral vector encoding MART-1 TCR with a F2A linker (vector FUW-M1-TCR/sr39tk); resulting cells were designated as Jurkat-M1. Tetramer staining confirmed that over 70% cells are MART-1 positive (FIG. 5a). The assay for measuring interleukin-2 (IL-2) release was performed by co-incubation of Jurkat-M1 with T2 cells pulsed with various concentration of MART-$1_{26-35}$ peptide (designated as T2/M1) for three days. Supernatants were then collected for IL-2 ELISA analysis. Upon stimulation with MART-$1_{26-35}$ peptide, the Jurkat-M1 cells responded efficiently as manifested by healthy IL-2 production; the IL-2 response was correlated with the dosage of peptide supplied to the cells. Lack of IL-2 production from various controls demonstrated the specificity of the M1 TCR to recognize cognate antigen (FIG. 5b). In FIG. 5b, the various Jurkat-M1 populations were either not stimulated (control) or stimulated with T2 cells without peptide (T2), T2 cells loaded with an unrelated peptide (T2/Flu), or T2 cells loaded with x μg/nL of MART-$1_{26-35}$ peptide (T2/M1(x)).

Similarly, the functional response of MART-1 TCR in human primary peripheral blood mononuclear cells (PBMCs) was tested. PBMCs were stimulated with anti-CD3 and anti-CD28 antibodies for two days and then transduced with the lentiviral vector FUW-M1-TCR/sr39tk. Three days post-transduction, the cells were stimulated overnight by MART-$1_{26-35}$ peptide-loaded T2 cells (T2/M1); an unrelated MAGE-3 loaded T2 cell population (T2/M3) was used as specificity control. The supernatants were harvested and tested for IFN-γ by ELISA. MART-1-transduced PBMC responded vigorously to cognate MART-$1_{26-35}$ peptide, as indicated by production of effector cytokine IFN-γ. Control stimulation with an unrelated peptide resulted background level of IFN-γ, indicating that the cloned MART-1 TCR is specific to cognate antigen (FIG. 5c). In FIG. 5c, T2/M1 represents the lentivirus-transduced PBMCs stimulated by MART-$1_{26-35}$ peptide-loaded T2 cells, and T2/M3 represents the lentivirus-transduced PBMCs stimulated by T2 cells loaded with an unrelated MAGE-3 peptide as a specificity control.

Figure 11:
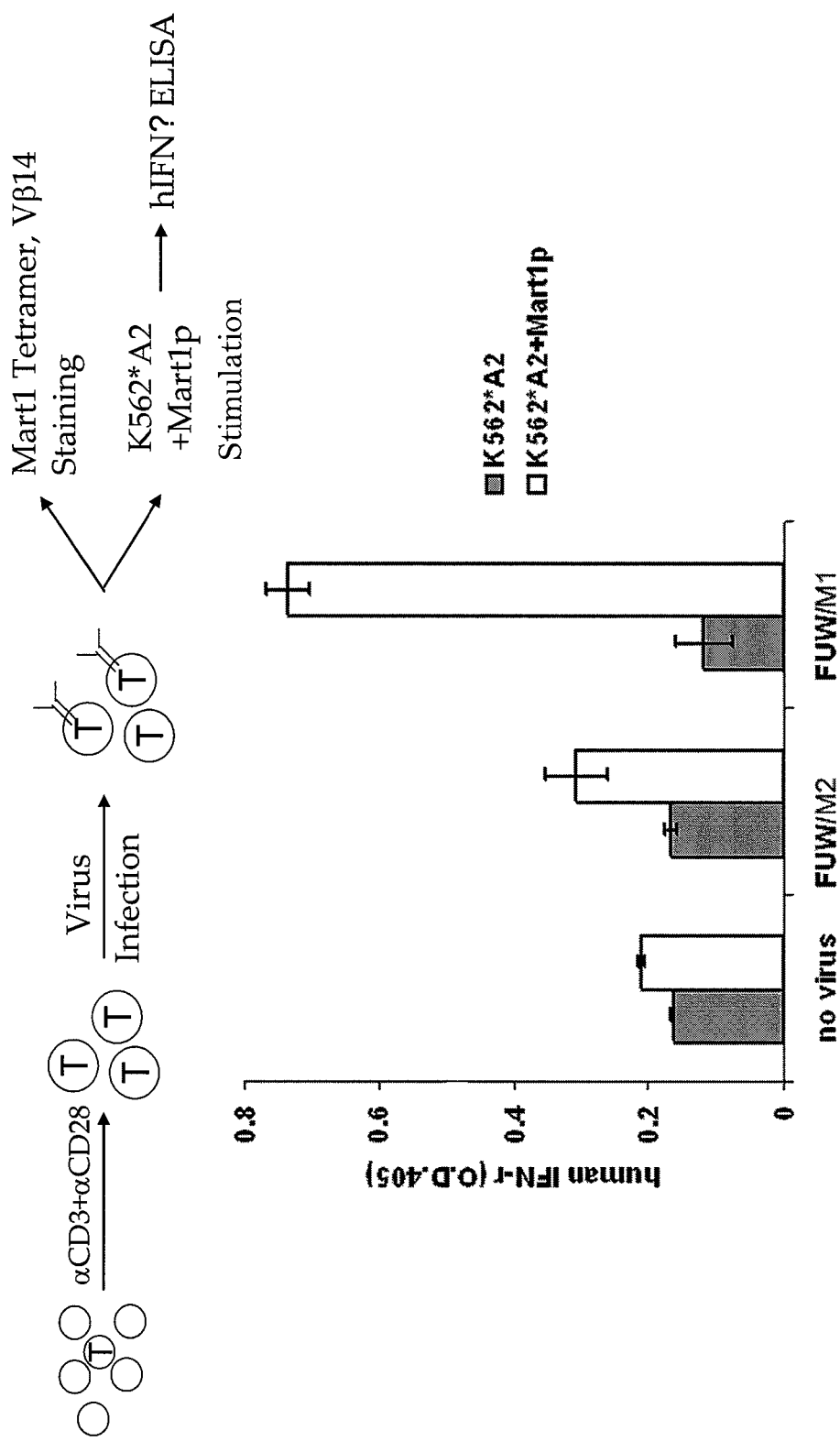
FIG. 11 shows the results from a functional response assay of two different MART-1 TCRs that were cloned. The M1 and M2 TCRs that were cloned were stimulated with MART-1 peptide loaded A2 cells and assayed for production of IFN-γ.

In a separate study, the functional response of the MART-1 TCR in human primary peripheral blood mononuclear cells (PBMCs) was tested and compared against another clone of MART-1 TCR that was isolated (Tma3b15, or "M2" clone). PBMCs were stimulated with anti-CD3 and anti-CD28 antibodies for two days and then transduced with the lentiviral vector FUW-M1-TCR/sr39tk (encoding "M1" TCR) or a similar vector carrying the sequences encoding M2 TCR α and β subunits (SEQ ID NO: 9, SEQ ID NO: 13). Three days post-transduction, the cells were analyzed for M1 or M2 TCR expression using flow cytometry. The cells were subsequently stimulated by co-culturing with K562*A2 cells pulsed with MART-$1_{26-35}$. The supernatants were harvested and tested for IFN-γ by ELISA. The M1-transduced PBMC exhibited a potent response to cognate MART-$1_{26-35}$ peptide, as indicated by production of effector cytokine IFN-γ (FIG. 13). However, the M2-transduced PBMC responded less effectively, though the increased response was statistically significant. In FIG. 11, FUW/M2 represents M2 lentivirus-transduced PBMCs and FUW/M1 represents M1 lentivirus-transduced PBMCs.

EXAMPLE 4

Optimization of Transduction Efficiency

Key variables in transduction efficiency of primary peripheral blood mononuclear cells (PMBCs) are T cell activation and vector titer. The protocol for CD8+ T cell activation was optimized by testing several conditions.

The results indicated that activation of whole PBMCs is superior to activation of purified CD8+ T cells. Whole PBMCs were activated with OKT3 and interleukin-2 (IL-2) for 2 days. CD8+ T cells were column-selected (CliniMACS system, Miltenyi Biotech) and transduced with a lentiviral vector expressing GFP (SEQ ID NO: 21). The transduction efficiency was compared to CD8+ T cells purified by magnetic column selection before OKT3/IL-2 activation. In replicate studies, activation of whole PBMC followed by CD8+ selection resulted in higher transduction efficiency.

The results also indicated that superior activation of T cells occurred with CD2/CD3/CD28 beads. Two T cell activation protocols using reagents compatible with clinical use were evaluated; one approach utilized the standard NCI approach using OKT3 and IL-2 as described above, and the second approach included the use of CD2/CD3/CD28 beads from Miltenyi. In Protocol 1, PBMCs were stimulated with human interleukin-2 (hIL2) at 300 U/ml and anti-CD3 (OKT3) at 50 ng/ml. In Protocol 2, PBMCs were treated with anti-CD2, CD3, CD28 conjugated beads (Miltenyi Biotec) at a ratio of 1 bead for every 2 cells. After 48 hours and 36 hours respectively, $1 \times 10^6$ non-adherent PBMCs were transduced with the lentivirus FUW-M1-TCR/sr39tk at a multiplicity of infection (M.O.I.) of 20. Four days after transduction, flow cytometry was conducted to analyze cell surface expression of Vβ14, and MART-$1_{26-35}$/HLA-A2.1 tetramer assays were performed to access transduction efficiency.

Table 1 provides details of the second experiment and illustrates that the transduction efficiency and surface MART-1 TCR expression in both CD8 and CD4 T cells is higher using the Miltenyi bead activation approach.

TABLE 1

| Comparison of lentiviral transduction efficiencies | | |
|---|---|---|
| | Protocol 1: IL-2 + OKT3 | Protocol 2: CD2, CD3, CD28 Beads |
| Vβ14 expression | 2.3-4.8% | 31.8-45.1% |
| MART-1 tetramer (transduction efficiency) | 1.5-1.8% | 11.3-12.5% |

EXAMPLE 5

Affinity of Cloned MART-1 T-Cell Receptor (TCR) for Mart-1 Antigen

The affinity for MART-$1_{26-35}$ MTC tetramers between cells obtained from leukapheresis from the MART-1 TCR donor patient and Jurkat cells that had been stably transfected with the alpha and beta genes of the cloned MART-1 TCR was compared using a formal equilibrium binding study (Holmberg, K., et al. 2003. supra; Savage, P. A., et al. 1999. *Immunity* 10:485-492, which is incorporated by reference in its entirety).

Figure 6:
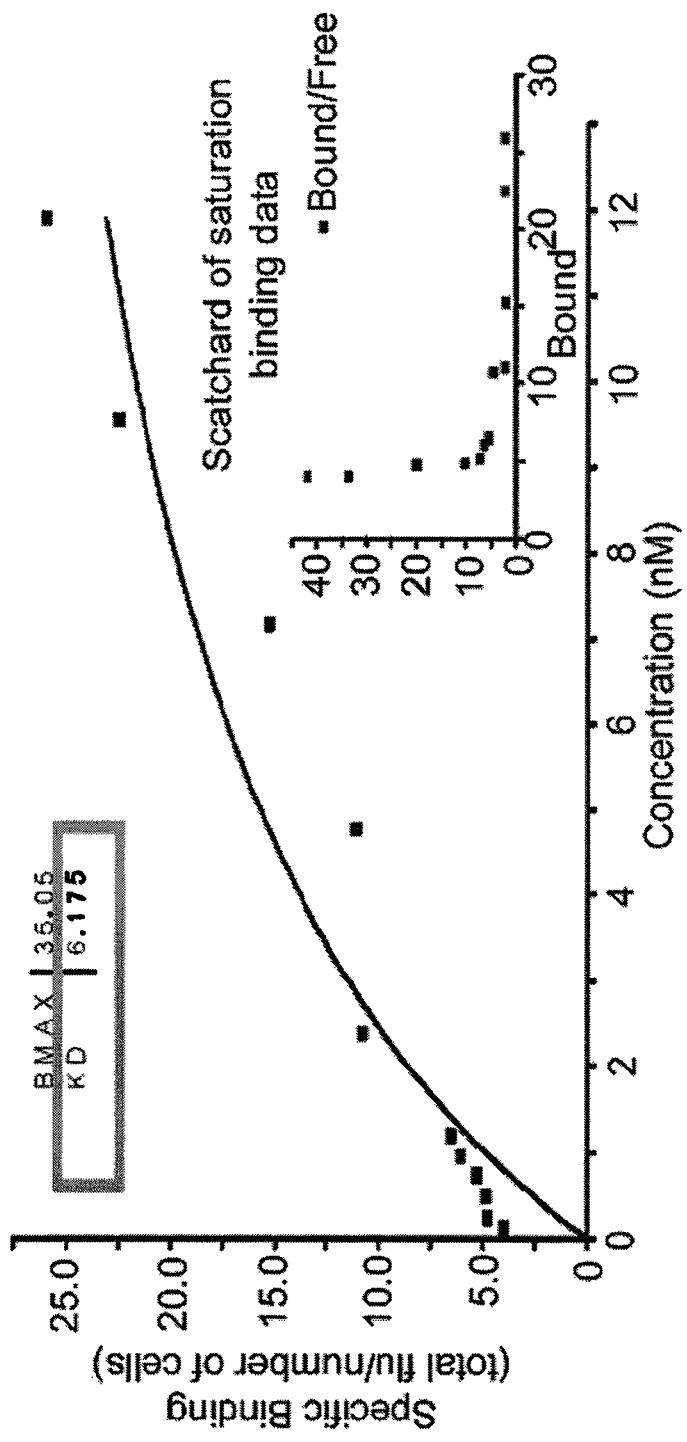
FIG. 6 shows the affinity of TCR in cells obtained from a patient for MART-1 MHC tetramers. The patient was the source of an M1 TCR pair.
Figure 7:
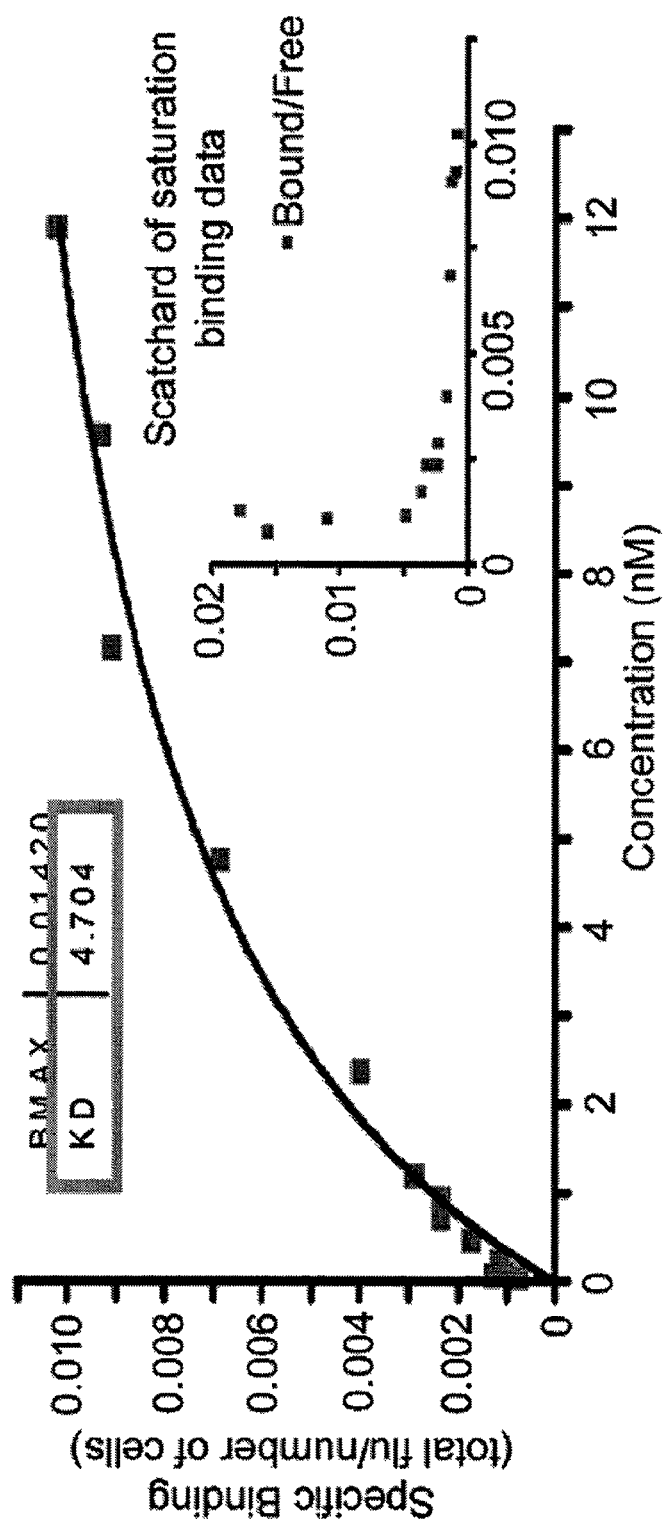
FIG. 7 shows the affinity of TCRs in Jurkat cells transfected with alpha and beta gene sequences of M1 TCR for MART-1 MHC tetramers.

In brief, MART-1 tetramers were used to stain the target cells at a range of tetramer concentrations between 0.1-25 nM. Scatchard plots were generated by plotting the Geometric Mean Fluorescence (GMF) divided by the concentration of tetramer versus the GMF. From those plots, the TCR avidity was calculated as $K_D = 1/\text{slope}$. In the experiments, the $K_D$ for both the MART-1 TCR native PBMC (FIG. 6) and the MART-1 TCR genetically engineered Jurkat cells were approximately the same, ranging from between 4 and 6 nM concentration of MART-1$_{26-35}$ tetramer (FIG. 7). The results indicated that the transgenic MART-1 TCR alpha and beta gene pair has the same affinity for the MART-1$_{26-35}$/HLA-A2.1 complexes as the cells extracted directly from the patient.

EXAMPLE 6

Functionality of HSV1-sr39tk as a Suicide Gene

Figure 8:
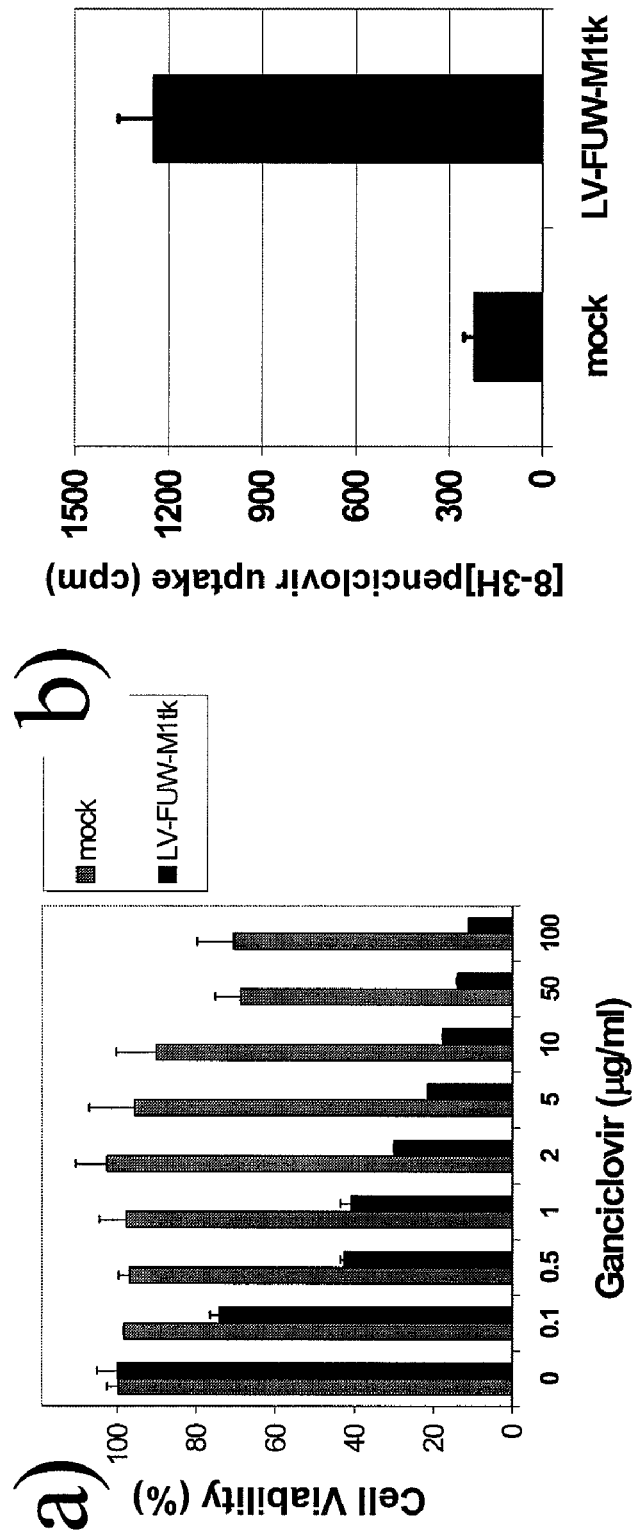
FIG. 8 illustrates the results of functionality testing for the sr39tk gene product in 293T cells transduced with M1 lentivirus.

The in vitro ganciclovir (GCV) lysis assay (Robe, P. A., et al. 2005. *BMC Cancer* 5:32, which is incorporated herein by reference in its entirety) was conducted to assess the function of sr39tk as a suicide gene (Dubey, P., et al. 2003. *Proc Natl Acad Sci USA* 100: 1232-1237, which is incorporated herein by reference in its entirety). Jurkat cells and primary human PBMC were transduced with the lentiviral vector FUW-M1-TCR/sr39tk to acquire sensitivity to ganciclovir (FIG. 8).

In the ganciclovir lysis assay (FIG. 8*a*), transduced 293T cells were transferred to a 96-well plate and treated with various concentrations of ganciclovir. Cell viability was assessed by the MTS in vitro cytotoxicity assay according to the manufacturer's protocol. The results indicate that the transduced 293T cells exhibited a higher sensitivity to ganciclovir than control, non-transduced 293T cells.

EXAMPLE 7

Functionality of HSV1-sr39tk as a Pet Reporter Gene

An 8-[$^3$H]Penciclovir incorporation assay was conducted to assess the function of sr39tk as a PET imaging gene (Dubey, P., et al. 2003. *Proc Natl Acad Sci USA* 100:1232-1237, which is incorporated herein by reference in its entirety). Jurkat cells and primary human PBMC were transduced with the lentiviral vector FUW-M1-TCR/sr39tk to acquire the ability to accumulate intracellular 8-[$^3$H]Penciclovir (FIG. 8).

In the penciclovir uptake assay (FIG. 8*b*), transduced 293T cells were incubated with 8-[$^3$H]Penciclovir, washed and measured for penciclovir uptake by a Gamma-counter. The results indicate that the transduced 293T cells exhibit a greater measure of 8-[$^3$H]Penciclovir uptake than control, non-transduced 293T cells. The transduced 293T cells thus demonstrate that transduction of the sr39tk gene-containing lentivector confers the ability to image transduced cells by PET imaging.

EXAMPLE 8

CD4 Treg Cells do not Interfere with the Antitumor Activity of T Cell Adoptive Transfer One embodiment of adoptive therapy that is contemplated is the combination of MART-1 TCR/sr39tk-transduced CD8+ T cells with an equal number of whole, unmanipulated PBMC to patients. Preclinical and clinical data indicates that CD4 T helper cells improve the antitumor activity of adoptively transferred CD8+ T cells (Dudley, M. E., et al. 2002. *Science* 298:850-854; Gattinoni, L., et al. 2006. *Nat Rev Immunol* 6:383-393; Dudley, M. E., et al. 2002. *J Immunother* 25:243-251, each of which incorporated herein by reference in its entirety). A pmel-1 model was used to evaluate this approach (Overwijk, W. W., et al. 2003. *J Exp Med* 198:569-580, which is incorporated herein by reference in its entirety).

Pmel-1 mice contain a transgenic Vα1Vβ13 T-cell receptor (TCR) that specifically recognizes the murine melanoma tumor antigen gp100$_{25-33}$ peptide presented by H2 D$^b$ (Overwijk, W. W., et al. 2003. supra). It has been demonstrated that adoptive transfer of pmel-1 splenocytes to mice having established B16 tumors induces tumor regression only when the recipient mice have undergone lymphodepleting chemotherapy or radiotherapy, and the adoptive transfer is followed by administered of gp100 vaccines and high doses of human recombinant IL-2 (Gattinoni, L., et al. 2006. supra; Lou, Y., et al. 2004. *Cancer Res* 64:6783-6790; Antony, P. A., et al. 2005. *J Immunol* 174:2591-2601; Klebanoff, C. A., et al. 2005. *Proc Natl Acad Sci USA* 102:9571-9576, each of which is incorporated herein by reference in its entirety). After adoptive transfer, peripheral pmel-1 T cells expanded in the lymphopenic environment, as measured by H-2 D$^b$/gp 100$_{25-33}$ tetramer staining. This expansion was enhanced by vaccination with gp100$_{25-33}$ pulsed DC plus IL-2; after vaccination was complete, the number of pmel-1 T cells regressed (data not shown).

Figure 9:
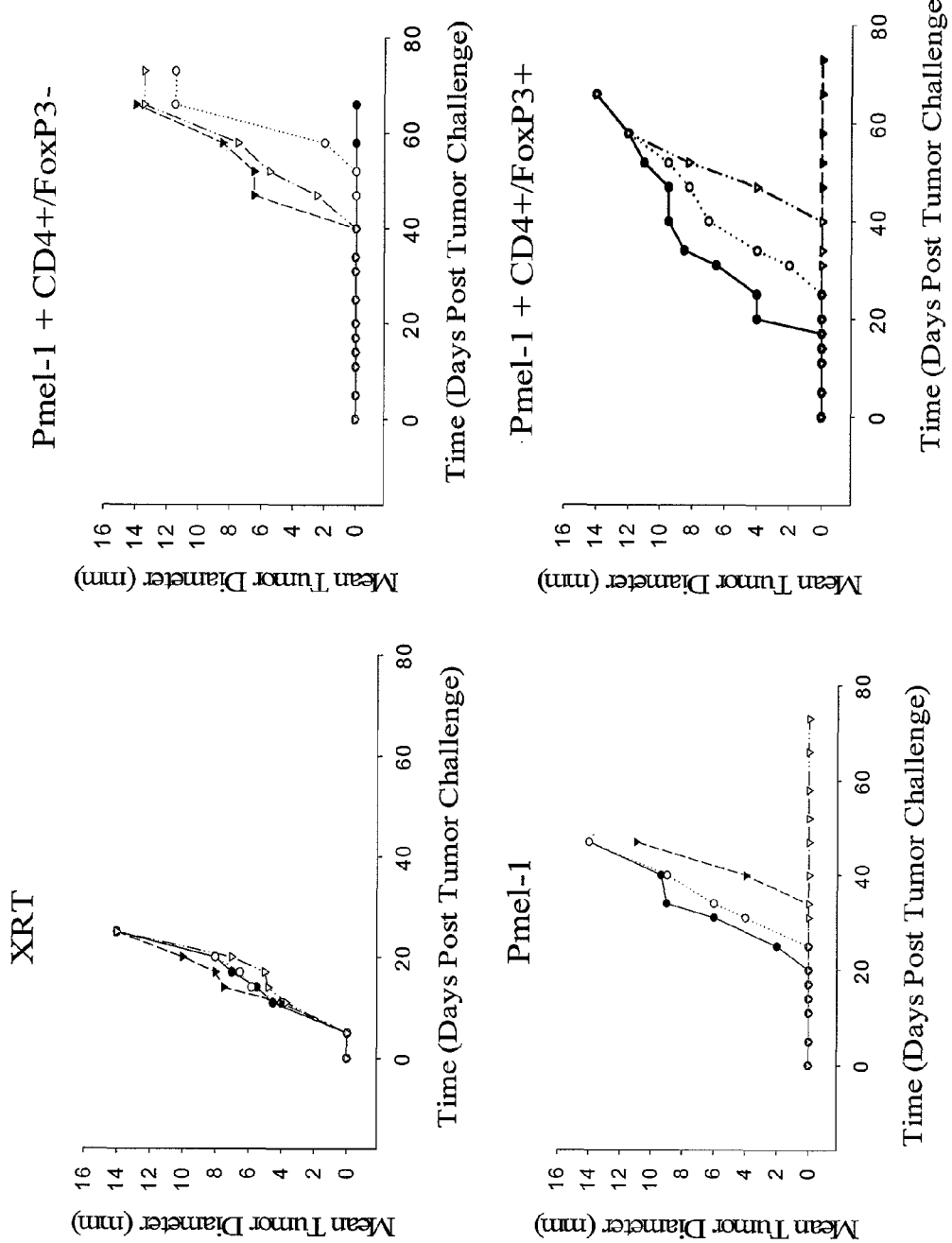
FIG. 9 illustrates that the anti-tumor activity of adoptively-transferred pmel-1/CD8 cells is not affected by FoxP3(+) or FoxP3(−) CD4 cells in mice with established tumors.

As shown in FIG. 9, $10^6$ pmel-1 (CD8) splenocytes adoptively transferred to conditioned mice mediate partial and complete regression of established B16 tumors. Briefly, Foxp3(+) CD4 spleen cells were purified by flow cytometry from Foxp3/GFP transgenic mice and shown to be bona fide T regulatory (Treg) cells (Fontenot, J. D., et al. 2005. *Immunity* 22:329-341, which is incorporated herein by reference in its entirety). C57BL/6 mice with day +6 established subcutaneous flank B16-F10 tumors were lymphodepleted with 500 cGy whole body irradiation. The next day mice received an intravenous (i.v.) adoptive transfer of 1×10$^6$ activated pmel-1 splenocytes +gp100$_{25-33}$ peptide pulsed dendritic cells subcutaneously (s.c) and 500,000 IU of human recombinant IL-2. Experimental mice also received a co-adoptive transfer of 1×10$^5$ CD4+FoxP3+ suppressor cells or 1×10$^6$ CD4+ FoxP3-helper T-cells isolated from the FoxP3-EGFP transgenic mice. At day +25 after tumor challenge, B16 tumors in mice-transferred pmel-1 cells were significantly smaller (p<0.000001) than XRT controls; however, there was no significant difference between mice receiving pmel-1 alone, pmel-1+Treg, or pmel-1+CD4+ FoxP3-cells (p>0.05). The results indicate that the addition of 10$^5$ Foxp3(+) CD4 spleen cells to conditioned mice did not adversely impact antitumor activity by pmel. Addition of 10$^5$ Foxp3(−) CD4 T helper cells to conditioned mice did not have a statistically significant improvement in antitumor activity, although the onset of tumor growth appeared to be further delayed.

These studies illustrate that having Treg cells in the adoptive transfer procedure does not interfere with the anti-tumor benefits of T cell adoptive transfer. The data supports an embodiment to isolate patient CD8 cells, transduce them with MART-1 TCR and recombine the transduced CD8 cells with untransduced PBMC prior to adoptive transfer of the cell population into patients. The transduced CD8 cells and untransduced PBMC cells can be combined at a ratio of 1:1 prior to adoptive transfer into patients.

EXAMPLE 9

Adoptive Therapy OF MART-1 T Cell Receptor for Treatment of Melanoma

Figure 10:
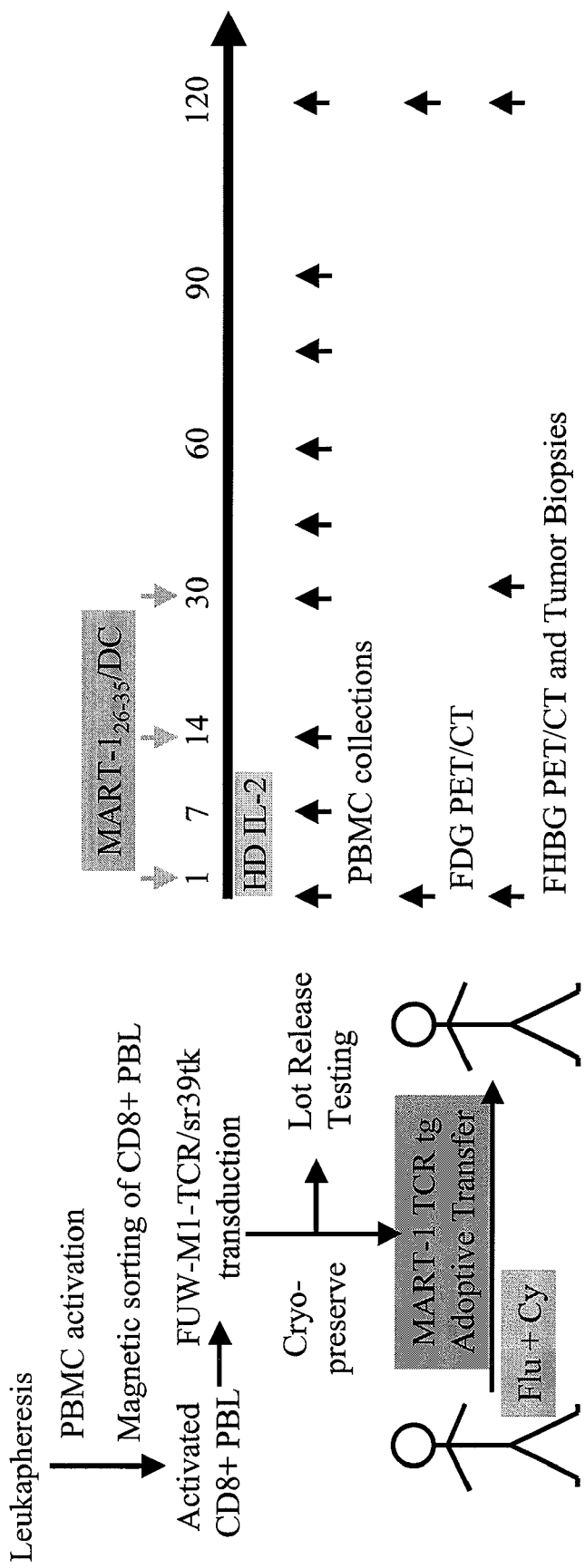
FIG. 10 shows a schematic of an embodiment for a therapeutic procedure. Patients undergo leukapheresis to collect PBMC, which are activated in vitro. Selected CD8+ cells are transduced with M1 lentivirus and cryopreserved. Once the transduced cells have undergone lot release testing, patients receive conditioning chemotherapy, and M1 TCR/sr39tk transgenic T cells are infused. Patients then receive MART-1/DC vaccines and IL-2 and undergo repeated peripheral blood sampling, PET CT scanning and biopsies of tumor deposits.

HLA-A*0201-positive patients with MART-1-positive 1 metastatic melanoma undergo a first leukapheresis to collect peripheral blood mononuclear cells (PBMC). The PBMC are activated for 2 days with CD2/CD3/CD28 beads from Miltenyi. Following activation, CD8+ CTL are selected using clinical grade magnetic columns. The isolated CD8+ CTL are transduced with the FUW-M1-TCR/sr39tk lentivirus (Example 2). Transduced cells are cryopreserved to allow time for adequate lot release testing. A second leukapheresis is performed to collect PBMC for DC manufacture The patients receive a nonmyeloablative but lymphocyte depleting chemotherapy conditioning regimen consisting of cyclophosphamide and fludarabine. The patients then receive the adoptive transfer of the 1:1 mixture of transduced CD8+ T cells/unmanipulated PBMCs by intravenous infusion. Subsets (n=3) of patients within the group receive escalated numbers of transduced CD8+ T cells, as outlined in Table 2. Following adoptive cell transfer, all patients receive MART-$1_{26\text{-}35}$ peptide-pulsed DC vaccines and high doses of interleukin-2 (IL-2). $10^7$ (ten million) MART-$1_{26\text{-}35}$ peptide pulsed DC are administered intradermally close to a lymph node basin not known to be involved with melanoma. A typical high doses of IL-2 is an intravenous administration of 600,000 IU IL-2/kg over 15 minutes every eight hours for up to 14 doses, as tolerated, following the UCLA standard protocol (Figlin et al. 1997. *Ca J Sci Am*, which is incorporated herein by reference in its entirety). The patients also undergo repeated peripheral blood sampling, PET CT scanning procedures and biopsies of tumor deposits according to standard procedures known in the art. FIG. 10 outlines the adoptive therapy procedure.

TABLE 2

Escalating Dose Schedule of Patient Subsets

| Subset | No. Patients | Flu + Cy Conditioning | No. of Gene-modified CD8+ T Cells Reinfused * |
|---|---|---|---|
| A | 3 (+3) | No | $<1 \times 10^7$ |
| B | 3 (+3) | Yes | $<1 \times 10^7$ |
| C | 3 (+3) | Yes | $<1 \times 10^8$ |
| D | 3 to 12 | Yes | $1 \times 10^9$ (or max. available) |

* recombined with an equal number of unmanipulated PBMC

The patients are evaluated to determine the maximum tolerated dose (MTD), safety and toxicity profile of three escalating doses of transduced autologous CD8+ T cells followed by IL-2 and MART-$1_{26\text{-}35}$ peptide-pulsed DCs in patients with locally advanced or metastatic melanoma receiving a lymphodepleting preparative regimen. The chemotherapy conditioning regimen includes cyclophosphamide administered intravenously at 60 mg/kg/day for 2 days and fludarabine administered intravenously at 25 mg/m2/day for 5 days. Myelodepleting conditioning regimens adding total body irradiation (TBI) to the chemotherapy conditioning are also be considered. The persistence of transduced CD8+ T cells is also determined in the serial peripheral blood samples. Samples for immune monitoring are collected for the secondary endpoints of MART-1 TCR transgenic T cell persistence, replication competent lentivirus analysis, lentivirus insertion sites in dominant clones, immunological monitoring assays and analysis of anti-sr39tk immunological responses. Furthermore, serial in vivo imaging using [$^{18}$F]FHBG PET is compared and correlated with blood samples and tumor biopsies at different intervals after adoptive transfer.

In addition, the clinical response of patients to the combined therapy of adoptive transfer of FUW-M1-TCR/sr39tk engineered T cells, MART-$1_{26\text{-}35}$ peptide pulsed DC and high dose IL-2 to induce objective tumor regressions in patients with locally advanced or metastatic melanoma is evaluated. The evaluation is conducted by comparing standard CT and [$^{18}$F]FHBG PET imaging scans from baseline with scans obtained periodically after the T cell adoptive transfer. Standard RECIST tumor response criteria are used to determine target lesions and clinical response.

The total duration of the study is between 24-36 months. A durable response rate on the order of approximately 20 to 30% is observed in patients undergoing MART-1 TCR adoptive immunotherapy in the form of improved clinical symptoms and regression of tumor size relative to those patients who do not undergo MART-1 TCR adoptive immunotherapy.

What is claimed is:

1. An isolated polypeptide comprising an amino acid sequence with at least 95% sequence identity to SEQ ID NO: 3, wherein the variable region of the polypeptide consists of SEQ ID NO: 4.

2. The isolated polypeptide of claim 1, wherein the polypeptide comprises the amino acid sequence of SEQ ID NO: 3.

3. A transfected cell comprising:
a T-cell receptor comprising an α subunit with at least 95% sequence identity to SEQ ID NO: 3 and a β subunit with at least 95% sequence identity to SEQ ID NO:7, wherein the variable region of the α subunit consists of SEQ ID NO: 4, and wherein the variable region of the β subunit consists of SEQ ID NO: 8.

4. A T-cell receptor, comprising:
an α subunit; and
a β subunit,
wherein the α subunit comprises an amino acid sequence with at least 95% sequence identity to SEQ ID NO: 3 and the β subunit comprises an amino acid with at least 95% sequence identity to SEQ ID NO:7, wherein the variable region of the α subunit consists of SEQ ID NO: 4, and wherein the variable region of the β subunit consists of SEQ ID NO: 8.

5. The isolated polypeptide of claim 1, wherein the polypeptide comprises an amino acid sequence with at least 99% sequence identity to SEQ ID NO: 3.

6. The isolated polypeptide of claim 1, wherein the polypeptide comprises the amino acid sequence of SEQ ID NO: 3.

7. The transfected cell of claim 3, wherein the α subunit has at least 99% sequence identity to SEQ ID NO: 3.

8. The transfected cell of claim 3, wherein the α subunit consists of the amino acid sequence of SEQ ID NO: 3.

9. The transfected cell of claim 3, wherein the β subunit has at least 99% sequence identity to SEQ ID NO:7.

10. The transfected cell of claim 3, wherein the β subunit consists of the amino acid sequence of SEQ ID NO: 7.

11. The T-cell receptor of claim 4, wherein the α subunit has at least 99% sequence identity to SEQ ID NO: 3.

12. The T-cell receptor of claim 4, wherein the α subunit consists of the amino acid sequence of SEQ ID NO: 3.

13. The T-cell receptor of claim 4, wherein the β subunit has at least 99% sequence identity to SEQ ID NO:7.

14. The T-cell receptor of claim 4, wherein the β subunit consists of the amino acid sequence of SEQ ID NO: 7.

* * * * *

SEQUENCE LISTING

<160> NUMBER OF SEQ ID NOS: 21

<210> SEQ ID NO 1
<211> LENGTH: 825
<212> TYPE: DNA
<213> ORGANISM: Artificial Sequence
<220> FEATURE:
<223> OTHER INFORMATION: Cloned nucleic acid sequence from Homo sapiens

<400> SEQUENCE: 1

```
atgatgaaat ccttgagagt tttactggtg atcctgtggc ttcagttaag ctgggtttgg        60
agccaacaga aggaggtgga gcaggatcct ggaccactca gtgttccaga gggagccatt       120
gtttctctca actgcactta cagcaacagt gcttttcaat acttcatgtg gtacagacag       180
tattccagaa aaggccctga gttgctgatg tacacatact ccagtggtaa caaagaagat       240
ggaaggttta cagcacaggt cgataaatcc agcaagtata tctccttgtt catcagagac       300
tcacagccca gtgattcagc cacctacctc tgtgcaatga gcgagactgg aggcttcaaa       360
actatctttg gagcaggaac aagactattt gttaaagcaa atatccagaa ccctgaccct       420
gccgtgtacc agctgagaga ctctaaatcc agtgacaagt ctgtctgcct attcaccgat       480
```

-continued

```
tttgattctc aaacaaatgt gtcacaaagt aaggattctg atgtgtatat cacagacaaa      540
actgtgctag acatgaggtc tatggacttc aagagcaaca gtgctgtggc ctggagcaac      600
aaatctgact ttgcatgtgc aaacgccttc aacaacagca ttattccaga agacaccttc      660
ttccccagcc cagaaagttc ctgtgatgtc aagctggtcg agaaaagctt tgaaacagat      720
acgaacctaa actttcaaaa cctgtcagtg attgggttcc gaatcctcct cctgaaagtg      780
gccgggttta atctgctcat gacgctgcgg ctgtggtcca gctga                      825
```

```
<210> SEQ ID NO 2
<211> LENGTH: 347
<212> TYPE: DNA
<213> ORGANISM: Artificial Sequence
<220> FEATURE:
<223> OTHER INFORMATION: Cloned nucleic acid sequence from Homo
      sapiens

<400> SEQUENCE: 2
```

```
gggtttggag ccaacagaag gaggtggagc aggatcctgg accactcagt gttccagagg       60
gagccattgt ttctctcaac tgcacttaca gcaacagtgc ttttcaatac ttcatgtggt      120
acagacagta ttccagaaaa ggccctgagt tgctgatgta cacatactcc agtggtaaca      180
aagaagatgg aaggtttaca gcacaggtcg ataaatccag caagtatatc tccttgttca      240
tcagagactc acagcccagt gattcagcca cctacctctg tgcaatgagc gagactggag      300
gcttcaaaac tatctttgga gcaggaacaa gactatttgt taaagca                    347
```

```
<210> SEQ ID NO 3
<211> LENGTH: 274
<212> TYPE: PRT
<213> ORGANISM: Artificial Sequence
<220> FEATURE:
<223> OTHER INFORMATION: Protein expressed from cloned nucleic acid
      sequence from Homo sapiens

<400> SEQUENCE: 3
```

```
Met Met Lys Ser Leu Arg Val Leu Leu Val Ile Leu Trp Leu Gln Leu
  1               5                  10                  15

Ser Trp Val Trp Ser Gln Gln Lys Glu Val Glu Gln Asp Pro Gly Pro
             20                  25                  30

Leu Ser Val Pro Glu Gly Ala Ile Val Ser Leu Asn Cys Thr Tyr Ser
         35                  40                  45

Asn Ser Ala Phe Gln Tyr Phe Met Trp Tyr Arg Gln Tyr Ser Arg Lys
     50                  55                  60

Gly Pro Glu Leu Leu Met Tyr Thr Tyr Ser Ser Gly Asn Lys Glu Asp
 65                  70                  75                  80

Gly Arg Phe Thr Ala Gln Val Asp Lys Ser Ser Lys Tyr Ile Ser Leu
                 85                  90                  95

Phe Ile Arg Asp Ser Gln Pro Ser Asp Ser Ala Thr Tyr Leu Cys Ala
            100                 105                 110

Met Ser Glu Thr Gly Gly Phe Lys Thr Ile Phe Gly Ala Gly Thr Arg
        115                 120                 125

Leu Phe Val Lys Ala Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
```

```
                    180                 185                 190
Asn Ser Ala Val Ala Trp Ser Asn Lys Ser Asp Phe Cys Ala Asn
            195                 200                 205
Ala Phe Asn Asn Ser Ile Ile Pro Glu Asp Thr Phe Pro Ser Pro
        210                 215                 220
Glu Ser Ser Cys Asp Val Lys Leu Val Glu Lys Ser Phe Glu Thr Asp
225                 230                 235                 240
Thr Asn Leu Asn Phe Gln Asn Leu Ser Val Ile Gly Phe Arg Ile Leu
                245                 250                 255
Leu Leu Lys Val Ala Gly Phe Asn Leu Leu Met Thr Leu Arg Leu Trp
            260                 265                 270
Ser Ser

<210> SEQ ID NO 4
<211> LENGTH: 116
<212> TYPE: PRT
<213> ORGANISM: Artificial Sequence
<220> FEATURE:
<223> OTHER INFORMATION: Protein expressed from cloned nucleic acid
      sequence from Homo sapiens

<400> SEQUENCE: 4

Trp Val Trp Ser Gln Gln Lys Glu Val Glu Gln Asp Pro Gly Pro Leu
1               5                   10                  15
Ser Val Pro Glu Gly Ala Ile Val Ser Leu Asn Cys Thr Tyr Ser Asn
            20                  25                  30
Ser Ala Phe Gln Tyr Phe Met Trp Tyr Arg Gln Tyr Ser Arg Lys Gly
        35                  40                  45
Pro Glu Leu Leu Met Tyr Thr Tyr Ser Ser Gly Asn Lys Glu Asp Gly
    50                  55                  60
Arg Phe Thr Ala Gln Val Asp Lys Ser Ser Lys Tyr Ile Ser Leu Phe
65                  70                  75                  80
Ile Arg Asp Ser Gln Pro Ser Asp Ser Ala Thr Tyr Leu Cys Ala Met
                85                  90                  95
Ser Glu Thr Gly Gly Phe Lys Thr Ile Phe Gly Ala Gly Thr Arg Leu
            100                 105                 110
Phe Val Lys Ala
        115

<210> SEQ ID NO 5
<211> LENGTH: 933
<212> TYPE: DNA
<213> ORGANISM: Artificial Sequence
<220> FEATURE:
<223> OTHER INFORMATION: Cloned nucleic acid sequence from Homo
      sapiens

<400> SEQUENCE: 5
atgggccccc agctccttgg ctatgtggtc ctttgccttc taggagcagg ccccctggaa      60
gcccaagtga cccagaaccc aagatacctc atcacagtga ctggaaagaa gttaacagtg    120
acttgttctc agaatatgaa ccatgagtat atgtcctggt atcgacaaga cccagggctg    180
ggcttaaggc agatctacta ttcaatgaat gttgaggtga ctgataaggg agatgttcct    240
gaagggtaca agtctctcg aaaagagaag aggaatttcc ccctgatcct ggagtcgccc    300
agccccaacc agacctctct gtacttctgt gccagcagtt tagtagggac agcggggtca    360
cccctccact tgggaacgg gaccaggctc actgtgacag aggacctgaa caaggtgttc    420 ccaccccgagg tcgctgtgtt tgagccatca gaagcagaga tctcccacac ccaaaaggcc    480
```

```
acactggtgt gcctggccac aggcttcttc cctgaccacg tggagctgag ctggtgggtg      540
aatgggaagg aggtgcacag tggggtcagc acggacccgc agcccctcaa ggagcagccc      600
gccctcaatg actccagata ctgcctgagc agccgcctga gggtctcggc caccttctgg      660
cagaaccccc gcaaccactt ccgctgtcaa gtccagttct acgggctctc ggagaatgac      720
gagtggaccc aggatagggc caaacccgtc acccagatcg tcagcgccga ggcctggggt      780
agagcagact gtggctttac ctcggtgtcc taccagcaag gggtcctgtc tgccaccatc      840
ctctatgaga tcctgctagg gaaggccacc ctgtatgctg tgctggtcag cgcccttgtg      900
ttgatggcca tggtcaagag aaaggatttc tga                                   933
```

<210> SEQ ID NO 6
<211> LENGTH: 350
<212> TYPE: DNA
<213> ORGANISM: Artificial Sequence
<220> FEATURE:
<223> OTHER INFORMATION: Cloned nucleic acid sequence from Homo
      sapiens

<400> SEQUENCE: 6

```
gcccctggaa gcccaagtg acccagaacc caagatacct catcacagtg actggaaaga       60
agttaacagt gacttgttct cagaatatga accatgagta tatgtcctgg tatcgacaag      120
acccagggct gggcttaagg cagatctact attcaatgaa tgttgaggtg actgataagg      180
gagatgttcc tgaagggtac aaagtctctc gaaaagagaa gaggaatttc cccctgatcc      240
tggagtcgcc cagccccaac cagacctctc tgtacttctg tgccagcagt ttagtaggga      300
cagcggggtc acccctccac tttgggaacg ggaccaggct cactgtgaca                 350
```

<210> SEQ ID NO 7
<211> LENGTH: 310
<212> TYPE: PRT
<213> ORGANISM: Artificial Sequence
<220> FEATURE:
<223> OTHER INFORMATION: Protein expressed from cloned nucleic acid
      sequence from Homo sapiens

<400> SEQUENCE: 7

```
Met Gly Pro Gln Leu Leu Gly Tyr Val Val Leu Cys Leu Leu Gly Ala
  1               5                  10                  15

Gly Pro Leu Glu Ala Gln Val Thr Gln Asn Pro Arg Tyr Leu Ile Thr
             20                  25                  30

Val Thr Gly Lys Lys Leu Thr Val Thr Cys Ser Gln Asn Met Asn His
         35                  40                  45

Glu Tyr Met Ser Trp Tyr Arg Gln Asp Pro Gly Leu Gly Leu Arg Gln
     50                  55                  60

Ile Tyr Tyr Ser Met Asn Val Glu Val Thr Asp Lys Gly Asp Val Pro
 65                  70                  75                  80

Glu Gly Tyr Lys Val Ser Arg Lys Glu Lys Arg Asn Phe Pro Leu Ile
                 85                  90                  95

Leu Glu Ser Pro Ser Pro Asn Gln Thr Ser Leu Tyr Phe Cys Ala Ser
            100                 105                 110

Ser Leu Val Gly Thr Ala Gly Ser Pro Leu His Phe Gly Asn Gly Thr
        115                 120                 125

Arg Leu Thr Val Thr Glu Asp Leu Asn Lys Val Phe Pro Pro Glu Val
    130                 135                 140

Ala Val Phe Glu Pro Ser Glu Ala Glu Ile Ser His Thr Gln Lys Ala
145                 150                 155                 160
```

```
Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe
305                 310

<210> SEQ ID NO 8
<211> LENGTH: 117
<212> TYPE: PRT
<213> ORGANISM: Artificial Sequence
<220> FEATURE:
<223> OTHER INFORMATION: Protein expressed from cloned nucleic acid
      sequence from Homo sapiens

<400> SEQUENCE: 8

Gly Pro Leu Glu Ala Gln Val Thr Gln Asn Pro Arg Tyr Leu Ile Thr
1               5                   10                  15

Val Thr Gly Lys Lys Leu Thr Val Thr Cys Ser Gln Asn Met Asn His
            20                  25                  30

Glu Tyr Met Ser Trp Tyr Arg Gln Asp Pro Gly Leu Gly Leu Arg Gln
        35                  40                  45

Ile Tyr Tyr Ser Met Asn Val Glu Val Thr Asp Lys Gly Asp Val Pro
    50                  55                  60

Glu Gly Tyr Lys Val Ser Arg Lys Glu Lys Arg Asn Phe Pro Leu Ile
65                  70                  75                  80

Leu Glu Ser Pro Ser Pro Asn Gln Thr Ser Leu Tyr Phe Cys Ala Ser
                85                  90                  95

Ser Leu Val Gly Thr Ala Gly Ser Pro Leu His Phe Gly Asn Gly Thr
            100                 105                 110

Arg Leu Thr Val Thr
        115

<210> SEQ ID NO 9
<211> LENGTH: 825
<212> TYPE: DNA
<213> ORGANISM: Artificial Sequence
<220> FEATURE:
<223> OTHER INFORMATION: Cloned nucleic acid sequence from Homo
      sapiens

<400> SEQUENCE: 9
atgatgaaat ccttgagagt tttactagtg atcctgtggc ttcagttgag ctgggtttgg      60
agccaacaga aggaggtgga gcagaattct ggaccccctca gtgttccaga gggagccatt     120
```

```
gcctctctca actgcactta cagtgaccga ggttcccagt ccttcttctg gtacagacaa      180
tattctggga aaagccctga gttgataatg ttcatatact ccaatggtga caagaagat       240 ggaaggttta cagcacagct caataaagcc agccagtatg tttctctgct catcagagac      300
tcccagccca gtgattcagc cacctacctc tgtgccgtga acataggctt tgggaatgtg      360
ctgcattgcg ggtccggcac tcaagtgatt gttttaccac atatccagaa ccctgaccct      420
gccgtgtacc agctgagaga ctctaaatcc agtgacaagt ctgtctgcct attcaccgat      480
tttgattctc aaacaaatgt gtcacaaagt aaggattctg atgtgtatat cacagacaaa      540
actgtgctag acatgaggtc tatggacttc aagagcaaca gtgctgtggc ctggagcaac      600
aaatctgact ttgcatgtgc aaacgccttc aacaacagca ttattccaga agacaccttc      660
ttccccagcc cagaaagttc ctgtgatgtc aagctggtcg agaaaagctt tgaaacagat      720
acgaacctaa actttcaaaa cctgtcagtg attgggttcc gaatcctcct cctgaaagtg      780
gccgggttta atctgctcat gacgctgcgg ctgtggtcca gctga                      825

<210> SEQ ID NO 10
<211> LENGTH: 347
<212> TYPE: DNA
<213> ORGANISM: Artificial Sequence
<220> FEATURE:
<223> OTHER INFORMATION: Cloned nucleic acid sequence from Homo
      sapiens

<400> SEQUENCE: 10
gggtttggag ccaacagaag gaggtggagc agaattctgg acccctcagt gttccagagg       60
gagccattgc ctctctcaac tgcacttaca gtgaccgagg ttcccagtcc ttcttctggt      120
acagacaata ttctgggaaa agccctgagt tgataatgtt catatactcc aatggtgaca      180
aagaagatgg aaggtttaca gcacagctca ataaagccag ccagtatgtt tctctgctca      240
tcagagactc ccagcccagt gattcagcca cctacctctg tgccgtgaac ataggctttg      300
ggaatgtgct gcattgcggg tccggcactc aagtgattgt tttacca                    347

<210> SEQ ID NO 11
<211> LENGTH: 274
<212> TYPE: PRT
<213> ORGANISM: Artificial Sequence
<220> FEATURE:
<223> OTHER INFORMATION: Protein expressed from cloned nucleic acid
      sequence from Homo sapiens

<400> SEQUENCE: 11

Met Met Lys Ser Leu Arg Val Leu Leu Val Ile Leu Trp Leu Gln Leu
  1               5                  10                  15

Ser Trp Val Trp Ser Gln Gln Lys Glu Val Glu Gln Asn Ser Gly Pro
             20                  25                  30

Leu Ser Val Pro Glu Gly Ala Ile Ala Ser Leu Asn Cys Thr Tyr Ser
         35                  40                  45

Asp Arg Gly Ser Gln Ser Phe Phe Trp Tyr Arg Gln Tyr Ser Gly Lys
     50                  55                  60

Ser Pro Glu Leu Ile Met Phe Ile Tyr Ser Asn Gly Asp Lys Glu Asp
 65                  70                  75                  80

Gly Arg Phe Thr Ala Gln Leu Asn Lys Ala Ser Gln Tyr Val Ser Leu
                 85                  90                  95

Leu Ile Arg Asp Ser Gln Pro Ser Asp Ser Ala Thr Tyr Leu Cys Ala
            100                 105                 110
```

Val Asn Ile Gly Phe Gly Asn Val Leu His Cys Gly Ser Gly Thr Gln
        115                 120                 125

Val Ile Val Leu Pro His Ile Gln Asn Pro Asp Pro Ala Val Tyr Gln
130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 12
<211> LENGTH: 116
<212> TYPE: PRT
<213> ORGANISM: Artificial Sequence
<220> FEATURE:
<223> OTHER INFORMATION: Protein expressed from cloned nucleic acid
      sequence from Homo sapiens

<400> SEQUENCE: 12

Trp Val Trp Ser Gln Gln Lys Glu Val Glu Gln Asn Ser Gly Pro Leu
1               5                   10                  15

Ser Val Pro Glu Gly Ala Ile Ala Ser Leu Asn Cys Thr Tyr Ser Asp
            20                  25                  30

Arg Gly Ser Gln Ser Phe Phe Trp Tyr Arg Gln Tyr Ser Gly Lys Ser
        35                  40                  45

Pro Glu Leu Ile Met Phe Ile Tyr Ser Asn Gly Asp Lys Glu Asp Gly
    50                  55                  60

Arg Phe Thr Ala Gln Leu Asn Lys Ala Ser Gln Tyr Val Ser Leu Leu
65                  70                  75                  80

Ile Arg Asp Ser Gln Pro Ser Asp Ser Ala Thr Tyr Leu Cys Ala Val
                85                  90                  95

Asn Ile Gly Phe Gly Asn Val Leu His Cys Gly Ser Gly Thr Gln Val
            100                 105                 110

Ile Val Leu Pro
        115

<210> SEQ ID NO 13
<211> LENGTH: 930
<212> TYPE: DNA
<213> ORGANISM: Artificial Sequence
<220> FEATURE:
<223> OTHER INFORMATION: Cloned nucleic acid sequence from Homo
      sapiens

<400> SEQUENCE: 13
atgggccccc agctccttgg ctatgtggtc ctttgccttc taggagcagg cccccctgga a      60

-continued

```
gcccaagtga cccagaaccc aagatacctc atcacagtga ctggaaagaa gttaacagtg      120
acttgttctc agaatatgaa ccatgagtat atgtcctggt atcgacaaga cccagggctg      180
ggcttaaggc agatctacta ttcaatgaat gttgaggtga ctgataaggg agatgttcct      240
gaagggtaca aagtctctcg aaaagagaag aggaatttcc ccctgatcct ggagtcgccc      300
agccccaacc agacctctct gtacttctgt gccagcagcc tagaggtggt aggcaatgag      360
cagttcttcg ggccagggac acggctcacc gtgctagagg acctgaaaaa cgtgttccca      420
cccgaggtcg ctgtgtttga gccatcagaa gcagagatct cccacaccca aaaggccaca      480
ctggtgtgcc tggccacagg cttctacccc gaccacgtgg agctgagctg gtgggtgaat      540
gggaaggagg tgcacagtgg ggtcagcaca gacccgcagc ccctcaagga gcagcccgcc      600
ctcaatgact ccagatactg cctgagcagc cgcctgaggg tctcggccac cttctggcag      660
aaccccgca accacttccg ctgtcaagtc cagttctacg ggctctcgga gaatgacgag       720
tggacccagg atagggccaa acccgtcacc cagatcgtca gcgccgaggc tggggtaga       780
gcagactgtg gctttaccct ggtgtcctac cagcaagggg tcctgtctgc caccatcctc      840
tatgagatcc tgctagggaa ggccacccct atgctgtgc tggtcagcgc ccttgtgttg       900
atggccatgg tcaagagaaa ggatttctga                                       930
```

<210> SEQ ID NO 14
<211> LENGTH: 347
<212> TYPE: DNA
<213> ORGANISM: Artificial Sequence
<220> FEATURE:
<223> OTHER INFORMATION: Cloned nucleic acid sequence from Homo
      sapiens

<400> SEQUENCE: 14

```
gcccctgga agcccaagtg acccagaacc caagatacct catcacagtg actggaaaga       60
agttaacagt gacttgttct cagaatatga accatgagta tatgtcctgg tatcgacaag      120
acccagggct gggcttaagg cagatctact attcaatgaa tgttgaggtg actgataagg      180
gagatgttcc tgaagggtac aaagtctctc gaaaagagaa gaggaatttc ccctgatcc       240
tggagtcgcc cagccccaac cagacctctc tgtacttctg tgccagcagc ctagaggtgg      300
taggcaatga gcagttcttc gggccaggga cacggctcac cgtgcta                    347
```

<210> SEQ ID NO 15
<211> LENGTH: 309
<212> TYPE: PRT
<213> ORGANISM: Artificial Sequence
<220> FEATURE:
<223> OTHER INFORMATION: Protein expressed from cloned nucleic acid
      sequence from Homo sapiens

<400> SEQUENCE: 15

```
Met Gly Pro Gln Leu Leu Gly Tyr Val Val Leu Cys Leu Leu Gly Ala
 1               5                  10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
```

```
                    85                  90                  95
Leu Glu Ser Pro Ser Pro Asn Gln Thr Ser Leu Tyr Phe Cys Ala Ser
                100                 105                 110

Ser Leu Glu Val Val Gly Asn Glu Gln Phe Phe Gly Pro Gly Thr Arg
            115                 120                 125

Leu Thr Val Leu Glu Asp Leu Lys Asn Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe
305

<210> SEQ ID NO 16
<211> LENGTH: 116
<212> TYPE: PRT
<213> ORGANISM: Artificial Sequence
<220> FEATURE:
<223> OTHER INFORMATION: Protein expressed from cloned nucleic acid
      sequence from Homo sapiens

<400> SEQUENCE: 16

Gly Pro Leu Glu Ala Gln Val Thr Gln Asn Pro Arg Tyr Leu Ile Thr
1               5                   10                  15

Val Thr Gly Lys Lys Leu Thr Val Thr Cys Ser Gln Asn Met Asn His
            20                  25                  30

Glu Tyr Met Ser Trp Tyr Arg Gln Asp Pro Gly Leu Gly Leu Arg Gln
        35                  40                  45

Ile Tyr Tyr Ser Met Asn Val Glu Val Thr Asp Lys Gly Asp Val Pro
    50                  55                  60

Glu Gly Tyr Lys Val Ser Arg Lys Glu Lys Arg Asn Phe Pro Leu Ile
65                  70                  75                  80

Leu Glu Ser Pro Ser Pro Asn Gln Thr Ser Leu Tyr Phe Cys Ala Ser
                85                  90                  95

Ser Leu Glu Val Val Gly Asn Glu Gln Phe Phe Gly Pro Gly Thr Arg
            100                 105                 110

Leu Thr Val Leu
        115
```

<210> SEQ ID NO 17
<211> LENGTH: 12264
<212> TYPE: DNA
<213> ORGANISM: Artificial Sequence
<220> FEATURE:
<223> OTHER INFORMATION: Cloned nucleic acid sequence from Homo sapiens

<400> SEQUENCE: 17

| | | | | | |
|---|---|---|---|---|---|
| ttgtacaaag | tggtgataac | ctcgagggcg | cgccgaattc | gatatcaagc | ttatcgataa | 60 |
| tcaacctctg | gattacaaaa | tttgtgaaag | attgactggt | attcttaact | atgttgctcc | 120 |
| ttttacgcta | tgtggatacg | ctgctttaat | gcctttgtat | catgctattg | cttcccgtat | 180 |
| ggctttcatt | ttctcctcct | tgtataaatc | ctggttgctg | tctctttatg | aggagttgtg | 240 |
| gcccgttgtc | aggcaacgtg | gcgtggtgtg | cactgtgttt | gctgacgcaa | cccccactgg | 300 |
| ttggggcatt | gccaccacct | gtcagctcct | ttccgggact | ttcgctttcc | cctccctat | 360 |
| tgccacggcg | gaactcatcg | ccgcctgcct | tgcccgctgc | tggacagggg | ctcggctgtt | 420 |
| gggcactgac | aattccgtgg | tgttgtcggg | gaaatcatcg | tcctttcctt | ggctgctcgc | 480 |
| ctgtgttgcc | acctggattc | tgcgcgggac | gtccttctgc | tacgtccctt | cggccctcaa | 540 |
| tccagcggac | cttccttccc | gcggcctgct | gccggctctg | cggcctcttc | cgcgtcttcg | 600 |
| ccttcgccct | cagacgagtc | ggatctccct | ttgggccgcc | tccccgcatc | gataccgtcg | 660 |
| acctcgagac | ctagaaaaac | atggagcaat | cacaagtagc | aatacagcag | ctaccaatgc | 720 |
| tgattgtgcc | tggctagaag | cacaagagga | ggaggaggtg | gttttccag | tcacacctca | 780 |
| ggtacccttta | agaccaatga | cttacaaggc | agctgtagat | cttagccact | ttttaaaaga | 840 |
| aaagggggga | ctggaagggc | taattcactc | ccaacgaaga | caagatatcc | ttgatctgtg | 900 |
| gatctaccac | acacaaggct | acttccctga | ttggcagaac | tacacaccag | ggccagggat | 960 |
| cagatatcca | ctgacctttg | gatggtgcta | caagctagta | ccagttgagc | aagagaaggt | 1020 |
| agaagaagcc | aatgaaggag | agaacacccg | cttgttacac | cctgtgagcc | tgcatgggat | 1080 |
| ggatgacccg | gagagagaag | tattagagtg | gaggtttgac | agccgcctag | catttcatca | 1140 |
| catggcccga | gagctgcatc | cggactgtac | tgggtctctc | tggttagacc | agatctgagc | 1200 |
| ctgggagctc | tctggctaac | tagggaaccc | actgcttaag | cctcaataaa | gcttgccttg | 1260 |
| agtgcttcaa | gtagtgtgtg | cccgtctgtt | gtgtgactct | ggtaactaga | gatccctcag | 1320 |
| acccttttag | tcagtgtgga | aaatctctag | cagggcccgt | ttaaacccgc | tgatcagcct | 1380 |
| cgactgtgcc | ttctagttgc | cagccatctg | ttgtttgccc | ctcccccgtg | ccttccttga | 1440 |
| ccctggaagg | tgccactccc | actgtccttt | cctaataaaa | tgaggaaatt | gcatcgcatt | 1500 |
| gtctgagtag | tgtcattct | attctggggg | gtggggtggg | gcaggacagc | aaggggagg | 1560 |
| attgggaaga | caatagcagg | catgctgggg | atgcggtggg | ctctatggct | tctgaggcgg | 1620 |
| aaagaaccag | ctggggctct | aggggtatc | cccacgcgcc | ctgtagcggc | gcattaagcg | 1680 |
| cggcgggtgt | ggtggttacg | cgcagcgtga | ccgctacact | tgccagcgcc | ctagcgcccg | 1740 |
| ctcctttcgc | tttcttccct | tcctttctcg | ccacgttcgc | cggctttccc | cgtcaagctc | 1800 |
| taaatcgggg | gctccctttta | gggttccgat | ttagtgcttt | acggcacctc | gaccccaaaa | 1860 |
| aacttgatta | gggtgatggt | tcacgtagtg | gccatcgcc | ctgatagacg | gttttcgcc | 1920 |
| ctttgacgtt | ggagtccacg | ttctttaata | gtggactctt | gttccaaact | ggaacaacac | 1980 |
| tcaaccctat | ctcggtctat | tcttttgatt | tataagggat | tttgccgatt | tcggcctatt | 2040 |
| ggttaaaaaa | tgagctgatt | taacaaaaat | ttaacgcgaa | ttaattctgt | ggaatgtgtg | 2100 |

-continued

```
tcagttaggg tgtggaaagt ccccaggctc cccagcaggc agaagtatgc aaagcatgca   2160
tctcaattag tcagcaacca ggtgtggaaa gtccccaggc tccccagcag gcagaagtat   2220
gcaaagcatg catctcaatt agtcagcaac catagtcccg cccctaactc cgcccatccc   2280
gcccctaact ccgcccagtt ccgcccattc tccgcccat ggctgactaa ttttttttat    2340
ttatgcagag gccgaggccg cctctgcctc tgagctattc cagaagtagt gaggaggctt   2400
ttttggaggc ctaggctttt gcaaaaagct cccgggagct tgtatatcca ttttcggatc   2460
tgatcagcac gtgttgacaa ttaatcatcg gcatagtata tcggcatagt ataatacgac   2520
aaggtgagga actaaaccat ggccaagttg accagtgccg ttccggtgct caccgcgcgc   2580
gacgtcgccg gagcggtcga gttctggacc gaccggctcg ggttctcccg ggacttcgtg   2640
gaggacgact cgccggtgt ggtccgggac gacgtgaccc tgttcatcag cgcggtccag    2700
gaccaggtgg tgccggacaa caccctggcc tgggtgtggg tgcgcggcct ggacgagctg   2760
tacgccgagt ggtcggaggt cgtgtccacg aacttccggg acgcctccgg gccggccatg   2820
accgagatcg gcgagcagcc gtgggggcgg gagttcgccc tgcgcgaccc ggccggcaac   2880
tgcgtgcact tcgtggccga ggagcaggac tgacacgtgc tacgagattt cgattccacc   2940
gccgccttct atgaaaggtt gggcttcgga atcgttttcc gggacgccgg ctggatgatc   3000
ctccagcgcg gggatctcat gctggagttc ttcgcccacc ccaacttgtt tattgcagct   3060
tataatggtt acaaataaag caatagcatc acaaatttca caaataaagc attttttttca  3120 ctgcattcta gttgtggttt gtccaaactc atcaatgtat cttatcatgt ctgtataccg   3180
tcgacctcta gctagagctt ggcgtaatca tggtcatagc tgtttcctgt gtgaaattgt   3240
tatccgctca caattccaca caacatacga gccggaagca taagtgtaa agcctggggt    3300 gcctaatgag tgagctaact cacattaatt gcgttgcgct cactgcccgc tttccagtcg   3360
ggaaacctgt cgtgccagct gcattaatga atcggccaac gcgcggggag aggcggtttg   3420
cgtattgggc gctcttccgc ttcctcgctc actgactcgc tgcgctcggt cgttcggctg   3480
cggcgagcgg tatcagctca ctcaaaggcg gtaatacggt tatccacaga atcaggggat   3540
aacgcaggaa agaacatgtg agcaaaaggc cagcaaaagg ccaggaaccg taaaaaggcc   3600
gcgttgctgg cgttttttcca taggctccgc cccctgacg agcatcacaa aaatcgacgc    3660
tcaagtcaga ggtggcgaaa cccgacagga ctataaagat accaggcgtt ccccctgga    3720 agctccctcg tgcgctctcc tgttccgacc ctgccgctta ccggatacct gtccgccttt   3780
ctcccttcgg gaagcgtggc gctttctcat agctcacgct gtaggtatct cagttcggtg   3840
taggtcgttc gctccaagct gggctgtgtg cacgaacccc ccgttcagcc cgaccgctgc   3900
gccttatccg gtaactatcg tcttgagtcc aacccggtaa gacacgactt atcgccactg   3960
gcagcagcca ctggtaacag gattagcaga gcgaggtatg taggcggtgc tacagagttc   4020
ttgaagtggt ggcctaacta cggctacact agaagaacag tatttggtat ctgcgctctg   4080
ctgaagccag ttaccttcgg aaaaagagtt ggtagctctt gatccggcaa acaaaccacc   4140
gctggtagcg gtggtttttt tgtttgcaag cagcagatta cgcgcagaaa aaaggatct    4200 caagaagatc ctttgatctt ttctacgggg tctgacgctc agtggaacga aaactcacgt   4260
taagggattt tggtcatgag attatcaaaa aggatcttca cctagatcct ttttaaattaa  4320 aaatgaagtt ttaaatcaat ctaaagtata tatgagtaaa cttggtctga cagttaccaa   4380
tgcttaatca gtgaggcacc tatctcagcg atctgtctat ttcgttcatc catagttgcc   4440
tgactccccg tcgtgtagat aactacgata cgggagggct taccatctgg ccccagtgct   4500
```

```
gcaatgatac cgcgagaccc acgctcaccg gctccagatt tatcagcaat aaaccagcca   4560
gccggaaggg ccgagcgcag aagtggtcct gcaactttat ccgcctccat ccagtctatt   4620
aattgttgcc gggaagctag agtaagtagt tcgccagtta atagtttgcg caacgttgtt   4680
gccattgcta caggcatcgt ggtgtcacgc tcgtcgtttg gtatggcttc attcagctcc   4740
ggttcccaac gatcaaggcg agttacatga tcccccatgt tgtgcaaaaa agcggttagc   4800
tccttcggtc ctccgatcgt tgtcagaagt aagttggccg cagtgttatc actcatggtt   4860
atggcagcac tgcataattc tcttactgtc atgccatccg taagatgctt ttctgtgact   4920
ggtgagtact caaccaagtc attctgagaa tagtgtatgc ggcgaccgag ttgctcttgc   4980
ccggcgtcaa tacgggataa taccgcgcca catagcagaa ctttaaaagt gctcatcatt   5040
ggaaaacgtt cttcggggcg aaaactctca aggatcttac cgctgttgag atccagttcg   5100
atgtaaccca ctcgtgcacc caactgatct tcagcatctt ttactttcac cagcgtttct   5160
gggtgagcaa aaacaggaag gcaaaatgcc gcaaaaaagg gaataagggc gacacggaaa   5220
tgttgaatac tcatactctt cctttttcaa tattattgaa gcatttatca gggttattgt   5280
ctcatgagcg gatacatatt tgaatgtatt tagaaaaata aacaaatagg ggttccgcgc   5340
acatttcccc gaaaagtgcc acctgacgtc gacggatcgg gagatctccc gatccctat    5400 ggtgcactct cagtacaatc tgctctgatg ccgcatagtt aagccagtat ctgctccctg   5460
cttgtgtgtt ggaggtcgct gagtagtgcg cgagcaaaat ttaagctaca acaaggcaag   5520
gcttgaccga caattgcatg aagaatctgc ttagggttag gcgttttgcg ctgcttcgcg   5580
atgtacgggc cagatatacg cgttgacatt gattattgac tagttattaa tagtaatcaa   5640
ttacggggtc attagttcat agcccatata tggagttccg cgttacataa cttacggtaa   5700
atggcccgcc tggctgaccg cccaacgacc cccgcccatt gacgtcaata atgacgtatg   5760
ttcccatagt aacgccaata gggactttcc attgacgtca atgggtggag tatttacggt   5820
aaactgccca cttggcagta catcaagtgt atcatatgcc aagtacgccc cctattgacg   5880
tcaatgacgg taaatggccc gcctggcatt atgcccagta catgacctta tgggactttc   5940
ctacttggca gtacatctac gtattagtca tcgctattac catggtgatg cggttttggc   6000
agtacatcaa tgggcgtgga tagcggtttg actcacgggg atttccaagt ctccacccca   6060
ttgacgtcaa tgggagtttg ttttggcacc aaaatcaacg ggactttcca aaatgtcgta   6120
acaactccgc cccattgacg caaatgggcg gtaggcgtgt acggtgggag gtctatataa   6180
gcagcgcgtt ttgcctgtac tgggtctctc tggttagacc agatctgagc ctgggagctc   6240
tctggctaac tagggaaccc actgcttaag cctcaataaa gcttgccttg agtgcttcaa   6300
gtagtgtgtg cccgtctgtt gtgtgactct ggtaactaga gatccctcag acccttttag   6360
tcagtgtgga aaatctctag cagtggcgcc cgaacaggga cttgaaagcg aaagggaaac   6420
cagaggagct ctctcgacgc aggactcggc ttgctgaagc gcgcacggca agaggcgagg   6480
ggcggcgact ggtgagtacg ccaaaaattt tgactagcgg aggctagaag gagagagatg   6540
ggtgcgagag cgtcagtatt aagcggggga gaattagatc gcgatgggaa aaaattcggt   6600
taaggccagg gggaaagaaa aaatataaat taaaacatat agtatgggca agcagggagc   6660
tagaacgatt cgcagttaat cctggcctgt tagaaacatc agaaggctgt agacaaatac   6720
tgggacagct acaaccatcc cttcagacag gatcagaaga acttagatca ttatataata   6780
cagtagcaac cctctattgt gtgcatcaaa ggatagagat aaaagacacc aaggaagctt   6840
tagacaagat agaggaagag caaaacaaaa gtaagaccac cgcacagcaa gcggccgctg   6900
```

```
atcttcagac ctggaggagg agatatgagg gacaattgga gaagtgaatt atataaatat   6960
aaagtagtaa aaattgaacc attaggagta gcacccacca aggcaaagag aagagtggtg   7020
cagagagaaa aaagagcagt gggaatagga gctttgttcc ttgggttctt gggagcagca   7080
ggaagcacta tgggcgcagc gtcaatgacg ctgacggtac aggccagaca attattgtct   7140
ggtatagtgc agcagcagaa caatttgctg agggctattg aggcgcaaca gcatctgttg   7200
caactcacag tctggggcat caagcagctc caggcaagaa tcctggctgt ggaaagatac   7260
ctaaaggatc aacagctcct ggggatttgg ggttgctctg gaaaactcat ttgcaccact   7320
gctgtgcctt ggaatgctag ttggagtaat aaatctctgg aacagatttg gaatcacacg   7380
acctggatgg agtgggacag agaaattaac aattacacaa gcttaataca ctccttaatt   7440
gaagaatcgc aaaaccagca agaaaagaat gaacaagaat tattggaatt agataaatgg   7500
gcaagtttgt ggaattggtt taacataaca aattggctgt ggtatataaa attattcata   7560
atgatagtag gaggcttggt aggtttaaga atagttttg ctgtactttc tatagtgaat   7620
agagttaggc agggatattc accattatcg tttcagaccc acctcccaac cccgagggga   7680
cccgacaggc ccgaaggaat agaagaagaa ggtggagaga gagacagaga cagatccatt   7740
cgattagtga acggatcggc actgcgtgcg ccaattctgc agacaaatgg cagtattcat   7800
ccacaatttt aaaagaaaag gggggattgg ggggtacagt gcaggggaaa gaatagtaga   7860
cataatagca acagacatac aaactaaaga attacaaaaa caaattacaa aaattcaaaa   7920
ttttcgggtt tattacaggg acagcagaga tccagtttgg ttaattaagg gtgcagcggc   7980
ctccgcgccg ggttttggcg cctccgcgg gcgccccct cctcacggcg agcgctgcca   8040
cgtcagacga agggcgcagg agcgttcctg atccttccgc ccggacgctc aggacagcgg   8100
cccgctgctc ataagactcg gccttagaac cccagtatca gcagaaggac attttaggac   8160
gggacttggg tgactctagg gcactggttt tcttccaga gagcggaaca ggcgaggaaa   8220
agtagtccct tctcggcgat tctgcggagg gatctccgtg gggcggtgaa cgccgatgat   8280
tatataagga cgcgccgggt gtggcacagc tagttccgtc gcagccggga tttgggtcgc   8340
ggttcttgtt tgtggatcgc tgtgatcgtc acttggtgag ttgcgggctg ctgggctggc   8400
cggggctttc gtggccgccg ggccgctcgg tgggacggaa gcgtgtggag agaccgccaa   8460
gggctgtagt ctgggtccgc gagcaaggtt gccctgaact gggggttggg gggagcgcac   8520
aaaatggcgg ctgttcccga gtcttgaatg gaagacgctt gtaaggcggg ctgtgaggtc   8580
gttgaaacaa ggtgggggc atggtgggcg gcaagaaccc aagtcttga ggccttcgct   8640
aatgcgggaa agctcttatt cgggtgagat gggctggggc accatctggg gaccctgacg   8700
tgaagtttgt cactgactgg agaactcggg tttgtcgtct ggttgcgggg gcggcagtta   8760
tgcggtgccg ttgggcagtg cacccgtacc tttgggagcg cgcgcctcgt cgtgtcgtga   8820
cgtcacccgt tctgttggct tataatgcag ggtggggcca cctgccggta ggtgtgcggt   8880
aggcttttct ccgtcgcagg acgcagggtt cgggcctagg gtaggctctc ctgaatcgac   8940
aggcgccgga cctctggtga ggggagggat aagtgaggcg tcagtttctt tggtcggttt   9000
tatgtaccta tcttcttaag tagctgaagc tccggttttg aactatgcgc tcggggttgg   9060
cgagtgtgtt ttgtgaagtt ttttaggcac cttttgaaat gtaatcattt gggtcaatat   9120
gtaattttca gtgttagact agtaaagctt ctgcaggtcg actctagaaa attgtccgct   9180
aaattctggc cgttttggc ttttttgtta gacaggatcc gttatcacaa gtttgtacaa   9240
aaaagcaggc tctttaaagg aaccaattca gtcgactgga tccggtaccg aattcgcggc   9300
```

```
cgcactcgag atgatgaaat ccttgagagt tttactggtg atcctgtggc ttcagttaag    9360
ctgggtttgg agccaacaga aggaggtgga gcaggatcct ggaccactca gtgttccaga    9420
gggagccatt gtttctctca actgcactta cagcaacagt gcttttcaat acttcatgtg    9480
gtacagacag tattccagaa aaggccctga gttgctgatg tacacatact ccagtggtaa    9540
caaagaagat ggaaggttta cagcacaggt cgataaatcc agcaagtata tctccttgtt    9600
catcagagac tcacagccca gtgattcagc cacctacctc tgtgcaatga gcagactgg     9660
aggcttcaaa actatctttg gagcaggaac aagactattt gttaaagcaa atatccagaa    9720
ccctgaccct gccgtgtacc agctgagaga ctctaaatcc agtgacaagt ctgtctgcct    9780
attcaccgat tttgattctc aaacaaatgt gtcacaaagt aaggattctg atgtgtatat    9840
cacagacaaa actgtgctag acatgaggtc tatggacttc aagagcaaca gtgctgtggc    9900
ctggagcaac aaatctgact tgcatgtgc  aaacgccttc aacaacagca ttattccaga    9960
agacaccttc ttccccagcc cagaaagttc tgtgatgtc  aagctggtcg agaaaagctt   10020
tgaaacagat acgaacctaa actttcaaaa cctgtcagtg attgggttcc gaatcctcct   10080
cctgaaagtg gccgggttta atctgctcat gacgctgcgg ctgtggtcca gcgggctaa    10140
gagaggttct ggagcaccgg tgaaacagac tttgaatttt gaccttctca gttggcggg    10200
agacgtggag tccaacccag ggcccatggg ccccagctc  cttggctatg tggtcctttg   10260
ccttctagga gcaggccccc tggaagccca agtgacccag aacccaagat acctcatcac   10320
agtgactgga aagaagttaa cagtgacttg ttctcagaat atgaaccatg agtatatgtc   10380
ctggtatcga caagacccag ggctgggctt aaggcagatc tactattcaa tgaatgttga   10440
ggtgactgat aagggagatg ttcctgaagg gtacaaagtc tctcgaaaag agaagaggaa   10500
tttccccctg atcctggagt cgcccagccc caaccagacc tctctgtact tctgtgccag   10560
cagtttagta gggacagcgg ggtcacccct ccactttggg aacggaccag gctcactgt    10620
gacagaggac ctgaacaagg tgttcccacc cgaggtcgct gtgtttgagc catcagaagc   10680
agagatctcc cacacccaaa aggccacact ggtgtgcctg ccacaggct  tcttccctga   10740
ccacgtggag ctgagctggt gggtgaatgg gaaggaggtg cacagtgggg tcagcacgga   10800
cccgcagccc ctcaaggagc agcccgccct caatgactcc agatactgcc tgagcagccg   10860
cctgagggtc tcggccacct tctgcagaa  cccccgcaac cacttccgct gtcaagtcca   10920
gttctacggg ctctcggaga atgacgagtg gacccaggat agggccaaac ccgtcaccca   10980
gatcgtcagc gccgaggcct ggggtagagc agactgtggc tttacctcgg tgtcctacca   11040
gcaagggtc  ctgtctgcca ccatcctcta tgagatcctg ctagggaagg ccaccctgta   11100
tgctgtgctg gtcagcgccc ttgtgttgat ggccatggtc aagagaaagg atttccgagc   11160
aaagagatcc ggaagcggag ccactaactt ctccctgttg aaacaagcag gggatgtcga   11220
agagaatccc gggccaatgc ccacgctact gcgggtttat atagacgtc  cccacgggat   11280
ggggaaaacc accaccacgc aactgctggt ggccctgggt tcgcgcgacg atatcgtcta   11340
cgtacccgag ccgatgactt actggcgggt gctgggggct tccgagacaa tcgcgaacat   11400
ctacaccaca caacaccgcc tcgaccaggg tgagatatcg gccggggacg cggcggtggt   11460
aatgacaagc gcccagataa caatgggcat gccttatgcc gtgaccgacg ccgttctggc   11520
tcctcatatc ggggggagg  ctgggagctc acatgccccg ccccggccc  tcaccatctt   11580
cctcgaccgc catcccatcg ccttcatgct gtgctacccg gccgcgcggt accttatggg   11640
cagcatgacc ccccaggccg tgctggcgtt cgtggccctc atcccgccga ccttgccgg    11700
```

```
caccaacatc gtgcttgggg cccttccgga ggacagacac atcgaccgcc tggccaaacg      11760
ccagcgcccc ggcgagcggc tggacctggc tatgctggct gcgattcgcc gcgtttacgg      11820
gctacttgcc aatacggtgc ggtatctgca gtgcggcggg tcgtggcggg aggactgggg      11880
acagctttcg gggacggccg tgccgcccca gggtgccgag ccccagagca acgcgggccc      11940
acgaccccat atcggggaca cgttatttac cctgtttcgg gcccccgagt tgctggcccc      12000
caacggcgac ctgtataacg tgtttgcctg ggccttggac gtcttggcca aacgcctccg      12060
ttccatgcac gtctttatcc tggattacga ccaatcgccc gccggctgcc gggacgccct      12120
gctgcaactt acctccggga tggtccagac ccacgtcacc accccggct ccataccgac       12180 gatatgcgac ctggcgcgca cgtttgcccg ggagatgggg gaggctaact gagcggccgc      12240
tcgagatatc tagacccagc tttc                                            12264
```

<210> SEQ ID NO 18
<211> LENGTH: 993
<212> TYPE: DNA
<213> ORGANISM: Artificial Sequence
<220> FEATURE:
<223> OTHER INFORMATION: Cloned nucleic acid sequence from Homo
      sapiens <400> SEQUENCE: 18

```
atgcccacgc tactgcgggt ttatatagac ggtccccacg ggatggggaa aaccaccacc        60
acgcaactgc tggtggccct gggttcgcgc gacgatatcg tctacgtacc cgagccgatg       120
acttactggc gggtgctggg ggcttccgag acaatcgcga acatctacac cacacaacac       180
cgcctcgacc agggtgagat atcggccggg gacgcggcgg tggtaatgac aagcgcccag       240
ataacaatgg gcatgcctta tgccgtgacc gacgccgttc tggctcctca tatcgggggg       300
gaggctggga gctcacatgc cccgccccg gccctcacca tcttcctcga ccgccatccc        360
atcgccttca tgctgtgcta cccggccgcg cggtacctta tgggcagcat gacccccag         420 gccgtgctgg cgttcgtggc cctcatcccg ccgaccttgc ccggcaccaa catcgtgctt       480
ggggcccttc cggaggacag acacatcgac cgcctggcca aacgccagcg ccccggcgag       540
cggctggacc tggctatgct ggctgcgatt cgccgcgttt acgggctact tgccaatacg       600
gtgcggtatc tgcagtgcgg cgggtcgtgg cggaggact ggggacagct ttcggggacg         660
gccgtgccgc cccagggtgc cgagcccag agcaacgcgg gccacgacc ccatatcggg         720 gacacgttat ttaccctgtt tcgggccccc gagttgctgg cccccaacgg cgacctgtat       780
aacgtgtttg cctgggcctt ggacgtcttg gccaaacgcc tccgttccat gcacgtcttt       840
atcctggatt acgaccaatc gcccgccggc tgccgggacg ccctgctgca acttacctcc       900
gggatggtcc agacccacgt caccaccccc ggctccatac cgacgatatg cgacctggcg       960
cgcacgtttg cccgggagat gggggaggct aac                                   993
```

<210> SEQ ID NO 19
<211> LENGTH: 118
<212> TYPE: PRT
<213> ORGANISM: Homo sapiens
<400> SEQUENCE: 19

```
Met Pro Arg Glu Asp Ala His Phe Ile Tyr Gly Tyr Pro Lys Lys Gly
 1               5                  10                  15

His Gly His Ser Tyr Thr Thr Ala Glu Glu Ala Ala Gly Ile Gly Ile
            20                  25                  30

Leu Thr Val Ile Leu Gly Val Leu Leu Leu Ile Gly Cys Trp Tyr Cys
```

```
                    35                  40                  45
Arg Arg Arg Asn Gly Tyr Arg Ala Leu Met Asp Lys Ser Leu His Val
 50                  55                  60

Gly Thr Gln Cys Ala Leu Thr Arg Arg Cys Pro Gln Glu Gly Phe Asp
 65                  70                  75                  80

His Arg Asp Ser Lys Val Ser Leu Gln Glu Lys Asn Cys Glu Pro Val
                 85                  90                  95

Val Pro Asn Ala Pro Pro Ala Tyr Glu Lys Leu Ser Ala Glu Gln Ser
                100                 105                 110

Pro Pro Pro Tyr Ser Pro
            115

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Glu Ala Ala Gly Ile Gly Ile Leu Thr Val
 1               5                  10

<210> SEQ ID NO 21
<211> LENGTH: 9941
<212> TYPE: DNA
<213> ORGANISM: Artificial Sequence
<220> FEATURE:
<223> OTHER INFORMATION: Constructed plasmid vector

<400> SEQUENCE: 21
```

| | | | | | |
|---|---|---|---|---|---|
| gtcgacggat | cgggagatct | cccgatcccc | tatggtgcac | tctcagtaca | atctgctctg | 60 |
| atgccgcata | gttaagccag | tatctgctcc | ctgcttgtgt | gttggaggtc | gctgagtagt | 120 |
| gcgcgagcaa | aatttaagct | acaacaaggc | aaggcttgac | cgacaattgc | atgaagaatc | 180 |
| tgcttagggt | taggcgtttt | gcgctgcttc | gcgatgtacg | ggccagatat | acgcgttgac | 240 |
| attgattatt | gactagttat | taatagtaat | caattacggg | gtcattagtt | catagcccat | 300 |
| atatggagtt | ccgcgttaca | taacttacgg | taaatggccc | gcctggctga | ccgcccaacg | 360 |
| acccccgccc | attgacgtca | ataatgacgt | atgttcccat | agtaacgcca | atagggactt | 420 |
| tccattgacg | tcaatgggtg | gagtatttac | ggtaaactgc | ccacttggca | gtacatcaag | 480 |
| tgtatcatat | gccaagtacg | cccctattg | acgtcaatga | cggtaaatgg | cccgcctggc | 540 |
| attatgccca | gtacatgacc | ttatgggact | ttcctacttg | gcagtacatc | tacgtattag | 600 |
| tcatcgctat | taccatggtg | atgcggtttt | ggcagtacat | caatgggcgt | ggatagcggt | 660 |
| ttgactcacg | gggatttcca | agtctccacc | ccattgacgt | caatgggagt | ttgttttggc | 720 |
| accaaaatca | acgggacttt | ccaaaatgtc | gtaacaactc | cgccccattg | acgcaaatgg | 780 |
| gcggtaggcg | tgtacggtgg | gaggtctata | taagcagcgc | gttttgcctg | tactgggtct | 840 |
| ctctggttag | accagatctg | agcctgggag | ctctctggct | aactagggaa | cccactgctt | 900 |
| aagcctcaat | aaagcttgcc | ttgagtgctt | caagtagtgt | gtgcccgtct | gttgtgtgac | 960 |
| tctggtaact | agagatccct | cagacccttt | tagtcagtgt | ggaaaatctc | tagcagtggc | 1020 |
| gcccgaacag | ggacttgaaa | gcgaaaggga | aaccagagga | gctctctcga | cgcaggactc | 1080 |
| ggcttgctga | agcgcgcacg | gcaagaggcg | aggggcggcg | actggtgagt | acgccaaaaa | 1140 |
| ttttgactag | cggaggctag | aaggagagag | atgggtgcga | gagcgtcagt | attaagcggg | 1200 |

```
ggagaattag atcgcgatgg gaaaaaattc ggttaaggcc aggggggaaag aaaaaatata    1260 aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctggggatt    1920
tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagacagag acagatccat tcgattag tgaacggatc ggcactgcgt    2400
gcgccaattc tgcagacaaa tggcagtatt catccacaat tttaaaagaa aagggggggat    2460 tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta agggtgcagc ggcctccgcg ccgggttttg gcgcctcccg    2640
cgggcgcccc cctcctcacg gcgagcgctg ccacgtcaga cgaagggcgc aggagcgttc    2700
ctgatccttc cgcccggacg ctcaggacag cggcccgctg ctcataagac tcggccttag    2760
aaccccagta tcagcagaag gacattttag gacgggactt gggtgactct agggcactgg    2820
ttttctttcc agagagcgga acaggcgagg aaaagtagtc ccttctcggc gattctgcgg    2880
agggatctcc gtgggcggt gaacgccgat gattatataa ggacgcgccg ggtgtggcac    2940
agctagttcc gtcgcagccg ggatttgggt cgcggttctt gtttgtggat cgctgtgatc    3000
gtcacttggt gagttgcggg ctgctgggct ggccggggct ttcgtggccg ccgggccgct    3060
cggtgggacg gaagcgtgtg gagagaccgc caagggctgt agtctgggtc cgcgagcaag    3120
gttgccctga actgggggtt gggggagcg cacaaaatgg cggctgttcc cgagtcttga    3180
atggaagacg cttgtaaggc gggctgtgag gtcgttgaaa caaggtgggg ggcatggtgg    3240
gcggcaagaa cccaaggtct tgaggccttc gctaatgcgg gaaagctctt attcgggtga    3300
gatgggctgg ggcaccatct ggggaccctg acgtgaagtt tgtcactgac tggagaactc    3360
gggtttgtcg tctggttgcg ggggcggcag ttatgcggtg ccgttgggca gtgcacccgt    3420
acctttggga gcgcgcgcct cgtcgtgtcg tgacgtcacc cgttctgttg cttataatg    3480 cagggtgggg ccacctgccg gtaggtgtgc ggtaggcttt tctccgtcgc aggacgcagg    3540
gttcgggcct agggtaggct ctcctgaatc gacaggcgcc ggacctctgg tgaggggagg    3600
```

```
gataagtgag gcgtcagttt ctttggtcgg ttttatgtac ctatcttctt aagtagctga    3660
agctccggtt ttgaactatg cgctcggggt tggcgagtgt gttttgtgaa gttttttagg    3720 cacctttga  aatgtaatca tttgggtcaa tatgtaattt tcagtgttag actagtaaag    3780
cttctgcagg tcgactctag aaaattgtcc gctaaattct ggccgttttt ggctttttg    3840 ttagacagga tccccgggta ccggtcgcca ccatggtgag caagggcgag gagctgttca    3900
ccggggtggt gcccatcctg gtcgagctgg acggcgacgt aaacggccac aagttcagcg    3960
tgtccggcga gggcgagggc gatgccacct acggcaagct gaccctgaag ttcatctgca    4020
ccaccggcaa gctgcccgtg ccctggccca cctcgtgac  cacccctgacc tacggcgtgc    4080 agtgcttcag ccgctacccc gaccacatga agcagcacga cttcttcaag tccgccatgc    4140
ccgaaggcta cgtccaggag cgcaccatct tcttcaagga cgacggcaac tacaagaccc    4200
gcgccgaggt gaagttcgag ggcgacaccc tggtgaaccg catcgagctg aagggcatcg    4260
acttcaagga ggacggcaac atcctggggc acaagctgga gtacaactac aacagccaca    4320
acgtctatat catggccgac aagcagaaga acggcatcaa ggtgaacttc aagatccgcc    4380
acaacatcga ggacggcagc gtgcagctcg ccgaccacta ccagcagaac ccccccatcg    4440
gcgacggccc cgtgctgctg cccgacaacc actacctgag cacccagtcc gccctgagca    4500
aagaccccaa cgagaagcgc gatcacatgg tcctgctgga gttcgtgacc gccgccggga    4560
tcactctcgg catggacgag ctgtacaagt aaagcggccg cgactctaga attcgatatc    4620
aagcttatcg ataatcaacc tctgattaca aaatttgtg  aaagattgac tggtattctt    4680
aactatgttg ctccttttac gctatgtgga tacgctgctt taatgccttt gtatcatgct    4740
attgcttccc gtatggcttt cattttctcc tccttgtata atcctggtt  gctgtctctt    4800 tatgaggagt tgtggcccgt tgtcaggcaa cgtggcgtgg tgtgcactgt gtttgctgac    4860
gcaaccccca ctggttgggg cattgccacc acctgtcagc tcctttccgg gactttcgct    4920
ttccccctcc ctattgccac ggcggaactc atcgccgcct gccttgcccg ctgctggaca    4980
ggggctcggc tgttgggcac tgacaattcc gtggtgttgt cggggaaatc atcgtccttt    5040
ccttggctgc tcgcctgtgt tgccacctgg attctgcgcg gacgtccttc tgctacgtc    5100 ccttcggccc tcaatccagc ggaccttcct tcccgcggcc tgctgccggc tctgcggcct    5160
cttccgcgtc ttcgccttcg ccctcagacg agtcggatct ccctttgggc cgcctccccg    5220
catcgatacc gtcgacctcg agacctagaa aaacatggag caatcacaag tagcaataca    5280
gcagctacca atgctgattg tgcctggcta gaagcacaag aggaggagga ggtgggtttt    5340
ccagtcacac ctcaggtacc tttaagacca atgacttaca aggcagctgt agatcttagc    5400
cactttttaa aagaaaaggg gggactgaa  gggctaattc actcccaacg aagacaagat    5460
atccttgatc tgtggatcta ccacacacaa ggctacttcc ctgattggca gaactacaca    5520
ccagggccag ggatcagata tccactgacc tttggatggt gctacaagct agtaccagtt    5580
gagcaagaga aggtagaaga agccaatgaa ggagagaaca cccgcttgtt acaccctgtg    5640
agcctgcatg gatggatga  cccggagaga gaagtattag agtggaggtt tgacagccgc    5700
ctagcatttc atcacatggc ccgagagctg catccggact gtactgggtc tctctggtta    5760
gaccagatct gagcctggga gctctctggc taactaggga acccactgct taagcctcaa    5820
taaagcttgc cttgagtgct tcaagtagtg tgtgcccgtc tgttgtgtga ctctggtaac    5880
tagagatccc tcagaccctt ttagtcagtg tggaaaatct ctagcagggc ccgtttaaac    5940
ccgctgatca gcctcgactg tgccttctag ttgccagcca tctgttgttt gcccctcccc    6000
```

```
cgtgccttcc ttgaccctgg aaggtgccac tcccactgtc ctttcctaat aaaatgagga    6060
aattgcatcg cattgtctga gtaggtgtca ttctattctg gggggtgggg tggggcagga    6120
cagcaagggg gaggattggg aagacaatag caggcatgct ggggatgcgg tgggctctat    6180
ggcttctgag gcggaaagaa ccagctgggg ctctaggggg tatccccacg cgccctgtag    6240
cggcgcatta agcgcggcgg gtgtggtggt tacgcgcagc gtgaccgcta cacttgccag    6300
cgccctagcg cccgctcctt tcgctttctt cccttccttt ctcgccacgt tcgccggctt    6360
tccccgtcaa gctctaaatc gggggctccc tttagggttc cgatttagtg ctttacggca    6420
cctcgacccc aaaaaacttg attagggtga tggttcacgt agtgggccat cgccctgata    6480
gacggttttt cgccctttga cgttggagtc cacgttcttt aatagtggac tcttgttcca    6540
aactggaaca acactcaacc ctatctcggt ctattctttt gatttataag gattttgcc    6600 gatttcggcc tattggttaa aaatgagct gatttaacaa aaatttaacg cgaattaatt    6660
ctgtggaatg tgtgtcagtt agggtgtgga aagtccccag gctccccagc aggcagaagt    6720
atgcaaagca tgcatctcaa ttagtcagca accaggtgtg gaaagtcccc aggctcccca    6780
gcaggcagaa gtatgcaaag catgcatctc aattagtcag caaccatagt cccgccccta    6840
actccgccca tcccgcccct aactccgccc agttccgccc attctccgcc ccatggctga    6900 ctaattttt ttatttatgc agaggccgag gccgcctctg cctctgagct attccagaag    6960
tagtgaggag gctttttgg aggcctaggc ttttgcaaaa agctcccggg agcttgtata    7020
tccattttcg gatctgatca gcacgtgttg acaattaatc atcggcatag tatatcggca    7080
tagtataata cgacaaggtg aggaactaaa ccatggccaa gttgaccagt gccgttccgg    7140
tgctcaccgc gcgcgacgtc gccggagcgg tcgagttctg gaccgaccgg ctcgggttct    7200
cccgggactt cgtggaggac gacttcgccg gtgtggtccg gacgacgtg accctgttca    7260 tcagcgcggt ccaggaccag gtggtgccgg acaacaccct ggcctgggtg tgggtgcgcg    7320
gcctggacga gctgtacgcc gagtggtcgg aggtcgtgtc cacgaacttc cgggacgcct    7380
ccgggccggc catgaccgag atcggcgagc agcgtggg gcgggagttc gccctgcgcg    7440
acccggccgg caactgcgtg cacttcgtgg ccgaggagca ggactgacac gtgctacgag    7500
atttcgattc caccgccgcc ttctatgaaa ggttgggctt cggaatcgtt ttccgggacg    7560
ccggctggat gatcctccag cgcggggatc tcatgctgga gttcttcgcc cacccccaact    7620 tgtttattgc agcttataat ggttacaaat aaagcaatag catcacaaat ttcacaaata    7680
aagcattttt tcactgcat tctagttgtg gtttgtccaa actcatcaat gtatcttatc    7740
atgtctgtat accgtcgacc tctagctaga gcttggcgta atcatggtca gctgtttc    7800 ctgtgtgaaa ttgttatccg ctcacaattc cacacaacat acgagccgga agcataaagt    7860
gtaaagcctg gggtgcctaa tgagtgagct aactcacatt aattgcgttg cgctcactgc    7920
ccgctttcca gtcgggaaac ctgtcgtgcc agctgcatta tgaatcggc caacgcgcgg    7980 ggagaggcgg tttgcgtatt gggcgctctt ccgcttcctc gctcactgac tcgctgcgct    8040
cggtcgttcg gctgcggcga gcggtatcag ctcactcaaa ggcggtaata cggttatcca    8100
cagaatcagg ggataacgca ggaaagaaca tgtgagcaaa aggccagcaa aaggccagga    8160
accgtaaaaa ggccgcgttg ctggcgtttt tccataggct ccgcccccct gacgagcatc    8220
acaaaaatcg acgctcaagt cagaggtggc gaaacccgac aggactataa agataccagg    8280
cgtttccccc tggaagctcc ctcgtgcgct ctcctgttcc gaccctgccg cttaccggat    8340
acctgtccgc ctttctccct tcgggaagcg tggcgctttc tcatagctca cgctgtaggt    8400
```

```
                                                        -continued
atctcagttc ggtgtaggtc gttcgctcca agctgggctg tgtgcacgaa ccccccgttc    8460
agcccgaccg ctgcgcctta tccggtaact atcgtcttga gtccaacccg gtaagacacg    8520
acttatcgcc actggcagca gccactggta acaggattag cagagcgagg tatgtaggcg    8580
gtgctacaga gttcttgaag tggtggccta actacggcta cactagaaga acagtatttg    8640
gtatctgcgc tctgctgaag ccagttacct tcggaaaaag agttggtagc tcttgatccg    8700
gcaaacaaac caccgctggt agcggtggtt tttttgtttg caagcagcag attacgcgca    8760
gaaaaaaagg atctcaagaa gatcctttga tcttttctac ggggtctgac gctcagtgga    8820
acgaaaactc acgttaaggg attttggtca tgagattatc aaaaaggatc ttcacctaga    8880
tccttttaaa ttaaaaatga agttttaaat caatctaaag tatatatgag taaacttggt    8940
ctgacagtta ccaatgctta atcagtgagg cacctatctc agcgatctgt ctatttcgtt    9000
catccatagt tgcctgactc cccgtcgtgt agataactac gatacgggag ggcttaccat    9060
ctggccccag tgctgcaatg ataccgcgag acccacgctc accggctcca gatttatcag    9120
caataaacca gccagccgga agggccgagc gcagaagtgg tcctgcaact ttatccgcct    9180
ccatccagtc tattaattgt tgccgggaag ctagagtaag tagttcgcca gttaatagtt    9240
tgcgcaacgt tgttgccatt gctacaggca tcgtggtgtc acgctcgtcg tttggtatgg    9300
cttcattcag ctccggttcc caacgatcaa ggcgagttac atgatccccc atgttgtgca    9360
aaaaagcggt tagctccttc ggtcctccga tcgttgtcag aagtaagttg gccgcagtgt    9420
tatcactcat ggttatggca gcactgcata attctcttac tgtcatgcca tccgtaagat    9480
gcttttctgt gactggtgag tactcaacca agtcattctg agaatagtgt atgcggcgac    9540
cgagttgctc ttgcccggcg tcaatacggg ataataccgc gccacatagc agaactttaa    9600
aagtgctcat cattggaaaa cgttcttcgg ggcgaaaact ctcaaggatc ttaccgctgt    9660
tgagatccag ttcgatgtaa cccactcgtg cacccaactg atcttcagca tcttttactt    9720
tcaccagcgt ttctgggtga gcaaaaacag gaaggcaaaa tgccgcaaaa aagggaataa    9780
gggcgacacg gaaatgttga atactcatac tcttcctttt tcaatattat tgaagcattt    9840
atcagggtta ttgtctcatg agcggataca tatttgaatg tatttagaaa aataaacaaa    9900 tagggggttcc gcgcacattt ccccgaaaag tgccacctga c                      9941
```